US011613739B2

(12) United States Patent
Yoo et al.

(10) Patent No.: US 11,613,739 B2
(45) Date of Patent: Mar. 28, 2023

(54) TREATMENT OF MUCOPOLYSACCHARIDOSIS II WITH RECOMBINANT HUMAN IDURONATE-2-SULFATASE (IDS) PRODUCED BY HUMAN NEURAL OR GLIAL CELLS

(71) Applicant: REGENXBIO Inc., Rockville, MD (US)

(72) Inventors: Stephen Yoo, Newton, MA (US); Rickey Robert Reinhardt, Silver Spring, MD (US); Curran Matthew Simpson, Frederick, MD (US); Zhuchun Wu, Potomac, MD (US)

(73) Assignee: REGENXBIO Inc., Rockville, MD (US)

( * ) Notice: Subject to any disclaimer, the term of this patent is extended or adjusted under 35 U.S.C. 154(b) by 695 days.

(21) Appl. No.: 16/604,427

(22) PCT Filed: Apr. 13, 2018

(86) PCT No.: PCT/US2018/027568
§ 371 (c)(1),
(2) Date: Oct. 10, 2019

(87) PCT Pub. No.: WO2018/191666
PCT Pub. Date: Oct. 18, 2018

(65) Prior Publication Data
US 2020/0149019 A1 May 14, 2020

Related U.S. Application Data

(60) Provisional application No. 62/579,686, filed on Oct. 31, 2017, provisional application No. 62/574,355, filed on Oct. 19, 2017, provisional application No. 62/573,921, filed on Oct. 18, 2017, provisional application No. 62/485,659, filed on Apr. 14, 2017.

(51) Int. Cl.
| | |
|---|---|
| *C12N 9/16* | (2006.01) |
| *A61P 3/00* | (2006.01) |
| *A61K 9/00* | (2006.01) |
| *A61K 35/76* | (2015.01) |
| *C12N 15/86* | (2006.01) |
| *A61K 38/00* | (2006.01) |
| *A61K 48/00* | (2006.01) |

(52) U.S. Cl.
CPC .............. *C12N 9/16* (2013.01); *A61K 9/0043* (2013.01); *A61K 9/0085* (2013.01); *A61K 35/76* (2013.01); *A61P 3/00* (2018.01); *C12N 15/86* (2013.01); *C12Y 301/06013* (2013.01); *A61K 38/00* (2013.01); *A61K 48/00* (2013.01); *C12N 2750/14121* (2013.01); *C12N 2750/14132* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,596,535 B1 | 7/2003 | Carter et al. |
| 7,125,717 B2 | 10/2006 | Carter et al. |
| 7,282,199 B2 | 10/2007 | Gao et al. |
| 7,456,683 B2 | 11/2008 | Takano et al. |
| 7,790,449 B2 | 9/2010 | Gao et al. |
| 7,906,111 B2 | 3/2011 | Wilson et al. |
| 8,318,480 B2 | 11/2012 | Gao et al. |
| 8,524,446 B2 | 9/2013 | Gao et al. |
| 8,628,966 B2 | 1/2014 | Chatterjee et al. |
| 8,734,809 B2 | 5/2014 | Gao et al. |
| 8,927,514 B2 | 1/2015 | Chatterjee et al. |
| 8,962,332 B2 | 2/2015 | Gao et al. |
| 8,999,678 B2 | 4/2015 | Weiler et al. |
| 9,169,299 B2 | 10/2015 | Lisowski et al. |
| 9,193,956 B2 | 11/2015 | Schaffer et al. |
| 9,284,357 B2 | 3/2016 | Gao et al. |
| 9,409,953 B2 | 8/2016 | Asokan et al. |
| 9,458,517 B2 | 10/2016 | Schaffer et al. |
| 9,585,971 B2 | 3/2017 | Deverman et al. |
| 9,587,282 B2 | 3/2017 | Schaffer et al. |
| 2013/0224836 A1 | 8/2013 | Muramatsu et al. |
| 2014/0242059 A1 | 8/2014 | Thong-Gyu et al. |
| 2015/0126588 A1 | 5/2015 | Nakai et al. |
| 2015/0374803 A1 | 12/2015 | Wolfe et al. |
| 2016/0215024 A1 | 7/2016 | Vandenberghe et al. |

(Continued)

FOREIGN PATENT DOCUMENTS

| | | |
|---|---|---|
| WO | WO 2011/163649 | 12/2011 |
| WO | WO 2012/177020 | 12/2012 |

(Continued)

OTHER PUBLICATIONS

Clinical Trials Government Identifier: NCT00920647, retrieved at https://www.clinicaltrials.gov/ct2/show/study/NCT00920647?term= mucopolysaccharidosis+type+II, by Takeda (Shire), first posted Jun. 15, 2009, results first posted May 16, 2014, 11 pages as printed. (Year: 2014).*
Chung, et al. (2014) "A biochemical and physicochemical comparison of two recombinant enzymes used for enzyme replacement therapies of hunter syndrome", Glycoconjugate Journal, 31(4): 309-15. (Year: 2014).*
Callas, et al. (2012) "CNS Penetration of Intrathecal-Lumber Indursulfase in the Monkey, Dog and Mouse: Implications for Neurological Outcomes of Lysosomal Storage Disorder", PLoS One, 7(1): article e30341, 13 pages. (Year: 2012).*

(Continued)

*Primary Examiner* — Robert M Kelly
(74) *Attorney, Agent, or Firm* — Jones Day

(57) ABSTRACT

Compositions and methods are described for the delivery of recombinant human iduronate-2-sulfatase (IDS) produced by human neuronal or glial cells to the cerebrospinal fluid of the central nervous system (CNS) of a human subject diagnosed with mucopolysaccharidosis II (MPS II).

16 Claims, 13 Drawing Sheets

Figure 4:
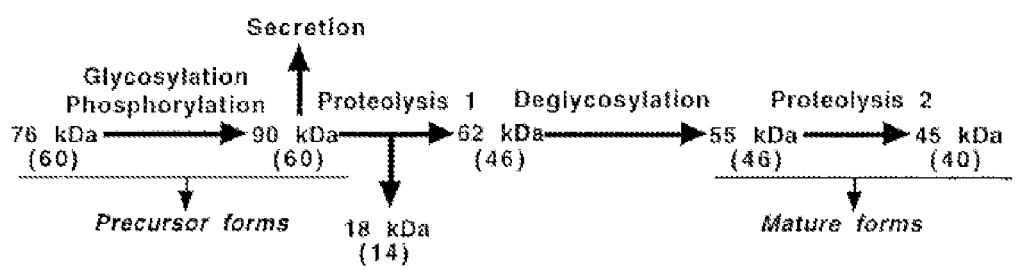

Specification includes a Sequence Listing.

(56) References Cited

U.S. PATENT DOCUMENTS

| | | |
|---|---|---|
| 2016/0376323 A1 | 12/2016 | Schaffer et al. |
| 2017/0051257 A1 | 2/2017 | Vandenberghe et al. |
| 2017/0067908 A1 | 3/2017 | Nakai et al. |

FOREIGN PATENT DOCUMENTS

| | | |
|---|---|---|
| WO | WO 2015/082570 | 6/2015 |
| WO | WO 2015/121501 | 8/2015 |
| WO | WO 2016/126729 | 8/2015 |
| WO | WO 2015/191508 | 12/2015 |
| WO | WO 2016/007909 | 1/2016 |
| WO | WO 2016/077356 | 5/2016 |
| WO | WO 2016/100603 | 6/2016 |
| WO | WO 2016/187017 | 11/2016 |
| WO | WO 2016/193431 | 12/2016 |
| WO | WO 2017/181113 | 10/2017 |
| WO | WO 2018/191666 | 10/2018 |
| WO | WO 2021/154963 | 8/2021 |

OTHER PUBLICATIONS

International Search Report and Written Opinion dated Jul. 16, 2018 for PCT/US2018/027568 (17 pages).
Bielicki et al., 1993, "Recombinant human iduronate-2-sulphatase: correction of mucopolysaccharidosis-type II fibroblasts and characterization of the purified enzyme", Biochem J, 289(1):241-246.
Daniele et al., 2002, "Uptake of recombinant iduronate-2-sulfatase into neuronal and glial cells in vitro," Biochim Biophys Acta., 1588(3):203-209.
Genbank, 2016, NM_010498: Mus musculus iduronate 2-sulfatase (ids), mRNA, 5 pages, retrieved from the internet: <https://www.ncbi.nlm.nih.gov/nuccore/262205477>.
Ghaderi et al., 2013, "Production platforms for biotherapeutic glycoproteins. Occurrence, impact, and challenges of non-human sialylation", Biotechnol. Genet. Eng. Rev., 28:147-175.
Hinderer et al., 2016, "Delivery of an Adeno-Associated Virus Vector into Cerebrospinal Fluid Attenuates Central Nervous System Disease in Mucopolysaccharidosis Type II Mice", Hum Gene Ther, 27(11):906-915.
Motas et al., 2016, "CNS-directed gene therapy for the treatment of neurologic and somatic mucopolysaccharidosis type II (Hunter syndrome)", JCI Insight, 1(9): e86696:1-18.
Zuber et al., 2014, "The effect of recombinant human iduronate-2-sulfatase (idursulfase) on growth in young patients with Mucopolysaccharidosis Type II", PLoS One, 9(1):1-5.
Alba et al., 2005, "Gutless adenovirus: last-generation adenovirus for gene therapy", Gene Therapy, 12:S18-S27.
Ausubel et al, 2012, "Production of CGMP-Grade Lentiviral Vectors," BioProcess International, 10(2):32-43.
Ayoub et al., 2013, "Correct primary structure assessment and extensive glyco-profiling of cetuximab by a combination of intact, middle-up, middle-down and bottom-up ESI and MALDI mass spectrometry techniques", Landes Bioscience, 5(5):699-710.
Bonuccelli et al., 2001, "The effect of four mutations on the expression of iduronate-2-sulfatase in mucopolysaccharidosis type II," Biochimica et Biophysica Acta (BBA)—Molecular Basis of Disease, 1537(3):233-238.
Bosques et al., 2010, "Chinese hamster ovary cells can produce galactose-α-1,3-galactose antigens on proteins", Nature Biotechnology, 28:1153-1156.
Bundgaard et al., 1995, "Tyrosine O-sulfation promotes proteolytic processing of progastrin," The EMBO Journal, 14(13):3073-3079.
Chung et al., 2014, "A biochemical and physicochemical comparison of two recombinant enzymes used for enzyme replacement therapies of hunter syndrome," Glycoconjugate Journal, 31:309-315.
Clarke, L, 2008, "Idursulfase for the treatment of mucopolysaccharidosis II," Expert Opinion on Pharmacotherapy, 9(2):311-317.

Cohen-Pfeffer et al., 2017, "Intracerebroventricular Delivery as a Safe, Long-Term Route of Drug Administration," Pediatric Neurology, 67:23-25.
D'Avanzo et al., 2020, "Mucopolysaccharidosis Type II: One Hundred Years of Research, Diagnosis, and Treatment," International Journal of Molecular Sciences, 21(4):1258; Retrieved from the Internet: URL:https://www.ncbi.nlm.nih.gov/pmc/articles/PMC7072947/pdf/ijms-21-01258.pdf> see p. 13.
Dean et al., 2006, "Detection of Mucopolysaccharidosis Type II by Measurement of Iduronate-2-Sulfatase in Dried Blood Spots and Plasma Samples," Clinical Chemistry, 52(4):643-649.
Dekaban, AS, 1978, "Changes in brain weights during the span of human life: relation of brain weights to body heights and body weights," Annals of Neurology, 4(4):345-356.
Dinculescu et al., 2005, "Adeno-associated virus-vectored gene therapy for retinal disease", Human Gene Therapy, 16(6):649-663.
Drake et al., 2000, "CSF shunts 50 years on—past, present and future," Child's Nervous System, 16:800-804.
Dumont et al., 2015, "Human cell lines for biopharmaceutical manufacturing: history, status, and future perspectives," Critical Reviews in Biotechnology, Early Online: 1-13.
Elaprase (idursulfase) injection [package insert] Lexington, MA: Shire Human Genetic Therapies, Inc; 2013, available at http://pi.shirecontent.com/PI/PDFs/Elaprase_USA_ENG.pdf.
Ferreira et al., 2009, "Sleep Disturbance Scale for Children: Translation, cultural adaptation, and validation," Sleep Medicine, 10(4):457-463.
Froissart et al., 1995, "Processing of iduronate 2-sulphatase in human fibroblasts," Biochemical Journal, 309(2):425-430.
Galili et al., 1998, "A sensitive assay for measuring alpha-Gal epitope expression on cells by a monoclonal anti-Gal antibody", Transplantaion, 65(8):1129-1132.
Garcia et al., 2007, "The characterization of a murine model of mucopolysaccharidosis II (Hunter syndrome)," Journal of Inherited Metabolic Disease, 30:924-934.
Hague et al., 1998, "Structural determination of oligosaccharides from recombinant iduronidase released with peptide N-glycanase F using fluorophore-assisted carbohydrate electrophoresis," Electrophoresis, 19(15):2612-2620.
Hara et al., 1989, "Highly sensitive determination of N-acetyl- and N-glycolylneuraminic acids in human serum and urine and rat serum by reversed-phase liquid chromatography with fluorescence detection," Journal of Chromatography B: Biomedical Sciences and Applications, 377:111-119.
Hocquemiller et al., 2016, "Adeno-Associated Virus-Based Gene Therapy for CNS Diseases," Human Gene Therapy, 27(7):478-496.
International Search Report and Written Opinion dated May 10, 2021 for PCT/US2021/015446.
Kanan and Al-Ubaidi., 2015, "Protein tyrosine-O-sulfation in the retina," Experimental Eye Research, 89:559-567.
Kanan et al., 2015, "Role of tyrosine-sulfated proteins in retinal structure and function," Experimental Eye Research, 133:126-131.
Kato et al., 2007, "Evaluation of ADL in patients with Hunter disease using FIM score," Brain and Development, 29(5):298-305.
Kratzer et al., 2003, "Factors Affecting Liver Size a Sonographic Survey of 2080 Subjects," Journal of Ultrasound Medicine, 22(11):1155-1161.
Lee et al., 2015, "Direct assay of iduronate-2-sulfatase for Hunter disease using UPLC-tandem mass spectrometry and fluorogenic substrate," Clinical Biochemistry, 48(18):1350-1353.
Lesch et al., 2011, "Production and purification of lentiviral vectors generated in 293T suspension cells with baculoviral vectors", Gene Therapy, 18(6):531-538.
Martin et al., 2008, "Recognition and Diagnosis of Mucopolysaccharidosis II (Hunter Syndrome)," Pediatrics, 121(2):e377-e386.
McCarty et al., 2001, "Self-complementary recombinant adeno-associated virus (scAAV) vectors promote efficient transduction independently of DNA synthesis", Gene Therapy, 8(16):1248-1254.
Mikkelsen and Ezban, 1991, "Heterogeneity in the tyrosine sulfation of Chinese hamster ovary cell produced recombinant FVIII", Biochemistry, 30(6):1533-1537.

(56) References Cited

OTHER PUBLICATIONS

Millat et al., 1997, "Characterization of iduronate sulphatase mutants affecting N-glycosylation sites and the cysteine-84 residue," Biochemical Journal, 326(1):243-247.
Millat et al., 1998, "COS cell expression studies of P86L, P86R, P480L and P480Q Hunter's disease-causing mutations," Biochimica et Biophysica Acta (BBA)—Molecular Basis of Disease, 1406(2):214-218.
Millat et al., 1997, "IDS Transfer from Overexpressing Cells to IDS-Deficient Cells," Experimental Cell Research, 230(2):362-367.
Miyazaki et al., 1989, "Expression vector system based on the chicken beta-actin promoter directs efficient production of interleukin-5," Gene, 79(2):269-277.
Moore et al., 2003, "The biology and enzymology of protein tyrosine O-sulfation", Journal of Biological Chemistry, 278(27):24243-24246.
Muenzer et al., 2016, "A phase I/II study of intrathecal idursulfase-IT in children with severe mucopolysaccharidosis II," Genetics in Medicine, 18:73-81.
Muenzer et al., 2002, "Enzyme replacement therapy in mucopolysaccharidosis type II (Hunter syndrome): a preliminary report," Acta Paediatrica Supplement, 91(439):98-99.
Muenzer et al., 2009, "Mucopolysaccharidosis I: Management and Treatment Guidelines," Pediatrics, 123(1):19-29.
Niwa et al., 1991, "Efficient selection for high-expression transfectants with a novel eukaryotic vector," Gene, 108(2):193-199.
Platts-Mills et al., 2015, "Anaphylaxis to the carbohydrate side chain alpha-gal," Immunology and Allergy Clinics of North America, 35(2):247-260.
Polito and Cosma, 2009, "IDS Crossing of the Blood-Brain Barrier Corrects CNS Defects in MPSII Mice," The American Journal of Human Genetics, 85(2):296-301.
Quax et al., 2015, "Codon Bias as a Means to Fine-Tune Gene Expression", Molecular Cell, 59(2):149-161.
Regenxbio Press Release; 2018, "Regenxbio Announces Interim Data From Phase I/II Trial of RGX-121 for the Treatment of Mucopolysaccharidosis Type II (MPS II)", 8 pages, Retrieved from the internet at: <http://ir.regenxbio.com/news-releases/news-release-details/regenxbio-announces-interim-data-phase-iii-trial-rgx-121> on Feb. 3, 2020.
Royle et al., 2002, "An analytical and structural database provides a strategy for sequencing O-glycans from microgram quantities of glycoproteins", Analytical Biochemistry, 304(1):70-90.
Schmidt et al., 1995, "A novel amino acid modification in sulfatases that is defective in multiple sulfatase deficiency," Cell, 82(2):271-278.
Search Report dated Dec. 16, 2020 for European Pat. App. No. 18783760.4.
Slavc et al., 2018, "Best practices for the use of intracerebroventricular drug delivery devices," Molecular Genetics and Metabolism, 124:184-188.
Sleat et al., 2006, "Identification of Sites of Mannose 6-Phosphorylation on Lysosomal Proteins," Molecular & Cellular Proteomics, 5(4):686-701.
Sleat et al., 1996, "Rat brain contains high levels of mannose-6-phosphorylated glycoproteins including lysosomal enzymes and palmitoyl-protein thioesterase, an enzyme implicated in infantile neuronal lipofuscinosis," Journal of Biological Chemistry, 271(32):19191-19198.
Sleat et al., 2005, "The human brain mannose 6-phosphate glycoproteome: a complex mixture composed of multiple isoforms of many soluble lysosomal proteins," Proteomics, 5(6):1520-1532.
Smith et al., 2014, "Gene transfer properties and structural modeling of human stem cell-derived AAV," Molecular Therapy, 22(9):1625-1634.
Stroncek et al., 1999, "Retroviral transduction and expansion of peripheral blood lymphocytes for the treatment of mucopolysaccharidosis type II, Hunter's syndrome," Transfusion, 39(4):343-350.
Sukegawa-Hayasaka et al., 2006, "Effect of Hunter disease (mucopolysaccharidosis type II) mutations on molecular phenotypes of iduronate-2-sulfatase: Enzymatic activity, protein processing and structural analysis," Journal of Inherited Hetabolic Disease, 29(6):755-761.
Tanjuakio et al., 2015, "Activities of daily living in patients with Hunter syndrome: Impact of enzyme replacement therapy and hematopoietic stem cell transplantation," Molecular Genetics and Metabolism, 114(2):161-169.
Wraith et al., 2007, "Enzyme replacement therapy in patients who have mucopolysaccharidosis I and are younger than 5 years: results of a multinational study of recombinant human alpha-L-iduronidase (laronidase)," Pediatrics, 120(1):e37-e46.
Wu et al., 2007, "Self-complementary recombinant adeno-associated viral vectors: packaging capacity and the role of rep proteins in vector purity", Human Gene Therapy, 18(2):171-182.
Yan et al., 2005, "Inverted terminal repeat sequences are important for intermolecular recombination and circularization of adeno-associated virus genomes", Journal of Virology, 79(1):364-379.
Yang et al., 2015, "Tyrosine sulfation as a protein post-translational modification", Molecules, 20(2):2138-2164.
Young et al., 1982, A clinical and genetic study of Hunter's syndrome. 2 Differences between the mild and severe forms, Journal of Medicical Genetics, 19(6):408-411.
Zinn et al., 2015, "In Silico Reconstruction of the Viral Evolutionary Lineage Yields a Potent Gene Therapy Vector," Cell Reports, 12(6):1056-1068.

* cited by examiner

Amino Acid Sequence of Human IDS

```
Iduronate-2-sulfatase (IDS)

→Signal                                    →Mature 42kD
         10         20         30         40         50
   MPPPRTGRGL LWLGLVLSSV CVALGSETQA ▓STIDALNVL LIIVDDLRPS
         60         70         80         90        100
   LGCYGDKLVR SPNIDQLASH SLLFQNAFAQ QAVCAPSRVS FLTGRRPDTT
        110        120        130        140        150
   RLYDFNSYWR VHAG▓FSTIP QYFKENGYVT MSVGKVFHPG ISS▓HTDDSP
        160        170        180        190        200
   YSWSFPPYHP SSEKYENTKT CRGPDELHA  NLLCPVDVLD VPEGTLPDKQ
        210        220        230        240        250
   STEQAIQLLE KMKTSASPFF LAVGYHKPHI PFRYPKEFQK LYPLE▓ITLA
        260        270        280        290        300
   PDPEVPDGLP PVAYNPWMDI RQREDVQAL▓ ISVPYGPIPV DFQRKIRQSY
        310        320        330        340        350
   FASVSYLDTQ VGRLLSALDD LQLA▓STIIA FTSDHGWALG EHGEWAKYSN
        360        370        380        390        400
   FDVATHVPLI FYVPGRTASL PEAGEKLFPY LDPFDSASQL MEPGRQSMDL
        410        420        430        440        450
   VELVSLFPTL AGLAGLQVPP RCPVPSFHVE LCRECGKNLLK HFRFRDLEED
   →Mature 14kD
        460        470        480        490        500
   PYLPGNPREL IAYSQYPRPS DIPQWNSDKP SLKDIKIMGY SIRTIDYRYT
        510        520        530        540        550
   VWVGFNPDEF LA▓FSDIHAG ELYFVDSDPL QDHNMY▓DSQ GGDLFQLLMP  (SEQ ID NO: 1)
```

*Italics* = signal sequence (*MPPPRTGRGL LWLGLVLSSV CVALG*) (SEQ ID NO: 48)

▓ = N-linked glycosylation sites (GlcNac...)

Boxed = Y-sulfation site (PSSEKYENTKTCRGPD) SEQ ID NO: 45

Underscore = amino-terminal sequence of 42kD and 14 kD peptides (Sleat 2005)

$C^{84}$ = formylglycine modification $N^{280}$ = M-6-P residue(s)

FIG. 1

CLUSTAL O(1.2.4) multiple sequence alignment of hIDS to orhologs

```
SP|P22304|IDS_HUMAN                  MPPPRTGRGLLWLGLVLSSVCVALGSETQANSTTDALNVLLIIVDDLRPSLGCYGDKLVR 60
TR|K6ZGI9|K6ZGI9_PANTR               MPPPRTGRGLPWLGLVLSSVCVALGSETQANSTTDALNVLLIIVDDLRPSLGCYGDKLVR 60
TR|K7BKV4|K7BKV4_PANTR               MPPPRTGRGLPWLGLVLSSVCVALGSETQANSTTDALNVLLIIVDDLRPSLGCYGDKLVR 60
TR|H9FTX2|H9FTX2_MACMU               MPTPGSGRGFLWLGLVLSSVCVALGCETQANSTTDALNILLIIVDDLRPSLGCYGDKLVR 60
TR|F7EJG2|F7EJG2_CALJA               MPPPRTSRCLLLLGLVLGSVCVTLGSQAQASSTTDALNVLLIIVDDLRPSLGCYGDKLVR 60
TR|U3DTL8|U3DTL8_CALJA               MPPPRPSRCLLLLGLVLGSVCVTLGSQAQANSTTDALNVLLIIVDDLRPSLGCYGDKLVR 60
TR|G7NRX7|G7NRX7_MACMU               MPTPGSGRGFLWLGLVLSSVCVALGCETQANSTTDALNILLIIVDDLRPSLGCYGDKLVR 60
TR|G7Q1V9|G7Q1V9_MACFA               MPTPGSGRGFLWLGLVLSSVCVALGCETQANSTTDALNILLIIVDDLRPSLGCYGDKLVR 60
TR|H2PX10|H2PX10_PONAB               MPPPRTGRGLLWLGLVLSSVCVALGSETQADSTTDGLNVLLIIVDDLRPSLGCYGDKLVR 60
TR|A0A0D9R4D1|A0A0D9R4D1_CHLSB       MPTPGSGRGFLWLGLVLSSVCVALGSETQANSTTDALNILLIIVDDLRPSLGCYGDKLVR 60
TR|G1RST8|G1RST8_NOMLE               MSPPRTGQGLLWLGVVLSSVCVAXVTSPKPPSFVDALNVLLIIVDDLRPSLGCYGDKLVR 60
UPI0000D9F625                        MPTPGSGRGFLWLGLVLSSVCVALGCETQANSTTDALNILLIIVDDLRPSLGCYGDKLVR 60
UPI000274358B                        MPPPRTGRGLLWLGLVLSSVCVALGSETQANSTTDALNVLLIIVDDLRPSLGCYGDKLVR 60
UPI00027F6FC5                        MPTPGSGRGFLWLGLVLSSVCVALGCEMQANSTTDALNILLIIVDDLRPSLGCYGDKLVR 60
UPI00027FAE03                        MPPPRTGLCLLLLGLVLGSVCVTLGSQAQANSTTDALNVLLIIVDDLRPSLGCYGDKLVR 60
UPI0003ABBF28                        MPTPGSGRGFLWLGLVLSSVCVALGCETQANSTTDALNILLIIVDDLRPSLGCYGDKLVR 60
UPI000533297F                        MPTPASGRGFLWLGLVLSSVCVALGSETQANSTTDALNILLIIVDDLRPSLGCYGDKLVR 60
UPI0005F40BD2                        MPTPASGRGFLWLGLVLRSVCVALGSETQANSTTDALNILLIIVDDLRPSLGCYGDKLVR 60
                                      *  *   :  **:** ****:     . :  * .*.**:********************

SP|P22304|IDS_HUMAN                  SPNIDQLASHSLLFQNAFAQQAVCAPSRVSFLTGRRPDTTRLYDFNSYWRVHAGNFSTIP 120
TR|K6ZGI9|K6ZGI9_PANTR               SPNIDQLASHSLLFQNAFAQQAVCAPSRVSFLTGRRPDPTRLYDFNSYWRVHAGNFSTIP 120
TR|K7BKV4|K7BKV4_PANTR               SPNIDQLASHSLLFQNAFAQQAVCAPSRVSFLTGRRPDTTRLYDFNSYWRVHAGNFSTIP 120
TR|H9FTX2|H9FTX2_MACMU               SPNIDQLASHSLLFQNAFAQQAVCAPSRVSFLTGRRPDTTRLYDFNSYWRVHAGNFSTIP 120
TR|F7EJG2|F7EJG2_CALJA               SPNIDQLASHSLLFQNAFAQQAVCAPSRVSFLTGRRPDTTRLYDFNSYWRVHAGNFSTIP 120
TR|U3DTL8|U3DTL8_CALJA               SPNIDQLASHSLLFQNAFAQQAVCAPSRVSFLTGRRPDTTRLYDFNSYWRVHAGNFSTIP 120
TR|G7NRX7|G7NRX7_MACMU               SPNIDQLASHSLLFQNAFAQQAVCAPSRVSFLTGRRPDTTRLYDFNSYWRVHAGNFSTIP 120
TR|G7Q1V9|G7Q1V9_MACFA               SPNIDQLASHSLLFQNAFAQQAVCAPSRVSFLTGRRPDTTRLYDFNSYWRVHAGNFSTIP 120
TR|H2PX10|H2PX10_PONAB               SPNIDQLASHSLLFQNAFAQQAVCAPSRVSFLTGRRPDTTRLYDFNSYWRVHAGNFSTIP 120
TR|A0A0D9R4D1|A0A0D9R4D1_CHLSB       SPNIDQLASHSLLFQNAFAQQAVCAPSRVSFLTGRRPDTTRLHNFNSYWRVHAGNFSTIP 120
TR|G1RST8|G1RST8_NOMLE               SPNIDQLASHSLLFQNAFAQQAVCAPSRVSFLTGRRPDTTRLYDFNSYWRVHAGNFSTIP 120
UPI0000D9F625                        SPNIDQLASHSLLFQNAFAQQAVCAPSRVSFLTGRRPDTTRLYDFNSYWRVHAGNFSTIP 120
UPI000274358B                        SPNIDQLASHSLLFQNAFAQQAVCAPSRVSFLTGRRPDTTRLYDFNSYWRVHAGNFSTIP 120
UPI00027F6FC5                        SPNIDQLASHSLLFQNAFAQQAVCAPSRVSFLTGRRPDTTRLYDFNSYWRVHAGNFSTIP 120
UPI00027FAE03                        SPNIDQLASHSLLFQNAFVQQAVCAPSRVSFLTGRRPDTTRLYDFNSYWRVHAGNFSTIP 120
UPI0003ABBF28                        SPNIDQLASHSLLFQNAFAQEAVCAPSRVSFLTGRRPDTTRLYDFNSYWRVHAGNFSTIP 120
UPI000533297F                        SPNIDQLASHSLLFQNAFAQQAVCAPSRVSFLTGRRPDTTRLYDFNSYWRVHAGNFSTIP 120
UPI0005F40BD2                        SPNIDQLASHSLLFQNAFAQQAVCTPSHVSFLTGRRPDTTRLYDFNSYWRVHAGNFSTIP 120
                                     *****************.*:***:**.**********  ***.:*************

SP|P22304|IDS_HUMAN                  QYFKENGYVTMSVGKVFHPGISSNHTDDSPYSWSFPPYHPSSEKYENTKTCRGPDGELHA 180
TR|K6ZGI9|K6ZGI9_PANTR               QYFKENGYVTMSVGKVFHPGISSNHTDDSPYSWSFPPYHPSSEKYENTKTCRGPDGELHA 180
TR|K7BKV4|K7BKV4_PANTR               QYFKENGYVTMSVGKVFHPGISSNHTDDSPYSWSFPPYHPSSEKYENTKTCRGPDGELHA 180
TR|H9FTX2|H9FTX2_MACMU               QYFKENGYVTMSVGKVFHPGITSNHTDDSPYSWSFPPYHPSSEKYENTKTCRGPDGELHA 180
TR|F7EJG2|F7EJG2_CALJA               QYFKDNGYVTMSVGKVFHPGISSNHSDDSPYSWSFPPYHPSSEKYENTKTCRGPDGELHA 180
TR|U3DTL8|U3DTL8_CALJA               QYFKDNGYVTMSVGKVFHPGISSNHSDDSPYSWSFPPYHPSSEKYENTKTCRGPDGELHA 180
TR|G7NRX7|G7NRX7_MACMU               QYFKENGYVTMSVGKVFHPGITSNHTDDSPYSWSFPPYHPSSEKYENTKTCRGPDGELHA 180
TR|G7Q1V9|G7Q1V9_MACFA               QYFKENGYVTMSVGKVFHPGITSNHTDDSPYSWSFPPYHPSSEKYENTKTCRGPDGELHA 180
TR|H2PX10|H2PX10_PONAB               QYFKENGYVTMSVGKVFHPGISSNHTDDSPYSWSFPPYHPSSEKYENTKTCRGPDGELHA 180
TR|A0A0D9R4D1|A0A0D9R4D1_CHLSB       QYFKENGYVTMSVGKVFHPGITSNHTDDSPYSWSFPPYHPSSEKYENTKTCRGPDGELHA 180
TR|G1RST8|G1RST8_NOMLE               QYFKENGYVTMSVGKVFHPGITSSNHTDDSPYSWSFPPYHPSSXXXXXXKTCRGPDGELHA 180
UPI0000D9F625                        QYFKENGYVTMSVGKVFHPGITSNHTDDSPYSWSFPPYHPSSEKYENTKTCRGPDGELHA 180
UPI000274358B                        QYFKENGYVTMSVGKVFHPGISSNHTDDSPYSWSFPPYHPSSEKYENTKTCRGPDGELHA 180
UPI00027F6FC5                        QYFKENGYVTMSVGKVFHPGITSNHTDDSPYSWSFPPYHPSSEKYENTKTCRGPDGELHA 180
UPI00027FAE03                        QYFKDNGYVTMSVGKVFHPGISSNHSDDSPYSWSFPPYHPSSEKYENTKTCRGPDGELHA 180
UPI0003ABBF28                        QYFKENGYVTMSVGKVFHPGITSNHTDDSPYSWSFPPYHPSSEKYENTKTCRGPDGELHA 180
UPI000533297F                        QYFKENGYVTMSVGKVFHPGITSNHTDDSPYSWSFPPYHPSSEKYENTKTCRGPDGELHA 180
UPI0005F40BD2                        QYFKENGYVTMSVGKVFHPGITSNHTDDSPYSWSFPPYHPSSEKYENTKTCRGPDGELHA 180
                                     ****:*************** *:.***:********************             ***********
```

FIG. 2

```
SP|P22304|IDS_HUMAN                    NLLCPVDVLDVPEGTLPDKQSTEQAIQLLEKMKTSASPFFLAVGYHKPHIPFRYPKEFQK 240
TR|K6ZGI9|K6ZGI9_PANTR                 NLLCPVDVLDVPEGTLPDKQSTEQAIQLLEKMKTSASPFFLAVGYHKPHIPFRYPKEFQK 240
TR|K7BKV4|K7BKV4_PANTR                 NLLCPVDVLDVPEGTLPDKQSTEQAIQLLEKMKTSASPFFLAVGYHKPHIPFRYPKEFQK 240
TR|H9FTX2|H9FTX2_MACMU                 NLLCPVDVVDVPEGTLPDKQSTEQAIQLLEKMKTSASPFFLAVGYHKPHIPFRYPKEFQK 240
TR|F7EJG2|F7EJG2_CALJA                 NLLCPVDVVDVPEGTLPDKQSTEEAIRLLEKMKTSASPFFLAVGYHKPHIPFRYPKEFQK 240
TR|U3DTL8|U3DTL8_CALJA                 NLLCPVDVVDVPEGTLPDKQSTEEAIRLLEKMKTSASPFFLAVGYHKPHIPFRYPKEFQK 240
TR|G7NRX7|G7NRX7_MACMU                 NLLCPVDVVDVPEGTLPDKQSTEQAIQLLEKMKTSASPFFLAVGYHKPHIPFRYPKEFQK 240
TR|G7Q1V9|G7Q1V9_MACFA                 NLLCPVDVVDVPEGTLPDKQSTEQAIQLLEKMKTSASPFFLAVGYHKPHIPFRYPKEFQK 240
TR|H2PX10|H2PX10_PONAB                 NLIAKKMCWMFPRAPCCDKQSTEQAIQLLEKMKTSASPFFLAVGYHKPHIPFRYPKEFQK 240
TR|A0A0D9R4D1|A0A0D9R4D1_CHLSB         NLLCPVDVVDVPEGTLPDKQSTEQAIQLLEKMKTSASPFFLAVGYHKPHIPFRYPKEFQK 240
TR|G1RST8|G1RST8_NOMLE                 NLLCPVDVLDVPEGTLPDKQSTEQAIQLLEKMKTSASPFFLAVGYHKPHIPFRYPKEFQK 240
UPI0000D9F625                          NLLCPVDVVDVPEGTLPDKQSTEQAIQLLEKMKTSASPFFLAVGYHKPHIPFRYPKEFQK 240
UPI000274358B                          NLLCPVDVLDVPEGTLPDKQSTEQAIRLLEKMKTSASPFFLAVGYHKPHIPFRYPKEFQK 240
UPI00027F6FC5                          NLLCPVDVVDVPEGTLPDKQSTEQAIQLLEKMKTSASPFFLAVGYHKPHIPFRYPKEFQK 240
UPI00027FAE03                          NLLCPVDVVDVPEGTLPDKQSTEEAIRLLKKMKTSASPFFLAVGYHKPHIPFRYPKEFQK 240
UPI0003ABBF28                          NLLCPVDVVDVPEGTLPDKQSTEQAIQLLEKMKTSASPFFLAVGYHKPHIPFRYPKEFQK 240
UPI000533297F                          NLLCPVDVVDVPEGTLPDKQSTEQAVQLLEKMKTSASPFFLAVGYHKPHIPFRYPKEFQK 240
UPI0005F40BD2                          NLLCPVDVVDVPEGTLPDKQSTEQAIQLLEKMKTSASPFFLAVGYHKPHIPFRYPKEFQK 240
                                       **:.       .*..   ******:*::**:*****************************

SP|P22304|IDS_HUMAN                    LYPLENITLAPDPEVPDGLPPVAYNPWMDIRQREDVQALNISVPYGPIPVDFQRKIRQSY 300
TR|K6ZGI9|K6ZGI9_PANTR                 LYPLENITLAPDPEVPDGLPPVAYNPWMDIRQREDVQALNISVPYGPIPVDFQRKIRQSY 300
TR|K7BKV4|K7BKV4_PANTR                 LYPLENITLAPDPEVPDGLPPVAYNPWMDIRQREDVQALNISVPYGPIPVDFQRKIRQSY 300
TR|H9FTX2|H9FTX2_MACMU                 LYPLENITLAPDSEVPDGLPPVAYNPWMDIRQREDVQALNISVPYGPIPVEFQRKIRQSY 300
TR|F7EJG2|F7EJG2_CALJA                 LYPLENITLAPDPEVPDGLPPVAYNPWMDIRQREDVQALNISVPYGPIPVDFQRKIRQSY 300
TR|U3DTL8|U3DTL8_CALJA                 LYPLENITLAPDPEVPDGLPPVAYNPWMDIRQREDVQALNISVPYGPIPVDFQRKIRQSY 300
TR|G7NRX7|G7NRX7_MACMU                 LYPLENITLAPDSEVPDGLPPVAYNPWMDIRQREDVQALNISVPYGPIPVEFQRKIRQSY 300
TR|G7Q1V9|G7Q1V9_MACFA                 LYPLENITLAPDSEVPDGLPPVAYNPWMDIRQREDVQALNISVPYGPIPVEFQRKIRQSY 300
TR|H2PX10|H2PX10_PONAB                 LYPLENITLAPDPEVPDGLPPVAYNPWMDIRQREDVQALNISVPYGPIPVDFQQKIRQSY 300
TR|A0A0D9R4D1|A0A0D9R4D1_CHLSB         LYPLENITLAPDSEVPDGLPPVAYNPWMDIRQREDVQALNISVPYGPIPVEFQRKIRQSY 300
TR|G1RST8|G1RST8_NOMLE                 LYPLENITLAPDSEVPDGLPPVAYNPWMDIRQREDVQALNISVPYGPIPVDFQRKIRQSY 300
UPI0000D9F625                          LYPLENITLAPDSEVPDGLPPVAYNPWMDIRQREDVQALNISVPYGPIPVEFQRKIRQSY 300
UPI000274358B                          LYPLENITLAPDPEVPDGLPPVAYNPWMDIRQREDVQALNISVPYGPIPVDFQRKIRQSY 300
UPI00027F6FC5                          LYPLENITLAPDSEVPDGLPPVAYNPWMDIRQREDVQALNISVPYGPIPVEFQRKIRQSY 300
UPI00027FAE03                          LYPLENITLAPDPEVPDGLPPVAYNPWMDIRQREDVQALNISVPYGPIPVDFQRKIRQSY 300
UPI0003ABBF28                          LYPLENITLAPDSEVPDGLPPVAYNPWMDIRQREDVQALNISVPYGPIPVEFQRKIRQSY 300
UPI000533297F                          LYPLENITLAPDSEVPDGLPPVAYNPWMDIRQREDVQALNISVPYGPIPVDFQRKIRQSY 300
UPI0005F40BD2                          LYPLENITLAPDSEVPDGLPPVAYNPWMDIRQREDVQALNISVPYGPIPVDFQRKIRQSY 300
                                       ************ *****************************************:**:******

SP|P22304|IDS_HUMAN                    FASVSYLDTQVGRLLSALDDLQLANSTIIAFTSDHGWALGEHGEWAKYSNFDVATHVPLI 360
TR|K6ZGI9|K6ZGI9_PANTR                 FASVSYLDTQVGRLLSALDDLQLANSTIIAFTSDHGWALGEHGEWAKYSNFDVATHVPLM 360
TR|K7BKV4|K7BKV4_PANTR                 FASVSYLDTQVGRLLSALDDLQLANSTIIAFTSDHGWALGEHGEWAKYSNFDVATHVPLM 360
TR|H9FTX2|H9FTX2_MACMU                 FASVSYLDTQVGRLLSALDDLQLANSTIVAFTSDHGWALGEHGEWAKYSNFDVATHVPLM 360
TR|F7EJG2|F7EJG2_CALJA                 FASVSYLDTQVGRLLSALDDLQLANSTIVAFTSDHGWALGEHGEWAKYSNFDVATRVPLM 360
TR|U3DTL8|U3DTL8_CALJA                 FASVSYLDTQVGHLLSALDDLQLANSTIVAFTSDHGWALGEHGEWAKYSNFDVATRVPLM 360
TR|G7NRX7|G7NRX7_MACMU                 FASVSYLDTQVGRLLSALDDLQLANSTIVAFTSDHGWALGEHGEWAKYSNFDVATHVPLM 360
TR|G7Q1V9|G7Q1V9_MACFA                 FASVSYLDTQVGHLLSALDDLQLANSTIVAFTSDHGWALGEHGEWAKYSNFDVATHVPLM 360
TR|H2PX10|H2PX10_PONAB                 FASVSYLDTQVGRLLSTLDDLQLANSTIIAFTSDHGWALGEHGEWAKYSNFDVATHVPLM 360
TR|A0A0D9R4D1|A0A0D9R4D1_CHLSB         FASVSYLDTQVGRLLSALDDLQLANSTIVAFTSDHGWALGEHGEWAKYSNFDVATHVPLM 360
TR|G1RST8|G1RST8_NOMLE                 FASVSYLDTQVGRLLSALDDLQLANSTIIAFTSDHGWALGEHGEWAKYSNFDVATHVPLM 360
UPI0000D9F625                          FASVSYLDTQVGHLLSALDDLQLANSTIVAFTSDHGWALGEHGEWAKYSNFDVATHVPLM 360
UPI000274358B                          FASVSYLDTQVGRLLSALDDLQLANSTIIAFTSDHGWALGEHGEWAKYSNFDVATHVPLM 360
UPI00027F6FC5                          FASVSYLDTQVGRLLSALDDLQLANSTIVAFTSDHGWALGEHGEWAKYSNFDVATHVPLM 360
UPI00027FAE03                          FASVSYLDTQVGHLLSALDDLHLANSTIVAFTSDHGWALGEHGEWAKYSNFDVATRVPLM 360
UPI0003ABBF28                          FASVSYLDTQVGRLLSALDDLQLANSTIVAFTSDHGWALGEHGEWAKYSNFDVATHVPLM 360
UPI000533297F                          FASVSYLDTQVGRLLSALDDLQLANSTIVAFTSDHGWALGEHGEWAKYSNFDVATHVPLM 360
UPI0005F40BD2                          FASVSYLDTQVGHLLSALDDLQLANSTIVAFTSDHGWALGEHGEWAKYSNFDVATHVPLM 360
                                       ************:***:***:******:***************************:***:
```

FIG. 2 continued

```
SP|P22304|IDS_HUMAN                  FYVPGRTASLPEAGEKLFPYLDPFDSASQLMEPGRQSMDLVELVSLFPTLAGLAGLQVPP 420
TR|K6ZGI9|K6ZGI9_PANTR               FYVPGRTASLPEAGEKLFPYLDPFDSASQLMEPGRQSMDLVELVSLFPTLAGLAGLQAPP 420
TR|K7BKV4|K7BKV4_PANTR               FYVPGRTASLPEAGEKLFPYLDPFDSASQLMEPGRQSMDLVELVSLFPTLAGLAGLQAPP 420
TR|H9FTX2|H9FTX2_MACMU               FYVPGRTASLPEAGEKLFPYLDPFDSASELMEPGRQSMDLVELVSLFPTLAGLAGLQVPP 420
TR|F7EJG2|F7EJG2_CALJA               FYVPGRTASLPEADEKLFPYVDPFHSASELMEPGRQSMDLVELVSLFPTLAGLAGLQVPP 420
TR|U3DTL8|U3DTL8_CALJA               FYVPGRTASLPEADEKLFPYVDPFHSASELMEPGRQSMDLVELVSLFPTLAGLAGLQVPP 420
TR|G7NRX7|G7NRX7_MACMU               FYVPGRTASLPEAGEKLFPYLDPFDSASELMEPGRQSMDLVELVSLFPTLAGLAGLQVPP 420
TR|G7Q1V9|G7Q1V9_MACFA               FYVPGRTASLPEAGEKLFPYLDPFDSASELMEPGRQSMDLVELVSLFPTLAGLAGLQVPP 420
TR|H2PX10|H2PX10_PONAB               FYVPGRTASLPEAGEKLFPYLDPFDSASELMEPGRQSMDLVELVSLFPTLAGLAGLQVPP 420
TR|A0A0D9R4D1|A0A0D9R4D1_CHLSB       FYVPGRTASLPEAGEKLFPYLDPFDSASELMEPGRQSMDLVELVSLFPTLAGLAGLQVPP 420
TR|G1RST8|G1RST8_NOMLE               FYVPGRTASLPEAGEKLFPYLDPFDSASELMEPGRQSMDLVELVSLFPTLAGLAGLQVPP 420
UPI0000D9F625                        FYVPGRTASLPEAGEKLFPYLDPFDSASELMEPGRQSMDLVELVSLFPTLAGLAGLQVPP 420
UPI000274358B                        FYVPGRTASLPEAGEKLFPYLDPFDSASQLMEPGRQSMDLVELVSLFPTLAGLAGLQVPP 420
UPI00027F6FC5                        FYVPGRTASLPEAGEKLFPYLDPFDSASELMEPGRQSMDLVELVSLFPTLAGLAGLQVPP 420
UPI00027FAE03                        FYVPGRTASLPETGEKLFPYVDPFHSASELMEPGRQSTDLVELVSLFPTLAGLAGLQVPP 420
UPI0003ABBF28                        FYVPGRTASLPEAGEKLFPYLDPFDSASELMEPGRQSMDLVELVSLFPTLAGLAGLQVPP 420
UPI000533297F                        FYVPGRTASLPEAGEKLFPYLDPFDSASELMEPGRQSMDLVELVSLFPTLAGLAGLQVPP 420
UPI0005F40BD2                        FYVPGRTASLPEAGEKLFPYLDPFDSASELMEPGRQSMDLVELVSLFPTLAGLAGLQVPP 420
                                     **********:.******:***.***:******* ******************.**

SP|P22304|IDS_HUMAN                  RCPVPSFHVELCREGKNLLKHFRFRDLEEDPYLPGNPRELIAYSQYPRPSDIPQWNSDKP 480
TR|K6ZGI9|K6ZGI9_PANTR               RCPVPSFHVELCREGKNLLKHFRFRDLEEDPYLPGNPRELIAYSQYPRPSDIPQWNSDKP 480
TR|K7BKV4|K7BKV4_PANTR               RCPVPSFHVELCREGKNLLKHFRFRDLEEDPYLPGNPRELIAYSQYPRPSDIPQWNSDKP 480
TR|H9FTX2|H9FTX2_MACMU               RCPVPSFHVELCREGKNLLKHFRFRDLEEDPYLPGNPRELIAYSQYPRPADFPQWNSDKP 480
TR|F7EJG2|F7EJG2_CALJA               RCPVPSFHVELCREGKSLLKHFRFHGLEEDPYLPGNPRELIAYSQYPRPADFPQWNSDKP 480
TR|U3DTL8|U3DTL8_CALJA               RCPVPSFHVELCREGKSLLKHFRFHGLEEDPYLPGNPRELIAYSQYPRPADFPQWNSDKP 480
TR|G7NRX7|G7NRX7_MACMU               RCPVPSFHVELCREGKNLLKHFRFRDLEEDPYLPGNPRELIAYSQYPRPADFPQWNSDKP 480
TR|G7Q1V9|G7Q1V9_MACFA               RCPVPSFHVELCREGKNLLKHFRFRDLEEDPYLPGNPRELIAYSQYPRPADFPQWNSDKP 480
TR|H2PX10|H2PX10_PONAB               RCPVPSFHVELCREGKNLLKHFRFRDLEEDPYLPGNPRELIAYSQYPRPADIPQWNSDKP 480
TR|A0A0D9R4D1|A0A0D9R4D1_CHLSB       RCPVPSFHVELCREGKNLLKHFRFRDLEEDPYLPGNPRELIAYSQYPRPADFPQWNSDKP 480
TR|G1RST8|G1RST8_NOMLE               RCPVPSFHVELCREGKNLLKHFRFRDLEEDPYLPGNPRELIAYSQYPRPADIPQWNSDKP 480
UPI0000D9F625                        RCPVPSFHVELCREGKNLLKHFRFRDLEEDPYLPGNPRELIAYSQYPRPADFPQWNSDKP 480
UPI000274358B                        RCPVPSFHVELCREGKNLLKHFRFRDLEEDPYLPGNPRELIAYSQYPRPSDIPQWNSDKP 480
UPI00027F6FC5                        RCPVPSFHVELCREGKNLLKHFRFRDLEEDPYLPGNPRELIAYSQYPRPADFPQWNSDKP 480
UPI00027FAE03                        RCPVPSFHIELCREGKNLLKHFRFHGLEEDPYLPGNPRELIAYSQYPRPADFPQQNSDKP 480
UPI0003ABBF28                        RCPVPSFHVELCREGKNLLKHFRFRDLEEDPYLPGNPRELIAYSQYPRPADFPQWNSDKP 480
UPI000533297F                        RCPVPSFHVELCREGKNLLKHFRFRDLEEDPYLPGNPRELIAYSQYPRPADFPQWNSDKP 480
UPI0005F40BD2                        RCPVPSFHVELCREGKNLLKHFRFRDLEEDPYLPGNPRELIAYSQYPRPADFPQWNSDKP 480
                                     ********:*******.******:.*********************:.:** *****

SP|P22304|IDS_HUMAN                  SLKDIKIMGYSIRTIDYRYTVWVGFNPDEFLANFSDIHAGELYFVDSDPLQDHNMYNDSQ 540
TR|K6ZGI9|K6ZGI9_PANTR               SLKDIKIMGYSIRTIDYRYTVWIGFNPDEFLANFSDIHAGELYFVDSDPLQDHNMYNDSQ 540
TR|K7BKV4|K7BKV4_PANTR               SLKDIKIMGYSIRTIDYRYTVWIGFNPDEFLANFSDIHAGELYFVDSDPLQDHNMYNDSQ 540
TR|H9FTX2|H9FTX2_MACMU               SLKDIKIMGYSIRTIDYRYTVWVGFNPDEFLANFSDIHAGELYFVDSDPLQDHNMYNDSQ 540
TR|F7EJG2|F7EJG2_CALJA               SLKYIKIMGYSIRTVDYRYTVWVGFNPDEFLANFSDIHAGELYFVDSDPLQDHNMYNDSQ 540
TR|U3DTL8|U3DTL8_CALJA               SLKYIKIMGYSIRTVDYRYTVWVGFNPDEFLANFSDIHAGELYFVDSDPLQDHNMYNDSQ 540
TR|G7NRX7|G7NRX7_MACMU               SLKDIKIMGYSIRTIDYRYTVWVGFNPDEFLANFSDIHAGELYFVDSDPLQDHNMYNDSQ 540
TR|G7Q1V9|G7Q1V9_MACFA               SLKDIKIMGYSIRTIDYRYTVWVGFNPDEFLANFSDIHAGELYFVDSDPLQDHNMYNDSQ 540
TR|H2PX10|H2PX10_PONAB               SLKDIKIMGYSIRTIDYRYTVWVGFNPDEFLANFSDIHAGELYFVDSDPLQDHNMYNDSQ 540
TR|A0A0D9R4D1|A0A0D9R4D1_CHLSB       NLKDIKIMGYSIRTIDYRYTVWVGFNPDEFLANFSDIHAGELYFVDSDPLQDHNMYNDSQ 540
TR|G1RST8|G1RST8_NOMLE               SLKDIKIMGYSIRTIDYRYTVWVGFSPDEFLANFSDIHAGELYFVDSDPLQDHNMYNDSQ 540
UPI0000D9F625                        SLKDIKIMGYSIRTIDYRYTVWVGFNPDEFLANFSDIHAGELYFVDSDPLQDHNMYNDSQ 540
UPI000274358B                        SLKDIKIMGYSIRTIDYRYTVWVGFNPDEFLANFSDIHAGELYFVDSDPLQDHNMYNDSQ 540
UPI00027F6FC5                        SLKDIKIMGYSIRTIDYRYTVWVGFNPDEFLANFSDIHAGELYFVDSDPLQDHNMYNDSQ 540
UPI00027FAE03                        SLKYIKIMGYSIRTVDYRYTVWVGFNPDEFLANFSDIHAGELYFVDSDPLQDHNMYNDSQ 540
UPI0003ABBF28                        SLKDIKIMGYSIRTIDYRYTVWVGFNPDEFLANFSDIHAGELYFVDSDPLQDHNMYNDSQ 540
UPI000533297F                        SLKDIKIMGYSIRTIDYRYTVWVGFNPDEFLANFSDIHAGELYFVDSDPFQDHNMYNDSQ 540
UPI0005F40BD2                        SLKDIKIMGYSIRTIDYRYTVWVGFNPDEFLANFSDIHAGELYFVDSDPLQDHNMYNDSQ 540
                                     .** *********:******:**.*************************:**********
```

FIG. 2 continued

```
SP|P22304|IDS_HUMAN              GGDLFQLLMP  550
TR|K6ZGI9|K6ZGI9_PANTR           GGDLFQLLMP  550
TR|K7BKV4|K7BKV4_PANTR           GGDLFQLLMP  550
TR|H9FTX2|H9FTX2_MACMU           GGDLFQLLMP  550
TR|F7EJG2|F7EJG2_CALJA           GGELFQSLMP  550
TR|U3DTL8|U3DTL8_CALJA           GGELFQSLMP  550
TR|G7NRX7|G7NRX7_MACMU           GGDLLQLLMP  550
TR|G7Q1V9|G7Q1V9_MACFA           GGDLFQLLMP  550
TR|H2PX10|H2PX10_PONAB           GGDLFQLLMP  550
TR|A0A0D9R4D1|A0A0D9R4D1_CHLSB   GGDLFQLLMP  550
TR|G1RST8|G1RST8_NOMLE           GGDLFQLLMP  550
UPI0000D9F625                    GGDLLQLLMP  550
UPI000274358B                    GGDLFQLLMP  550
UPI00027F6FC5                    GGDLFQLLMP  550
UPI00027FAE03                    GGELFQSLMP  550
UPI0003ABBF28                    GGDLFQLLMP  550
UPI000533297F                    GGDLFQLLMP  550
UPI0005F40BD2                    GGDLFQLLMP  550
                                 **:*:* ***
```

Species Legend:
```
SP|P22304|IDS_HUMAN              [Homo sapiens]
TR|K6ZGI9|K6ZGI9_PANTR           [Pan troglodytes (Chimpanzee)]
TR|K7BKV4|K7BKV4_PANTR           [Pan troglodytes (Chimpanzee)]
TR|H9FTX2|H9FTX2_MACMU           [Macaca mulatta (Rhesus macaque)]
TR|F7EJG2|F7EJG2_CALJA           [Callithrix jacchus (White-tufted-ear marmoset)]
TR|U3DTL8|U3DTL8_CALJA           [Callithrix jacchus (White-tufted-ear marmoset)]
TR|G7NRX7|G7NRX7_MACMU           [Macaca mulatta (Rhesus macaque)]
TR|G7Q1V9|G7Q1V9_MACFA           [Macaca fascicularis (Crab-eating macaque; Cynomologous monkey)]
TR|H2PX10|H2PX10_PONAB           [Pongo abelii (Sumatran orangutan)]
TR|A0A0D9R4D1_CHLSB              [Chlorocebus sabaeus (Green monkey)]
TR|G1RST8|G1RST8_NOMLE           [Nomascus leucogenys (Northern white-cheeked gibbon)]
UPI0000D9F625                    [Macaca mulatta (Rhesus macaque)]
UPI000274358B                    [Pan paniscus (Pygmy chimpanzee; Bonobo)]
UPI00027F6FC5                    [Papio Anubis (Olive baboon)]
UPI00027FAE03                    [Saimiri boliviensis (Bolivian squirrel monkey)]
UPI0003ABBF28                    [Macaca fascicularis (Crab-eating macaque; Cynomologous monkey)]
UPI000533297F                    [Rhinopithecus roxellana (Golden snub-nosed monkey; Pygathrix roxellana)]
UPI0005F40BD2                    [Colobus angolensis palliates (Peters' Angolan colobus)]
```

FIG. 2 continued

| | | |
|---|---|---|
| L41P (mild); | E125V (mild); | D334G (severe); |
| 41X (intermediate); | S132W (severe); | D334N (mild); |
| D45N (MPS2); | G134R (severe); | H335R (intermediate); |
| R48P (mild); | K135N (intermediate); | G336E (severe); |
| Y54D (severe); | K135R (intermediate); | G336R (severe); |
| N63D (mild/intermediate); | H138D (mild/intermediate); | W337R (intermediate); |
| A68E (severe); | G140V (MPS2; no significant enzyme activity); | L339R (severe); |
| S71N (mild); | | G340D (mild); |
| S71R (severe); | S143F (MPS2); | E341K (severe); |
| L73F (severe); | D148H (intermediate); | H342Y (mild); |
| A79E (mild); | H159P (severe); | W345C (mild/severe); |
| A82E (MPS2); | 159X (missing in MPS2; intermediate form; | A346D (mild/severe); |
| A82V (no significant enzyme activity); | | A346V (mild/severe); |
| | P160R (MPS2); | K347I (MPS2); |
| A85S (severe); | N181I (mild); | K347Q (severe); |
| A85T (mild to severe forms); | L182P (intermediate); | K347T (severe); |
| P86L (intermediate to severe forms); | C184F (mild/intermediate); | Y348H (MPS2); |
| | C184W (MPS2); | S349I (severe); |
| P86Q (MPS2); | L196S (mild/intermediate); | P358R (severe); |
| P86R (severe); | D198G (mild); | L403R (intermediate); |
| S87N (mild); | A205P (intermediate); | L410P (MPS2); |
| R88C (severe); | L221P (intermediate); | C422G (mild); |
| R88G (severe); | G224E (severe); | C422R (severe); |
| R88H (intermediate/severe form); | Y225D (intermediate); | C432Y (severe); |
| R88L (severe); | K227M (intermediate); | E434K (MPS2); |
| R88P (severe – total absence of residual activity); | K227Q (severe); | Q465P (severe); |
| | P228L (MPS2); | P467L (severe); |
| V89F (MPS2); | P228T (severe); | R468G (mild/severe); |
| L92P (severe); | H229R (intermediate/severe); | R468L (mild/severe); |
| G94D (mild); | H229Y (severe); | R468Q (severe/intermediate; greatly reduced activity); |
| R95G (intermediate); | P231L (mild); | |
| R95T (mild); | D252N (MPS2); | R468W (mild/severe); |
| 95X (severe); | L259P (severe); | P469H (mild); |
| L102R (mild); | Y264N (MPS2); | D478G (mild); |
| Y108C (mild); | N265I (intermediate; deleterious mutation); | D478Y (severe); |
| Y108S (mild); | | P480L (mild); |
| N115Y (MPS2); | P266H (mild); | P480Q (mild); |
| S117Y (severe); | P266R (MPS2); | P480R (severe); |
| 117X (missing in MPS2; severe form; deleterious mutation); | D269V (MPS2); | I485K (MPS2); |
| | Q293H (mild); | I485R (severe); |
| T118I (mild to severe; greatly reduced activity); | S299I (mild); | MG488 – 489IA (intermediate); |
| | D308E (mild); | Y490S (intermediate); |
| 118X (missing in MPS2; severe form); | D308N (intermediate); | S491F (mild); |
| | T309A (severe); | W502C (severe); |
| P120H (mild); | R313C (MPS2; unknown pathological significance); | W502S (MPS2); |
| P120R (severe); | | E521K (severe); |
| Q121H (severe); | L314P (severe); | E521V (severe); |
| Q121R (severe); | S333L (severe); | Y523C (mild). |

FIG. 3

(From, Millat et al., 1997, Exp. Cell. Res. 230: 362-367 ("Millat 1997") Fig. 7).

```
        VP1₁₋₇₃₆→
AAV1    MAADGYLPDWLEDNLSEGIREWWDLKPGAPKPKANQQKQDDGRGLVLPGYKYLGPFNGLD 60
AAV2    MAADGYLPDWLEDTLSEGIRQWWKLKPGPPPPKPAERHKDDSRGLVLPGYKYLGPFNGLD 60
AAV3-3  MAADGYLPDWLEDNLSEGIREWWALKPGVPQPKANQQHQDNRRGLVLPGYKYLGPNGLD  60
AAV4-4  -MTDGYLPDWLEDNLSEGVREWWALQPGAPKPKANQQHQDNARGLVLPGYKYLGPNGLD  59
AV5     MSFVDHPPDWLEE-VGEGLREFLGLEAGPPKPKPNQQHQDQARGLVLPGYNYLGPNGLD  59
AAV6    MAADGYLPDWLEDNLSEGIREWWDLKPGAPKPKANQQKQDDGRGLVLPGYKYLGPFNGLD 60
AAV7    MAADGYLPDWLEDNLSEGIREWWDLKPGAPKPKANQQKQDNGRGLVLPGYKYLGPFNGLD 60
AAV8    MAADGYLPDWLEDNLSEGIREWWALKPGAPKPKANQQKQDDGRGLVLPGYKYLGPFNGLD 60
hu31    MAADGYLPDWLEDTLSEGIRQWWKLKPGPPPPKPAERHKDDSRGLVLPGYKYLGPNGLD  60
hu32    MAADGYLPDWLEDTLSEGIRQWWKLKPGPPPPKPAERHKDDSRGLVLPGYKYLGPNGLD  60
AAV9    MAADGYLPDWLEDNLSEGIREWWALKPGAPQPKANQQHQDNARGLVLPGYKYLGPNGLD  60
SUBS    -STVDHP-----ETVG--V-QFLK-QA-P-K--PAERKK-DG--------N----F----
         MF          L    DE V P       QS
                          G      Q          R

AAV1    KGEPVNAADAAALEHDKAYDQQLKAGDNPYLRYNHADAEFQERLQEDTSFGGNLGRAVFQ 120
AAV2    KGEPVNEADAAALEHDKAYDRQLDSGDNPYLKYNHADAEFQERLKEDTSFGGNLGRAVFQ 120
AAV3-3  KGEPVNEADAAALEHDKAYDQQLKAGDNPYLKYNHADAEFQERLQEDTSFGGNLGRAVFQ 120
AAV4-4  KGEPVNAADAAALEHDKAYDQQLKAGDNPYLKYNHADAEFQQRLQGDTSFGGNLGRAVFQ 119
AV5     RGEPVNRADEVAREHDISYNEQLEAGDNPYLKYNHADAEFQEKLADDTSFGGNLGKAVFQ 119
AAV6    KGEPVNAADAAALEHDKAYDQQLKAGDNPYLRYNHADAEFQERLQEDTSFGGNLGRAVFQ 120
AAV7    KGEPVNAADAAALEHDKAYDQQLKAGDNPYLRYNHADAEFQERLQEDTSFGGNLGRAVFQ 120
AAV8    KGEPVNAADAAALEHDKAYDQQLQAGDNPYLRYNHADAEFQERLQEDTSFGGNLGRAVFQ 120
hu31    KGEPVNAADAAALEHDKAYDQQLKAGDNPYLKYNHADAEFQERLKEDTSFGGNLGRAVFQ 120
hu32    KGEPVNAADAAALEHDKAYDQQLKAGDNPYLKYNHADAEFQERLKEDTSFGGNLGRAVFQ 120
AAV9    KGEPVNAADAAALEHDKAYDQQLKAGDNPYLKYNHADAEFQERLKEDTSFGGNLGRAVFQ 120
SUBS    R-----E--EV-R---IS-NE--DS------R---------QK-QD---------K----
              R        R  E                          AG
                          Q

VP2₁₃₈→  ┌--HVR1--┐
AAV1    AKKRVLEPLGLVEEGAKTAPGKKRPVEQSPQ-EPDSSSGIGKTGQQPAKKRLNFGQTGDS 179
AAV2    AKKRVLEPLGLVEEPVKTAPGKKRPVEHSPV-EPDSSSGTGKAGQQPARKRLNFGQTGDA 179
AAV3-3  AKKRILEPLGLVEEAAKTAPGKKGAVDQSPQ-EPDSSSGVGKSGKQPARKRLNFGQTGDS 179
AAV4-4  AKKRVLEPLGLVEQAGETAPGKKRPLIESPQ-QPDSSTGIGKKGKQPAKKKLVFEDETGA 178
AV5     AKKRVLEPFGLVEEGAKTAPTGKRIDDHFP--------------KRKKARTEEDSKPSTSSDA 168
AAV6    AKKRVLEPFGLVEEGAKTAPGKKRPVEQSPQ-EPDSSSGIGKTGQQPAKKRLNFGQTGDS 179
AAV7    AKKRVLEPLGLVEEGAKTAPAKKRPVEPSPQRSPDSSTGIGKKGQQPARKRLNFGQTGDS 180
AAV8    AKKRVLEPLGLVEEGAKTAPGKKRPVEPSPQRSPDSSTGIGKKGQQPARKRLNFGQTGDS 180
hu31    AKKRLLEPLGLVEEAAKTAPGKKRPVEQSPQ-EPDSSAGIGKSGSQPAKKKLNFGQTGDT 179
hu32    AKKRLLEPLGLVEEAAKTAPGKKRPVEQSPQ-EPDSSAGIGKSGSQPAKKKLNFGQTGDT 179
AAV9    AKKRLLEPLGLVEEAAKTAPGKKRPVEQSPQ-EPDSSAGIGKSGAQPAKKRLNFGQTGDT 179
SUBS    ----V---F----QGGE---TG-GIDDHF-V-S----S-T--KKQARTREKSVPEDETGA
            I       PV   A  ALIP   Q    T V  T K    E D K STSS S
                             E              A S
                                            R A
```

FIG. 6

```
                 ┌─HVR2─┐              VP3₂₀₃→
AAV1     ESVPD-PQPLGEPPATPAAVGPTTMASGGGAPMADNNEGADGVGNASGNWHCDSTWLGDR 238
AAV2     DSVPD-PQPLGQPPAAPSGLGTNTMATGSGAPMADNNEGADGVGNSSGNWHCDSTWMGDR 238
AAV3-3   ESVPD-PQPLGEPPAAPTSLGSNTMASGGGAPMADNNEGADGVGNSSGNWHCDSQWLGDR 238
AAV4-4   GDGP------PEGSTSGAMS--DDSEMRAAAGGAAVEGGQGADGVGNASGDWHCDSTWSEGH 232
AV5      EAGPSGSQQLQIPAQPASSLGADTMSAGGGPLGDNNQGADGVGNASGDWHCDSTWMGDR 228
AAV6     ESVPD-PQPLGEPPATPAAVGPTTMASGGGAPMADNNEGADGVGNASGNWHCDSTWLGDR 238
AAV7     ESVPD-PQPLGEPPAAPSSVGSGTVAAGGGAPMADNNEGADGVGNASGNWHCDSTWLGDR 239
AAV8     ESVPD-PQPLGEPPAAPSGVGPNTMAAGGGAPMADNNEGADGVGSSSGNWHCDSTWLGDR 239
hu31     ESVPD-PQPIGEPPAAPSGVGSLTMASGGGAPVADNNEGADGVGSSSGNWHCDSQWLGDR 238
hu32     ESVPD-PQPIGEPPAAPSGVGSLTMASGGGAPVADNNEGADGVGSSSGNWHCDSQWLGDR 238
AAV9     ESVPD-PQPIGEPPAAPSGVGSLTMASGGGAPVADNNEGADGVGSSSGNWHCDSQWLGDR 238
SUBS     GDG-S-S-QLQQTSGTMASLDPNEVRAAA-GAMGEGGQ------NA--D-----T-MEGH
         DA      E S AQPATA     AG  ST S     LV                 S
         I              --  DT        A
                            TD
                            S

┌HVR3┐
AAV1     VITTSTRTWALPTYNNHLYKQIS-SASTGASNDNHYFGYSTPWGYFDFNRFHCHFSPRDW 297
AAV2     VITTSTRTWALPTYNNHLYKQIS--SQSGASNDNHYFGYSTPWGYFDFNRFHCHFSPRDW 296
AAV3-3   VITTSTRTWALPTYNNHLYKQIS--SQSGASNDNHYFGYSTPWGYFDFNRFHCHFSPRDW 296
AAV4-4   VTTTSTRTWVLPTYNNHLYKRLG-----ESLQSNTYNGFSTPWGYFDFNRFHCHFSPRDW 287
AV5      VVTKSTRTWVLPSYNNHQYREIKS-GSVDGSNANAYFGYSTPWGYFDFNRFHSHWSPRDW 287
AAV6     VITTSTRTWALPTYNNHLYKQISSAST-GASNDNHYFGYSTPWGYFDFNRFHCHFSPRDW 297
AAV7     VITTSTRTWALPTYNNHLYKQISS-STAGSTNDNTYFGYSTPWGYFDFNRFHCHFSPRDW 298
AAV8     VITTSTRTWALPTYNNHLYKQISNGTSGGATNDNTYFGYSTPWGYFDFNRFHCHFSPRDW 299
hu31     VITTSTRTWALPTYNNHLYKQISNSTSGGSSNDNAYFGYSTPWGYFDFNRFHCHFSPRDW 298
hu32     VITTSTRTWALPTYNNHLYKQISNSTSGGSSNDNAYFGYSTPWGYFDFNRFHCHFSPRDW 298
AAV9     VITTSTRTWALPTYNNHLYKQISNSTSGGSSNDNAYFGYSTPWGYFDFNRFHCHFSPRDW 298
SUBS     -T-K-----V---S----Q-RRLGSGSQSDATQA-T----------------S-W-----
          V             E K AATTEGL  S H
                            G V
                            E A

AAV1     QRLINNNWGFRPKRLNFKLFNIQVKEVTTNDGVTTIANNLTSTVQVFSDSEYQLPYVLGS 357
AAV2     QRLINNNWGFRPKRLNFKLFNIQVKEVTQNDGTTTIANNLTSTVQVFTDSEYQLPYVLGS 356
AAV3-3   QRLINNNWGFRPKKLSFKLFNIQVRGVTQNDGTTTIANNLTSTVQVFTDSEYQLPYVLGS 356
AAV4-4   QRLINNNWGMRPKAMRVKIFNIQVKEVTTSNGETTVANNLTSTVQIFADSSYELPYVMDA 347
AV5      QRLINNYWGFRPRSLRVKIFNIQVKEVTVQDSTTTIANNLTSTVQVFTDDDYQLPYVVGN 347
AAV6     QRLINNNWGFRPKRLNFKLFNIQVKEVTTNDGVTTIANNLTSTVQVFSDSEYQLPYVLGS 357
AAV7     QRLINNNWGFRPKKLRFKLFNIQVKEVTTNDGVTTIANNLTSTIQVFSDSEYQLPYVLGS 358
AAV8     QRLINNNWGFRPKRLSFKLFNIQVKEVTQNEGTKTIANNLTSTIQVFTDSEYQLPYVLGS 359
hu31     QRLINNNWGFRPKRLNFKLFNIQVKEVTDNNGVKTIANNLTSTVQVFTDSDYQLPYVLGS 358
hu32     QRLINNNWGFRPKRLNFKLFNIQVKEVTDNNGVKTIANNLTSTVQVFTDSDYQLPYVLGS 358
AAV9     QRLINNNWGFRPKRLNFKLFNIQVKEVTDNNGVKTIANNLTSTVQVFTDSDYQLPYVLGS 358
SUBS     ---------M--RAMRV-I---------VQDSTT---------I-I-S-DE-E----MDA
                  K S                 QSE E            A   S
                  S
```

FIG. 6 continued

```
                         HVR4
AAV1     AHQGCLPPFPADVFMIPQYGYLTLNNG---SQAVGRSSFYCLEYFPSQMLRTGNNFTFSY 414
AAV2     AHQGCLPPFPADVFMVPQYGYLTLNNG---SQAVGRSSFYCLEYFPSQMLRTGNNFTFSY 413
AAV3-3   AHQGCLPPFPADVFMVPQYGYLTLNNG---SQAVGRSSFYCLEYFPSQMLRTGNNFQFSY 413
AAV4-4   GQEGSLPPFPNDVFMVPQYGYCGLVTGNTSQQQTDRNAFYCLEYFPSQMLRTGNNFEITY 407
AV5      GTEGCLPAFPPQVFTLPQYGYATLNRD-NTENPTERSSFFCLEYFPSKMLRTGNNFEFTY 406
AAV6     AHQGCLPPFPADVFMIPQYGYLTLNNG---SQAVGRSSFYCLEYFPSQMLRTGNNFTFSY 414
AAV7     AHQGCLPPFPADVFMIPQYGYLTLNNG---SQSVGRSSFYCLEYFPSQMLRTGNNFEFSY 415
AAV8     AHQGCLPPFPADVFMIPQYGYLTLNNG---SQAVGRSSFYCLEYFPSQMLRTGNNFQFTY 416
hu31     AHEGCLPPFPADVFMIPQYGYLTLNDG---GQAVGRSSFYCLEYFPSQMLRTGNNFQFSY 415
hu32     AHEGCLPPFPADVFMIPQYGYLTLNDG---SQAVGRSSFYCLEYFPSQMLRTGNNFQFSY 415
AAV9     AHEGCLPPFPADVFMIPQYGYLTLNDG---SQAVGRSSFYCLEYFPSQMLRTGNNFQFSY 415
SUBS     GQQ-S--A--PQ--TL-----CG-VND---GNPTD-NA-F---------------EIT-
           T    N    V     A      Q Q E                        T
                                    R
                                    E S

┌-----------HVR5-----------┐
AAV1     TFEEVPFHSSYAHSQSLDRLMNPLIDQYLYYLNRTQ-NQSGSAQNKDLLFSRGSPAGMSV 473
AAV2     TFEDVPFHSSYAHSQSLDRLMNPLIDQYLYYLSRTN-TPSGTTTQSRLQFSQAGASDIRD 472
AAV3-3   TFEDVPFHSSYAHSQSLDRLMNPLIDQYLYYLNRTQGTTSGTTNQSRLLFSQAGPQSMSL 473
AAV4-4   SFEKVPFHSMYAHSQSLDRLMNPLIDQYLWGLQSTTTGTTLNAGTATTNFTKLRPTNFSN 467
AV5      NFEEVPFHSSFAPSQNLFKLANPLVDQYLYRFVSTN-------NTGGVQFNKNLAGRYAN 459
AAV6     TFEDVPFHSSYAHSQSLDRLMNPLIDQYLYYLNRTQ-NQSGSAQNKDLLFSRGSPAGMSV 473
AAV7     SFEDVPFHSSYAHSQSLDRLMNPLIDQYLYYLARTQSNPGGTAGNRELQFYQGGPSTMAE 475
AAV8     TFEDVPFHSSYAHSQSLDRLMNPLIDQYLYYLSRTQT-TGGTANTQTLGFSQGGPNTMAN 475
hu31     EFENVPFHSSYAHSQSLDRLMNPLIDQYLYYLSKTINGSG--QNQQTLKFSVAGPSNMAV 473
hu32     EFENVPFHSSYAHSQSLDRLMNPLIDQYLYYLSKTINGSG--QNQQTLKFSVAGPSNMAV 473
AAV9     EFENVPFHSSYAHSQSLDRLMNPLIDQYLYYLSKTINGSG--QNQQTLKFSVAGPSNMAV 473
SUBS     T--D-----MF---------A---V----WGFNR-QTNTS--AGTKRTQ-TQGSAATFSN
         S    E                       QS NSTPT   TQNSDVN NKNL QGYRD
         N    K                       V  TG Q    T AE L  YRLR TRI L
                                      A           RG G       GS  E
                                                                ND

┌-┐       ┌HVR6┐       ┌HVR7┐       ┌---HVR8--┐
AAV1     QPKNWLPGPCYRQQRVSKTKTDN-----NNSNFTWTGASKYNLNGRESIINPGTAMASHK 528
AAV2     QSRNWLPGPCYRQQRVSKTSADN-----NNSEYSWTGATKYHLNGRDSLVNPGPAMASHK 527
AAV3-3   QARNWLPGPCYRQQRLSKTANDN-----NNSNFPWTAASKYHLNGRDSLVNPGPAMASHK 528
AAV4-4   FKKNWLPGPSIKQQGFSKTANQNYKIPATGSDSLIKYETHSTLDGRWSALTPGPPMATAG 527
AV5      TYKNWFPGPMGRTQGWNLGSGVN-----RASVSAFATTNRMELEGASYQVPPQPNGMTNN 514
AAV6     QPKNWLPGPCYRQQRVSKTKTDN-----NNSNFTWTGASKYNLNGRESIINPGTAMASHK 528
AAV7     QAKNWLPGPCFRQQRVSKTLDQN-----NNSNFAWTGATKYHLNGRNSLVNPGVAMATHK 530
AAV8     QAKNWLPGPCYRQQRVSTTTGQN-----NNSNFAWTAGTKYHLNGRNSLANPGIAMATHK 530
hu31     QGRNYIPGPSYRQQRVSTTVTQN-----NNSEFAWPGASSWALNGRNSLMNPGPAMASHK 528
hu32     QGRNYIPGPSYRQQRVSTTVTQN-----NNSEFAWPGASSWALNGRNSLMNPGPAMASHK 528
AAV9     QGRNYIPGPSYRQQRVSTTVTQN-----NNSEFAWPGASSWALNGRNSLMNPGPAMASHK 528
SUBS     FAK-WL---CIKT-GWNLGSGV------TG-DSLIKYETHST-D-ASYQVP-QTPGMTAG
         TP   F   MG   F K AND     RA NYTFATTNRME  E  D ALT   VN   NN
         K        F    L   KA        V P TAG KYN     W II    I
         Y                 LD          S        H    E  A
         S                 T
```

FIG. 6 continued

```
                  .--------------HVR9-------------.                          .----.
AAV1    DDEDKFFPMSGVMIFGKESA---GASNTALD--NVMITDEEEIKATNPVATERFGTVAVNFQ 585
AAV2    DDEEKFFPQSGVLIFGKQGS---EKTNVDIE--KVMITDEEEIRTTNPVATEQYGSVSTNLQ 584
AAV3-3  DDEEKFFPMHGNLIFGKEGT---TASNAELD--NVMITDEEEIRTTNPVATEQYGTVANNLQ 585
AAV4-4  PADSKFS-NSQLIFAGPKQN---GNTATVPG--TLIFTSEEELAATNATDTDMWGNLPGGDQ 583
AV5     LQGSNTYALENTMIFNSQPANPGTTATYLEGNMLITSESETQPVNRVAYNVGGQMATNNQ   574
AAV6    DDKDKFFPMSGVMIFGKESA---GASNTALD--NVMITDEEEIKATNPVATERFGTVAVNLQ 585
AAV7    DDEDRFFPSGVLIFGKTGA---TN-KTTLE--NVLMTNEEEIRPTNPVATEEYGIVSSNLQ  586
AAV8    DDEERFFPSNGILIFGKQNA---ARDNADYS-DVMLTSEEEIKTTNPVATEEYGIVADNLQ  587
hu31    EGEDRFFPLSGSLIFGKQGT---GRDNVDAD--KVMITNEEEIKTTNPVATESYGQVATNHQ 585
hu32    EGEDRFFPLSGSLIFGKQGT---GRDNVDAD--KVMITNEEEIKTTNPVATESYGQVATNHQ 585
AAV9    EGEDRFFPLSGSLIFGKQGT---GRDNVDAD--KVMITNEEEIKTTNPVATESYGQVATNHQ 585
SUBS    LQGSNTYAMENTMFANPKQN--TNTATVPG-TLIF-S-S-TQPV-ATDYDMW-NLPGGD-
        PADEK S  QHQLI    SESA EASKAALE-NMLM  D    RA  R   NVF  TMSN L
        DDK     NN V      TPS  AK KTY           L       A      QG  I V N
                S  I      N       EI                            E   S S F
                   N              Y                             R   D
```

```
        .--HVR10---.
AAV1    SSSTDPATGDVHAMGALPGMVWQDRDVYLQGPIWAKIPHTDGHFHPSPLMGGFGLKNPPP 645
AAV2    RGNRQAATADVNTQGVLPGMVWQDRDVYLQGPIWAKIPHTDGHFHPSPLMGGFGLKHPPP 644
AAV3-3  SSNTAPTTGTVNHQGALPGMVWQDRDVYLQGPIWAKIPHTDGHFHPSPLMGGFGLKHPPP 645
AAV4-4  SNSNLPTVDRLTALGAVPGMVWQNRDIYYQGPIWAKIPHTDGHFHPSPLIGGFGLKHPPP 643
AV5     SSTTAPATGTYNLQEIVPGSVWMERDVYLQGPIWAKIPETGAHFHPSPAMGGFGLKHPPP 634
AAV6    SSSTDPATGDVHVMGALPGMVWQDRDVYLQGPIWAKIPHTDGHFHPSPLMGGFGLKHPPP 645
AAV7    AANTAAQTQVVNNQGALPGMVWQNRDVYLQGPIWAKIPHTDGNFHPSPLMGGFGLKHPPP 646
AAV8    QQNTAPQIGTVNSQGALPGMVWQNRDVYLQGPIWAKIPHTDGNFHPSPLMGGFGLKHPPP 647
hu31    SAQAQAQTGWVQNQGILPGMVWQDRDVYLQGPIWAKIPHTDGNFHPSPLMGGFGMKHPPP 645
hu32    SAQAQAQTGWVQNQGILPGMVWQDRDVYLQGPIWAKIPHTDGNFHPSPLMGGFGMKHPPP 645
AAV9    SAQAQAQTGWVQNQGILPGMVWQDRDVYLQGPIWAKIPHTDGNFHPSPLMGGFGMKHPPP 645
SUBS    RNSNLPTVDRLTALEAV--S--ME--I-----------E-GAH-----AI----L-N---
        ASNTA AIADYHTM V       N
        QGTRD   QT NH
           Q    V  L
                   V
                   S
```

```
            .---HVR11---.
AAV1    QILIKNTPVPANPPAEFSATKFASFITQYSTGQVSVEIEWELQKENSKRWNPEVQYTSNY 705
AAV2    QILIKNTPVPANPSTTFSAAKFASFITQYSTGQVSVEIEWELQKENSKRWNPEIQYTSNY 704
AAV3-3  QIMIKNTPVPANPPTTFSPAKFASFITQYSTGQVSVEIEWELQKENSKRWNPEIQYTSNY 705
AAV4-4  QIFIKNTPVPANPATTFSSTPVNSFITQYSTGQVSVQIDWEIQKERSKRWNPEVQFTSNY 703
AV5     MMLIKNTPVPGNI-TSFSDVPVSSFITQYSTGQVTVEMEWELKKENSKRWNPEIQYTNNY 693
AAV6    QILIKNTPVPANPPAEFSATKFASFITQYSTGQVSVEIEWELQKENSKRWNPEVQYTSNY 705
AAV7    QILIKNTPVPANPPEVFTPAKFASFITQYSTGQVSVEIEWELQKENSKRWNPEIQYTSNF 706
AAV8    QILIKNTPVPADPPTTFNQSKLNSFITQYSTGQVSVEIEWELQKENSKRWNPEIQYTSNY 707
hu31    QILIKNTPVPADPPTAFNKDKLNSFITQYSTGQVSVEIEWELQKENSKRWNPEIQYTSNY 705
hu32    QILIKNTPVPADPPTAFNKDKLNSFITQYSTGQVSVEIEWELQKENSKRWNPEIQYTSNY 705
AAV9    QILIKNTPVPADPPTAFNKDKLNSFITQYSTGQVSVEIEWELQKENSKRWNPEIQYTSNY 705
SUBS    MMM-------G-IAAE-SDVPVS-------------QMD--IK--R-------V------
         F         SET TAA  FA
                   S   PT
                   V   QS
                       S
```

FIG. 6 continued

```
          ┌─────HVR12─────┐
AAV1    AKSANVDFTVDNNGLYTEPRPIGTRYLTRPL 736   (SEQ ID NO. 16)
AAV2    NKSVNVDFTVDTNGVYSEPRPIGTRYLTRNL 735   (SEQ ID NO. 17)
AAV3-3  NKSVNVDFTVDTNGVYSEPRPIGTRYLTRNL 736   (SEQ ID NO. 18)
AAV4-4  GQQNSLLWAPDAAGKYTEPRAIGTRYLTHHL 734   (SEQ ID NO. 19)
AV5     NDPQFVDFAPDSTGEYRTTRPIGTRYLTRPL 724   (SEQ ID NO. 20)
AAV6    AKSANVDFTVDNNGLYTEPRPIGTRYLTRPL 736   (SEQ ID NO. 21)
AAV7    EKQTGVDFAVDSQGVYSEPRPIGTRYLTRNL 737   (SEQ ID NO. 22)
AAV8    YKSTSVDFAVNTEGVYSEPRPIGTRYLTRNL 738   (SEQ ID NO. 23)
hu31    YKSNNVEFAVSTEGVYSEPRPIGTRYLTRNL 736   (SEQ ID NO. 24)
hu32    YKSNNVEFAVNTEGVYSEPRPIGTRYLTRNL 736   (SEQ ID NO. 25)
AAV9    YKSNNVEFAVNTEGVYSEPRPIGTRYLTRNL 736   (SEQ ID NO. 26)
SUBS    GQQVSLLWTPDAA-K-RTT-A-------HP-
        NDPQF D    SSN E T          H
        A    TG    NQ  L
        E    A     T
```

FIG. 6 continued

TREATMENT OF MUCOPOLYSACCHARIDOSIS II WITH RECOMBINANT HUMAN IDURONATE-2-SULFATASE (IDS) PRODUCED BY HUMAN NEURAL OR GLIAL CELLS

CROSS-REFERENCE TO RELATED APPLICATIONS

This application is a national stage of International Patent Application No. PCT/US2018/027568, filed Apr. 13, 2018, which claims the benefit of U.S. Provisional Patent Application Nos. 62/485,659, filed Apr. 14, 2017, 62/573,921, filed Oct. 18, 2017, 62/574,355, filed Oct. 19, 2017, and 62/579,686, filed Oct. 31, 2017, which are incorporated by reference herein in their entireties.

REFERENCE TO SEQUENCE LISTING SUBMITTED ELECTRONICALLY

This application incorporates by reference a Sequence Listing submitted with this application as text file entitled "Substitute_Sequence_Listing_12656-104-999.txt" created on Aug. 18, 2022 and having a size of 167,415 bytes.

1. INTRODUCTION

Compositions and methods are described for the delivery of recombinant human iduronate-2-sulfatase (IDS) produced by human neuronal or glial cells to the cerebrospinal fluid (CSF) of the central nervous system (CNS) of a human subject diagnosed with mucopolysaccharidosis II (MPS II).

2. BACKGROUND OF THE INVENTION

Hunter syndrome/MPS II is a rare X-linked recessive genetic disease occurring in 0.5 to 1.3 per 100,000 male live births. This progressive and devastating disease is caused by genetic mutation in the IDS gene leading to deficiency of the lysosomal storage enzyme iduronate-2-sulfatase, an enzyme required for the lysosomal catabolism of heparan sulfate and dermatan sulfate. These ubiquitous polysaccharides, called GAGs (glycosaminoglycans), accumulate in tissues and organs of MPS II patients resulting in the characteristic storage lesions and diverse disease sequelae. Morbidity and mortality are high in this patient population; death has been reported to occur at a mean age of 11.7 years in patients with the severe phenotype (characterized by neurocognitive deterioration) and 21.7 years in patients with a mild or attenuated phenotype. (Young et al., 1982, A clinical and genetic study of Hunter's syndrome. 2 Differences between the mild and severe forms. J. Medical Genetics 19:408-411). The majority (two-thirds) of patients are reported to have the severe form of this disease. (Wraith J E, et al., 2007, Enzyme replacement therapy in patients who have mucopolysaccharidosis I and are younger than 5 years: Results of a multinational study of recombinant human alpha-L-Iduronidase (Laronidase). Pediatrics 120(1):E37-E46). While the disease primarily affects boys, affected females have been reported as a result of non-random x-inactivation and/or mutation in both alleles of the gene. (Martin et al., 2008, Recognition and diagnosis of mucopolysaccharidosis II (Hunter Syndrome). Pediatrics 121:e377). However, MPS II in females is extremely rare, occurring less than 2% of the time.

Patients with MPS II appear normal at birth, but signs and symptoms of disease typically present between the ages of 18 months and 4 years in the severe form and between the ages of 4 and 8 years in the attenuated form. Signs and symptoms common to all affected patients include short stature, coarse facial features, macrocephaly, macroglossia, hearing loss, hepato- and splenomegaly, dystosis multiplex, joint contractures, spinal stenosis and carpal tunnel syndrome. Frequent upper respiratory and ear infections occur in most patients and progressive airway obstruction is commonly found, leading to sleep apnea and often death. Cardiac disease is a major cause of death in this population and is characterized by valvular dysfunction leading to right and left ventricular hypertrophy and heart failure. Death is generally attributed to obstructive airway disease or cardiac failure.

In severe forms of the disease, early developmental milestones may be met, but developmental delay is readily apparent by 18-24 months. Some patients fail hearing screening tests in the first year and other milestones are delayed, including ability to sit unsupported, ability to walk, and speech. Developmental progression begins to plateau between 3 and 5 years of age, with regression reported to begin around 6.5 years. Of the ~50% of children with MPS II who become toilet trained, most, if not all, will lose this ability as the disease progresses. (Wraith et al., 2007, supra; Martin et al., 2008, supra).

Patients with significant neurologic involvement exhibit severe behavioral disturbances including hyperactivity, obstinacy, and aggression beginning in the second year of life and continuing until age 8-9, when neurodegeneration attenuates this behavior. (Muenzer, et al., 2009, Mucopolysaccharidosis I: Management and Treatment Guidelines, Pediatric 123(1): 19-29).

Seizures are reported in over half of severely affected patients who reach the age of 10, and by the time of death most patients with CNS involvement are severely mentally handicapped and require constant care. (Wraith et al., 2007, supra; Martin et al., 2008, supra). Although patients with attenuated disease exhibit normal intellectual functioning, MRI imaging reveals gross brain abnormalities in all patients with MPS II including white matter lesions, enlarged ventricles, and brain atrophy. (Muenzer, et al., 2009, supra).

Enzyme replacement therapy (ERT) with recombinant idursulfase produced by HT1080 (fibrosarcoma) cells (Elaprase®, Shire Human Genetic Therapies) is the only approved product for the treatment of Hunter syndrome and is administered as a weekly infusion. (ELAPRASE (idursulfase) injection [package insert]. Lexington, Mass.: Shire Human Genetic Therapies, Inc; 2013, available at http://pi.shirecontent.com/PI/PDFs/Elaprase_USA_ENG.pdf).

However, ERT as currently administered does not cross the blood brain barrier and is therefore unable to address the unmet need in patients with severe disease, i.e., MPS II with CNS/neurocognitive and behavioral involvement. In a recent clinical trial designed to address this problem, idursulfase (Elaprase) formulated for intrathecal administration was administered once monthly to pediatric patients using an intrathecal drug delivery device implanted into the spine (insertion of the catheter at the level of L4/L5 with implantation of the access port via an incision on the lower ribs). The patients also received concurrent i.v. idursulfase once weekly. See Muenzer et al., 2016, Genetics in Med 18: 73-81, esp. p. 74; abstract available at https://www.ncbi.nlm.nih.gov/pubmed/25834948?dopt=Abstract). Device malfunction led to partial revision, total surgical revision, or removal in 6 of the 12 (50%) of the treated patients. Notably, 12 of 14 SAEs (serious adverse events) were device-related (complication of device insertion, device dislocation/connection issue, device breakage/malfunction/failure, implant site infection, procedural pain, and wound dehiscence). (Muenzer et al., 2016, p. 75, col. 2 and FIG. 1). Device breakage and catheter migration from the spinal canal was exacerbated by the high activity level of this pediatric population. (Muenzer et al., 2016 at p. 78 Discussion).

3. SUMMARY OF THE INVENTION

The invention involves the delivery of recombinant human iduronate-2-sulfatase (rhIDS) produced by human neuronal or glial cells to the cerebrospinal fluid (CSF) of the central nervous system (CNS) of a human subject diagnosed with mucopolysaccharidosis II (MPS II), including, but not limited to patients diagnosed with Hunter syndrome.

In a preferred embodiment, the treatment is accomplished via gene therapy—e.g., by administering a viral vector or other DNA expression construct encoding human IDS (hIDS), or a derivative of hIDS, to the CSF of a patient (human subject) diagnosed with MPS II, so that a permanent depot of transduced neuronal and/or glial cells is generated that continuously supplies the transgene product to the CNS. The rhIDS secreted from the neuronal/glial cell depot into the CSF will be endocytosed by cells in the CNS, resulting in "cross-correction" of the enzymatic defect in the recipient cells. Moreover, it has been found, unexpectedly, that the depot of transduced neural and glial cells in the CNS can deliver the recombinant enzyme to both the CNS and systemically, which may reduce or eliminate the need for systemic treatment, e.g., weekly i.v. injections of the enzyme.

In an alternative embodiment, the hIDS can be produced by human neuronal or glial cells in cell culture (e.g., bioreactors) and administered as an enzyme replacement therapy ("ERT"), e.g., by injecting the enzyme—into the CSF, directly into the CNS, and/or systemically. However, the gene therapy approach offers several advantages over ERT since systemic delivery of the enzyme will not result in treating the CNS because the enzyme cannot cross the blood brain barrier; and, unlike the gene therapy approach of the invention, direct delivery of the enzyme to the CSF and/or CNS would require repeat injections which are not only burdensome, but pose a risk of infection.

The hIDS encoded by the transgene can include, but is not limited to human IDS (hIDS) having the amino acid sequence of SEQ ID NO. 1 (as shown in FIG. 1), and derivatives of hIDS having amino acid substitutions, deletions, or additions, e.g., including but not limited to amino acid substitutions selected from corresponding non-conserved residues in orthologs of IDS shown in FIG. 2, with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inhert Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety.

For example, amino acid substitutions at a particular position of hIDS can be selected from among corresponding non-conserved amino acid residues found at that position in the IDS orthologs aligned in FIG. 2, with the proviso that such substitutions do not include any of the deleterious mutations shown in FIG. 3 or as reported by Sukegawa-Hayasaka et al., 2006, supra; Millat et al., 1998, supra; or Bonucelli et al., 2001, supra, each of which is incorporated by reference herein in its entirety. The resulting transgene product can be tested using conventional assays in vitro, in cell culture or test animals to ensure that the mutation does not disrupt IDS function. Preferred amino acid substitutions, deletions or additions selected should be those that maintain or increase enzyme activity, stability or half-life of IDS, as tested by conventional assays in vitro, in cell culture or animal models for MPS II. For example, the enzyme activity of the transgene product can be assessed using a conventional enzyme assay with, for example, 4-Methylumbelliferyl α-L-idopyranosiduronic acid 2-sulfate or 4-methylumbelliferyl sulfate as the substrate (see, e.g., Lee et al., 2015, Clin. Biochem. 48(18):1350-1353, Dean et al., 2006, Clin. Chem. 52(4):643-649 for exemplary IDS enzyme assays that can be used, each of which is incorporated by reference herein in its entirety). The ability of the transgene product to correct MPS II phenotype can be assessed in cell culture; e.g., by transducing MPS II cells in culture with a viral vector or other DNA expression construct encoding hIDS or a derivative; by adding the transgene product or a derivative to MPS II cells in culture; or by co-culturing MPS II cells with human neuronal/glial host cells engineered to express and secrete rhIDS or a derivative, and determining correction of the defect in the MPS II cultured cells, e.g., by detecting IDS enzyme activity and/or reduction in GAG storage in the MPS II cells in culture (see, e.g., Stroncek et al., 1999, Transfusion 39(4):343-350, which is incorporated by reference herein in its entirety).

Animal models for MPS II have been described that can be used to assess the therapeutics described herein. For example, a knockout mouse model (IDS-knockout) of MPS II was engineered by replacing exons 4 and 5 of the IDS gene with the neomycin resistance gene. (Garcia et al., 2007, J Inherit Metab Dis 30: 924-34). This IDS-knockout mouse exhibits many of the characteristics of MPS II, including skeletal abnormalities, hepatosplenomegaly, elevated urinary and tissue GAG, and brain storage lesions (Muenzer et al., 2001, Acta Paediatr Suppl 91:98-99) and was used to assess the effect of enzyme replacement therapy in MPS II in support of clinical trials for ERT. This mouse model, therefore, is a relevant model for studying the effects of gene therapy delivering rIDS produced by neuronal or glial cells as a treatment for MPS II (see, e.g., Polito and Cosma, 2009, Am. J. Hum. Genet. 85(2):296-301, which is incorporated by reference herein in its entirety).

Preferably, the hIDS transgene produced by the human neuronal/glial cells should be controlled by expression control elements that function in neurons and/or glial cells, e.g., the CB7 promoter (a chicken β-actin promoter and CMV enhancer), and can include other expression control elements that enhance expression of the transgene driven by the vector (e.g., chicken β-actin intron and rabbit β-globin poly A signal). The cDNA construct for the hIDS transgene should include a coding sequence for a signal peptide that ensures proper co- and post-translational processing (glycosylation and protein sulfation) by the transduced CNS cells. Such signal peptides used by CNS cells may include but are not limited to:

Oligodendrocyte-myelin glycoprotein (hOMG) signal peptide:
(SEQ ID NO: 2)
MEYQILKMSLCLFILLFLTPGILC Cellular repressor of E1A-stimulated genes 2 (hCREG2) signal peptide:
(SEQ ID NO: 3)
MSVRRGRRPARPGTRLSWLLCCSALLSPAAG V-set and transmembrane domain containing 2B (hVSTM2B) signal peptide:
(SEQ ID NO: 4)
MEQRNRLGALGYLPPLLLHALLLFVADA Protocadherin alpha-1 (hPCADHA1) signal peptide:
(SEQ ID NO: 5)
MVFSRRGGLGARDLLLWLLLLAAWEVGSG FAM19A1 (TAFA1) signal peptide:
(SEQ ID NO: 6)
MAMVSAMSWVLYLWISACA Interleukin-2 signal peptide:
(SEQ ID NO: 14)
MYRMQLLSCIALILALVTNS Signal peptides may also be referred to herein as leader sequences or leader peptides.

The recombinant vector used for delivering the transgene should have a tropism for cells in the CNS, including but not limited to neurons and/or glial cells. Such vectors can include non-replicating recombinant adeno-associated virus vectors ("rAAV"), particularly those bearing an AAV9 or AAVrh10 capsid are preferred. AAV variant capsids can be used, including but not limited to those described by Wilson in U.S. Pat. No. 7,906,111 which is incorporated by reference herein in its entirety, with AAV/hu.31 and AAV/hu.32 being particularly preferred; as well as AAV variant capsids described by Chatterjee in U.S. Pat. Nos. 8,628,966, 8,927,514 and Smith et al., 2014, Mol Ther 22: 1625-1634, each of which is incorporated by reference herein in its entirety. However, other viral vectors may be used, including but not limited to lentiviral vectors, vaccinia viral vectors, or non-viral expression vectors referred to as "naked DNA" constructs.

In one embodiment, Construct 1 can be used for delivering the transgene. Construct 1 is a recombinant adeno-associated virus serotype 9 capsid containing human iduronate-2-sulfatase expression cassette wherein expression is driven by a hybrid of the cytomegalovirus (CMV) enhancer and the chicken beta actin promoter (CB7), wherein the IDS expression cassette is flanked by inverted terminal repeats (ITRs) and the transgene includes the chicken beta actin intron and a rabbit beta-globin polyadenylation (polyA) signal.

Pharmaceutical compositions suitable for administration to the CSF comprise a suspension of the rhIDS vector in a formulation buffer comprising a physiologically compatible aqueous buffer, a surfactant and optional excipients. In certain embodiments, the pharmaceutical compositions are suitable for intrathecal administration. In certain embodiments, the pharmaceutical compositions are suitable for intracisternal administration (injection into the cisterna magna). In certain embodiments, the pharmaceutical compositions are suitable for injection into the subarachnoid space via a C1-2 puncture. In certain embodiments, the pharmaceutical compositions are suitable for intracerebroventricular administration. In certain embodiments, the pharmaceutical compositions are suitable for administration via lumbar puncture.

Therapeutically effective doses of the recombinant vector should be administered to the CSF via intrathecal administration (i.e., injection into the subarachnoid space so that the recombinant vectors distribute through the CSF and transduce cells in the CNS). This can be accomplished in a number of ways—e.g., by intracranial (cisternal or ventricular) injection, or injection into the lumbar cistern. For example, intracisternal (IC) injection (into the cisterna magna) can be performed by CT-guided suboccipital puncture; or injection into the subarachnoid space can be performed via a C1-2 puncture when feasible for the patient; or lumbar puncture (typically diagnostic procedures performed in order to collect a sample of CSF) can be used to access the CSF. Alternatively, intracerebroventricular (ICV) administration (a more invasive technique used for the introduction of antiinfective or anticancer drugs that do not penetrate the blood-brain barrier) can be used to instill the recombinant vectors directly into the ventricles of the brain. Alternatively, intranasal administration may be used to deliver the recombinant vector to the CNS.

CSF concentrations can be monitored by directly measuring the concentration of rhIDS in the CSF fluid obtained from occipital or lumbar punctures, or estimated by extrapolation from concentrations of the rhIDS detected in the patient's serum.

By way of background, human IDS is translated as a 550 amino acid polypeptide that contains eight potential N-glycosylation sites ($N^{31}$, $N^{115}$, $N^{144}$, $N^{246}$, $N^{280}$, $N^{325}$, $N^{513}$ and $N^{537}$) depicted in FIG. 1 and includes a 25 amino acid signal sequence which is cleaved during processing. An initial 76 kDa intracellular precursor is converted into a phosphorylated 90 kDa precursor after modification of its oligosaccharide chains in the Golgi apparatus. This precursor is processed by glycosylation modifications and proteolytic cleavage through various intracellular intermediates to a major 55 kDa form. To summarize, after removal of the 25 aa signal sequence, proteolytic processing involves N-terminal proteolytic cleavage downstream of $N^{31}$ removing a propeptide of eight amino acids (residues 26-33), and C-terminal proteolytic cleavage upstream of $N^{513}$ which releases an 18 kDa polypeptide and produces a 62 kDa intermediate that is converted to a 55 kDa mature form. Further proteolytic cleavage yields a 45 kDa mature form located in the lysosomal compartment. (See FIG. 4 for diagram reproduced from Millat et al., 1997, Exp Cell Res 230: 362-367 ("Millat 1997"); Millat et al. 1997, Biochem J. 326: 243-247 ("Millat 1997a"); and Froissart et al., 1995, Biochem J. 309:425-430, each of which is incorporated by reference herein in its entirety).

A formylglycine modification of $C^{84}$ (shown in bold in FIG. 1) required for enzyme activity probably occurs as an early post-translational or co-translational event, most probably in the endoplasmic reticulum. (See, Millat 1997a, citing Schmidt et al., 1995, Cell 82: 271-278). Post-translational processing continues in the Golgi to include addition of complex sialic acid-containing glycans and acquisition of mannose-6-phosphate residues which tag the enzyme for delivery to the lysosomal compartment. (See, Clarke, 2008, Expert Opin Pharmacother 9: 311-317 for a concise review which is incorporated by reference herein in its entirety). While no single glycosylation site is essential for IDS stability, glycosylation at position $N^{280}$ is important for cellular internalization and lysosomal targeting via the mannose-6-phosphate (M6P) receptor. (Chung et al., 2014, Glycoconj J 31:309-315 at p. 310, first column). In the normal physiologic state, IDS is produced at very low levels and very little, if any, enzyme is secreted from the cell. (Clarke, 2008, supra).

The invention is based, in part, on the following principles:

(i) Neuronal and glial cells in the CNS are secretory cells that possess the cellular machinery for post-translational processing of secreted proteins—including glycosylation, mannose-6-phosphorylation, and tyrosine-O-sulfation—robust processes in the CNS. See, e.g., Sleat et al., 2005, Proteomics 5: 1520-1532, and Sleat 1996, J Biol Chem 271: 19191-98 which describes the human brain mannose-6-phosphate glycoproteome and notes that the brain contains more proteins with a much greater number of individual isoforms and mannose-6-phosphorylated proteins than found in other tissues; and Kanan et al., 2009, Exp. Eye Res. 89: 559-567 and Kanan & Al-Ubaidi, 2015, Exp. Eye Res. 133: 126-131 reporting the production of tyrosine-sulfated glycoproteins secreted by neuronal cells, each of which is incorporated by reference in its entirety for post-translational modifications made by human CNS cells.

(ii) The human brain produces multiple isoforms of natural/native IDS. In particular, N-terminal sequencing of human brain mannose-6-phosphorylated glycoproteins revealed that the N-terminal sequence of the mature 42 kDa chain of hIDS varies in the brain, starting at positions 34 or 36 as follows: $T^{34}$DALNVLLI; and $A^{36}$LNVLLIIV. (Sleat, 2005, Proteomics 5: 1520-1532, Table S2). Two of the eight N-linked glycosylation sites, namely $N^{280}$ and $N^{116}$, were found to be mannose-6-phophorylated in IDS obtained from human brain. (Sleat et al., 2006, Mol & Cell Proeomics 5.4: 686-701, reported at Table V).

(iii) During processing of hIDS, two polypeptides, 76 kDa and 90 kDa, are secreted by neural and glial cells, but only the 90 kDa polypeptide is mannose-6-phosphorylated, which is necessary for secreted forms of the enzyme to achieve cross correction. (See, Millat, 1997, FIG. 1 results for transduced lymphoblastoid cells, and Froissart 1995, FIG. 4 showing similar results for transduced fibroblasts—in culture medium, only the 90 kDa form is phosphorylated). Interestingly, it has been demonstrated that recombinant IDS produced by neuronal and glial cells may be endocytosed by recipient CNS cells more avidly than recombinant IDS produced by other cells such as kidney. Daniele 2002 (Biochimica et Biophysica Acta 1588(3):203-9) demonstrated M6P-receptor mediated endocytosis of recombinant IDS from conditioned media of transduced neuronal and glial cell cultures by a recipient population of non-transduced neuronal and glial cells which properly processed the precursor to the 45 kDa mature active form. Uptake of the recombinant IDS produced by the neuronal and glial cell lines (74% endocytosis) far exceeded uptake of the enzyme produced by a kidney cell line (5.6% endocytosis). In each case, uptake was inhibited by M6P, indicating that recombinant IDS uptake was M6P-receptor mediated. (See Daniele 2002, Tables 2 and 4 and accompanying description in Results at pp. 205-206 summarized in Table 1 below).

TABLE 1

Summary of Results Reported in Daniele 2002

| Cell Line Source of rIDS | Media Enzyme Units | Recipient Cells: Units Recovered | | % Endocytosis (mean value) |
|---|---|---|---|---|
| | | Neuronal | Glial | |
| Kidney$^{(transfected)}$ | 35 U | 1.7 U | 2.2 U | 5.6% |
| Neuronal$^{(Ad-transduced)}$ | 12 U | 8.8 U | 8.8 U | 74% |
| Glial$^{(Ad-transduced)}$ | 14 U | 10.5 U | 10.5 U | 74% |

(iv) The gene therapy approach described herein should result in the continuous secretion of an hIDS glycoprotein precursor of about 90 kDa as measured by polyacrylamide gel electrophoresis (depending on the assay used) that is enzymatically active. First, the enzyme responsible for the formylglycine modification of $C^{84}$ which is required for IDS activity—the FGly-Generating Enzyme (FGE, aka SUMF1)—is expressed in the cerebral cortex of the human brain (gene expression data for SUMF1 may be found, for example, at GeneCards, accessible at http://www.genecards.org). Second, the secreted glycosylated/phosphorylated rIDS produced by transduced neurons and glial cells in situ should be taken up and correctly processed by untransduced neural and glial cells in the CNS. Without being bound to any theory, it appears that the secreted rhIDS precursor produced in situ by gene therapy may be more avidly endocytosed by recipient cells in the CNS than would traditional recombinant enzymes used for ERT if administered to the CNS. For example, Elaprase® (made in HT1080, a fibrosarcoma cell line) is a purified protein reported to have a molecular weight of about 76 kDa—not the 90 kDa species secreted by neuronal and glial cells that appears to be more heavily phosphorylated. While the eight N-linked glycosylation sites are reported to be fully occupied in Elaprase® and contain two bis-mannose-6-phosphate terminated glycans as well as complex highly sialylated glycans, the post-translational modification of $C^{84}$ to FGly, which is an absolute requirement for enzyme activity, is only about 50%. (Clarke, 2008, Expert Opin Pharmacother 9:311-317; Elaprase® Full Prescribing Information and EMA filing). Another recombinant product, Hunterase® is made in CHO cells. While reported to have higher FGly and activity than Elaprase®, mannose-6-phosphorylation and uptake did not differ. (Chung, 2014, Glycoconj J 31:309-315).

(v) The extracellular IDS efficacy in vivo depends on uptake (cell and lysosome internalization) through M6P and its active site formylglycine (FGly), which is converted from $C^{84}$ through post-translational modification by formylglycine-generating enzyme. As shown above in Table 1, brain cells (neuronal and glial cells) show higher enzyme activities when incubated with IDS precursor media secreted by transduced neuronal and glial cells than with IDS precursor media secreted by genetically engineered kidney cells. The resultant five-fold increase in activity can likely be attributed to the efficient uptake of IDS (See Daniele 2002, Tables 2 and 4). Commercial forms of IDS, which are generated by CHO cells or HT-1080 cells, have a FGly content of about about 50% to 70%, which determines the enzyme activity. However, neuronal and glial cells may improve upon this activity, due to improvement of IDS uptake.

(vi) The cellular and subcellular trafficking/uptake of lysosomal proteins, including IDS, is through M6P. IDS from brain cells may contain higher M6P content, as reported in Daniele 2002, and in Sleat, Proteomics, 2005 (indicating that the human brain contains more (in both a quantitative and qualitative sense) Man6-P glycoproteins than other tissues.). It is possible to measure the M6P content of an IDS precursor, as done in Daniele 2002. In the presence of inhibitory M6P (e.g., 5 mM), the uptake of IDS precursor generated by non-neuronal or non-glial cells, such as the genetically engineered kidney cells of Daniele 2002, is predicted to decrease to levels close to that of the control cells, as was shown in Daniele 2002. While in the presence of inhibitory M6P, the uptake of IDS precursor generated by brain cells, such as neuronal and glial cells, is predicted to remain at a high level, as was shown in Daniele 2002, where the uptake was four times higher than control cells and comparable to the level of IDS activity (or uptake) of IDS precursor generated by genetically engineered kidney cells without the presence of inhibitory M6P. This assay allows for a way to predict the M6P content in IDS precursor generated by brain cells, and, in particular, to compare the M6P content in IDS precursors generated by different types of cells. The gene therapy approach described herein should result in the continuous secretion of an hIDS precursor that may be taken up into neuronal and glial cells at a high level in the presence of inhibitory M6P in such an assay.

(vii) The M6P content and uptake of IDS precursor may also be demonstrated by 90 kDa and 76 kDa gel bands (e.g., SDS-PAGE gel bands). The 90 kDa is reported to be highly glycosylated/phosphorylated and contains M6P, while 76 kDa is not. A very broad gel band with a range from 76 kDa to 95 kDa and with an average MW of 80-85 kDa, similar to the IDS precursor gel band generated from genetically engineered kidney cells (Daniele 2002, FIG. 1), may be contrasted with a gel band of IDS precursor generated from brain cells. In Daniele 2002, the gel band cannot be obtained due to unsuccessful immunoprecipitation of the IDS precursor. The gene therapy approach described herein should result in the continuous secretion of an hIDS precursor that differs from the IDS precursor gel band generated from genetically engineered kidney cells.

(viii) The M6P content of commercial IDS precursor is 2 to 2.5 mol/mol, majority of which is present in a form of di-phosphorylated glycans. Although in average, every IDS precursor is phosphorylated, a normal distribution of glycans will have some IDS precursor with 2, 1 and 0 of di-phosphorylated M6P glycans assuming multiple phosphorylation sites. Uptake rate should be significant higher with multiple phosphorylation.

(ix) The glycosylation of hIDS by human cells of the CNS will result in the addition of glycans that can improve stability, half-life and reduce unwanted aggregation of the transgene product. Significantly, the glycans that are added to hIDS of the invention include 2,6-sialic acid, incorporating Neu5Ac ("NANA") but not its hydroxylated derivative, NeuGc (N-Glycolylneuraminic acid, i.e., "NGNA" or "Neu5Gc"). Such glycans are not present in recombinant IDS products, such as Hunterase®, made in CHO cells because CHO cells do not have the 2,6-sialyltransferase required to make this post-translational modification; nor do CHO cells produce bisecting GlcNAc, although they do add Neu5Gc (NGNA) as sialic acid not typical (and potentially immunogenic) to humans instead of Neu5Ac (NANA). See, e.g., Dumont et al., 2016, Critical Rev in Biotech 36(6):1110-1122 (Early Online pp. 1-13 at p. 5); and Hague et al., 1998 Electrophor 19:2612-2630 ("[t]he CHO cell line is considered 'phenotypically restricted,' in terms of glycosylation, due to the lack of an α2,6-sialyl-transferase"). Moreover, CHO cells can also produce an immunogenic glycan, the α-Gal antigen, which reacts with anti-α-Gal antibodies present in most individuals, and at high concentrations can trigger anaphylaxis. See, e.g., Bosques, 2010, Nat Biotech 28: 1153-1156. The human glycosylation pattern of the rhIDS of the invention should reduce immunogenicity of the transgene product and improve efficacy.

(x) Immunogenicity of a transgene product could be induced by various factors, including the immune condition of the patient, the structure and characteristics of the infused protein drug, the administration route, and the duration of treatment. Process-related impurities, such as host cell protein (HCP), host cell DNA, and chemical residuals, and product-related impurities, such as protein degradants and structural characteristics, such as glycosylation, oxidation and aggregation (sub-visible particles), may also increase immunogenicity by serving as an adjuvant that enhances the immune response. The amounts of process-related and product-related impurities can be affected by the manufacturing process: cell culture, purification, formulation, storage and handling, which can affect commercially manufactured IDS products. In gene therapy, proteins are produced in vivo, such that process-related impurities are not present and protein products are not likely to contain product-related impurities/degradants associated with proteins produced by recombinant technologies, such as protein aggregation and protein oxidation. Aggregation, for example, is associated with protein production and storage due to high protein concentration, surface interaction with manufacturing equipment and containers, and the purification process with certain buffer systems. But these conditions that promote aggregation are not present when a transgene is expressed in vivo. Oxidation, such as methionine, tryptophan and histidine oxidation, is also associated with protein production and storage, caused, for example, by stressed cell culture conditions, metal and air contact, and impurities in buffers and excipients. The proteins expressed in vivo may also oxidize in a stressed condition, but humans, like many organisms, are equipped with an antioxidation defense system, which not only reduces the oxidation stress, but can also repairs and/or reverses the oxidation. Thus, proteins produced in vivo are not likely to be in an oxidized form. Both aggregation and oxidation could affect the potency, PK (clearance) and can increase immunogenicity concerns. The gene therapy approach described herein should result in the continuous secretion of an hIDS precursor with a reduced immunogenicity compared to commercially manufactured products.

(xi) In addition to the N-linked glycosylation sites, hIDS contains a tyrosine ("Y") sulfation site (PSSEKY$^{165}$ENTKTCRGPD). (See, e.g., Yang et al., 2015, Molecules 20:2138-2164, esp. at p. 2154 which is incorporated by reference in its entirety for the analysis of amino acids surrounding tyrosine residues subjected to protein tyrosine sulfation. The "rules" can be summarized as follows: Y residues with E or D within +5 to −5 position of Y, and where position −1 of Y is a neutral or acidic charged amino acid—but not a basic amino acid, e.g., R, K, or H that abolishes sulfation). While not intending to be bound by any theory, sulfation of this site in hIDS may improve stability of the enzyme and binding affinity for substrate. Tyrosine-sulfation of hIDS—a robust post-translational process in human CNS cells—should result in improved processing and activity of transgene products. The significance of tyrosine-sulfation of lysosomal proteins has not been elucidated; but in other proteins it has been shown to increase avidity of protein-protein interactions (antibodies and receptors), and to promote proteolytic processing (peptide hormone). (See, Moore, 2003, J Biol. Chem. 278: 24243-46; and Bundegaard et al., 1995, The EMBO J 14: 3073-79). The tyrosylprotein sulfotransferase (TPST1) responsible for tyrosine-sulfation (which may occur as a final step in IDS processing) is apparently expressed at higher levels (based on mRNA) in the brain (gene expression data for TPST1 may be found, for example, at the EMBL-EBI Expression Atlas, accessible at http://www.ebi.ac.uk/gxa/home). Such post-translational modification, at best, is under-represented in CHO cell products. Unlike human CNS cells, CHO cells are not secretory cells and have a limited capacity for post-translational tyrosine-sulfation. (See, e.g., Mikkelsen & Ezban, 1991, Biochemistry 30: 1533-1537, esp. discussion at p. 1537).

For the foregoing reasons, the production of rhIDS by human neuronal and/or glial cells should result in a "biobetter" molecule for the treatment of MPS II accomplished via gene therapy—e.g., by administering a viral vector or other DNA expression construct encoding rhIDS to the CSF of a patient (human subject) diagnosed with an MPS II disease (including but not limited to Hunter) to create a permanent depot in the CNS that continuously supplies a fully human-glycosylated, mannose-6-phosphorylated, sulfated transgene product secreted by the transduced CNS cells. The hIDS transgene product secreted from the depot into the CSF will be endocytosed by cells in the CNS, resulting in "cross-correction" of the enzymatic defect in the MPS II recipient cells.

It is not essential that every rhIDS molecule produced either in the gene therapy or protein therapy approach be fully glycosylated, phosphorylated, and sulfated. Rather, the population of glycoproteins produced should have sufficient glycosylation (including 2,6-sialylation and mannose-6-phophorylation) and sulfation to demonstrate efficacy. The goal of gene therapy treatment of the invention is to slow or arrest the progression of disease. Efficacy may be monitored by measuring cognitive function (e.g., prevention or decrease in neurocognitive decline); reductions in biomarkers of disease (such as GAG) in CSF and or serum; and/or increase in IDS enzyme activity in CSF and/or serum. Signs of inflammation and other safety events may also be monitored.

As an alternative, or an additional treatment to gene therapy, the rhIDS glycoprotein can be produced in human neural or glial cell lines by recombinant DNA technology and the glycoprotein can be administered to patients diagnosed with MPS II systemically and/or into the CSF for ERT). Human cell lines that can be used for such recombinant glycoprotein production include but are not limited to HT-22, SK-N-MC, HCN-1A, HCN-2, NT2, SH-SY5y, hNSC11, or ReNcell VM (see, e.g., Dumont et al., 2016, Critical Rev in Biotech 36(6):1110-1122 "Human cell lines for biopharmaceutical manufacturing: history, status, and future perspectives" which is incorporated by reference in its entirety for a review of the human cell lines that could be used for the recombinant production of the rHuGlyIDS glycoprotein). To ensure complete glycosylation, especially sialylation, and tyrosine-sulfation, the cell line used for production can be enhanced by engineering the host cells to co-express α-2,6-sialyltransferase (or both α-2,3- and α-2, 6-sialyltransferases) and/or TPST-1 and TPST-2 enzymes responsible for tyrosine-O-sulfation.

While the delivery of rhIDS should minimize immune reactions, the clearest potential source of toxicity related to CNS-directed gene therapy is generating immunity against the expressed rhIDS protein in human subjects who are genetically deficient for IDS and, therefore, potentially not tolerant of the protein and/or the vector used to deliver the transgene.

Thus, in a preferred embodiment, it is advisable to co-treat the patient with immune suppression therapy—especially when treating patients with severe disease who have close to zero levels of IDS. Immune suppression therapies involving a regimen of tacrolimus or rapamycin (sirolimus) in combination with mycophenolic acid, or other immune suppression regimens used in tissue transplantation procedures can be employed. Such immune suppression treatment may be administered during the course of gene therapy, and in certain embodiments, pre-treatment with immune suppression therapy may be preferred. Immune suppression therapy can be continued subsequent to the gene therapy treatment, based on the judgment of the treating physician, and may thereafter be withdrawn when immune tolerance is induced; e.g., after 180 days.

Combinations of delivery of the rhIDS to the CSF accompanied by delivery of other available treatments are encompassed by the methods of the invention. The additional treatments may be administered before, concurrently or subsequent to the gene therapy treatment. Available treatments for MPS II that could be combined with the gene therapy of the invention include but are not limited to enzyme replacement therapy using Elaprase® administered systemically or to the CSF; and/or HSCT therapy.

3.1 Illustrative Embodiments 3.1.1. Set 1

1. Glycosylated recombinant human iduronate-2-sulfatase (IDS) precursor produced by human neuronal or human glial cells.

2. The glycosylated recombinant human IDS precursor of paragraph 1, which is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis.

3. The glycosylated recombinant human IDS precursor of paragraph 1, which is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

4. The glycosylated recombinant human IDS precursor of any one of paragraphs 1 to 3, which is secreted from a depot of cells in the central nervous system genetically engineered to secrete said human IDS glycoprotein precursor.

5. The glycosylated recombinant human IDS precursor of paragraph 4, in which the depot is formed in a human subject's brain.

6. The glycosylated recombinant human IDS precursor of any one of paragraphs 1 to 5, in which the human neuronal or human glial cells are deficient in IDS activity.

7. The glycosylated recombinant human IDS precursor of any one of paragraphs 1 to 6, in which the glycosylated recombinant human IDS precursor comprises the amino acid sequence of SEQ ID NO. 1.

8. A recombinant nucleotide expression vector encoding human IDS, wherein said recombinant nucleotide expression vector when used to transduce a primary human neuronal cell in culture directs the expression of a secreted glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

9. A recombinant nucleotide expression vector encoding human IDS, which recombinant nucleotide expression vector is suitable for administration to the cerebrospinal fluid (CSF) of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

10. The recombinant nucleotide expression vector of paragraph 9, in which secretion of said glycosylated human IDS precursor is confirmed by transducing a human neuronal cell line with said recombinant nucleotide expression vector in cell culture.

11. The recombinant nucleotide expression vector of paragraph 9 or 10, in which secretion of said glycosylated human IDS precursor is confirmed in the presence and absence of mannose-6-phosphate.

12. The recombinant nucleotide expression vector of any one of paragraphs 8 to 11, in which the human IDS comprises the amino acid sequence of SEQ ID NO. 1.

13. The recombinant nucleotide expression vector of any one of paragraphs 8 to 12, which comprises a neuron-specific promoter that controls the expression of the glycosylated human IDS precursor in human neuronal cells or a glial cell-specific promoter that controls the expression of the glycosylated human IDS precursor in human glial cells.

14. The recombinant nucleotide expression vector of any one of paragraphs 8 to 13, which encodes a leader peptide that ensures proper co- and post-translational processing of the glycosylated human IDS precursor in human neuronal cells or human glial cells.

15. The recombinant nucleotide expression vector of any one of paragraphs 8 to 14, which is an AAV vector.

16. The recombinant nucleotide expression vector of paragraph 15, which is a replication defective AAV vector.

17. The recombinant nucleotide expression vector of paragraph 15 or 16, which is an AAV9 or AAVrh10 vector.

18. A formulation comprising a recombinant nucleotide expression vector encoding human IDS, wherein the formulation is suitable for administration to the CSF of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

19. A kit comprising a recombinant nucleotide expression vector encoding human IDS and a pharmaceutically acceptable carrier, wherein the recombinant nucleotide expression vector is suitable for administration to the cerebrospinal fluid (CSF) of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

20. A kit comprising a formulation comprising a recombinant nucleotide expression vector encoding human IDS, wherein the formulation is suitable for administration to the CSF of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

3.1.2. Set 2

1. Glycosylated recombinant human iduronate-2-sulfatase (IDS) precursor for use in the treatment of a human subject diagnosed with mucopolysaccharidosis type II (MPS II), wherein the glycosylated recombinant human IDS precursor is produced by human neuronal or human glial cells, and wherein the treatment comprises delivering to the cerebrospinal fluid (CSF) of said human subject a therapeutically effective amount of the glycosylated recombinant human IDS precursor.

2. The glycosylated recombinant human IDS precursor for use of paragraph 1, wherein the glycosylated recombinant human IDS precursor is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis.

3. The glycosylated recombinant human IDS precursor for use of paragraph 1, wherein the glycosylated recombinant human IDS precursor is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

4. The glycosylated recombinant human IDS precursor for use of any one of paragraphs 1 to 3, wherein the glycosylated recombinant human IDS precursor is secreted from a depot of cells in the central nervous system genetically engineered to secrete said glycosylated recombinant human IDS precursor.

5. The glycosylated recombinant human IDS precursor for use of paragraph 4, in which the depot is formed in a human subject's brain.

6. The glycosylated recombinant human IDS precursor for use of any one of paragraphs 1 to 5, in which the human subject is deficient in IDS activity.

7. The glycosylated recombinant human IDS precursor for use of any one of paragraphs 1 to 6, in which the glycosylated recombinant human IDS precursor comprises the amino acid sequence of SEQ ID NO. 1.

8. A recombinant nucleotide expression vector encoding human IDS for use in the treatment of a human subject diagnosed with MPS II, wherein said recombinant nucleotide expression vector when used to transduce a primary human neuronal cell in culture directs the expression of a secreted glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated, and wherein the treatment comprises administering to the CSF of said human subject the recombinant nucleotide expression vector.

9. A recombinant nucleotide expression vector encoding human IDS for use in the treatment of a human subject diagnosed with MPS II, wherein the recombinant nucleotide expression vector is suitable for administration to the cerebrospinal fluid of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated, and wherein the treatment comprises administering to the CSF of said human subject the recombinant nucleotide expression vector.

10. The recombinant nucleotide expression vector for use of paragraph 9, wherein secretion of said glycosylated human IDS precursor is confirmed by transducing a human neuronal cell line with said recombinant nucleotide expression vector in cell culture.

11. The recombinant nucleotide expression vector for use of paragraph 9 or 10, wherein secretion of said glycosylated human IDS precursor is confirmed in the presence and absence of mannose-6-phosphate.

12. The recombinant nucleotide expression vector for use of any one of paragraphs 8 to 11, in which the human IDS comprises the amino acid sequence of SEQ ID NO. 1.

13. The recombinant nucleotide expression vector for use of any one of paragraphs 8 to 12, wherein the recombinant nucleotide expression vector comprises a neuron-specific promoter that controls the expression of the glycosylated human IDS precursor in human neuronal cells or a glial cell-specific promoter that controls the expression of the glycosylated human IDS precursor in human glial cells.

14. The recombinant nucleotide expression vector for use of any one of paragraphs 8 to 13, wherein the recombinant nucleotide expression vector encodes a leader peptide that ensures proper co- and post-translational processing of the glycosylated human IDS precursor in human neuronal cells or human glial cells.

15. The recombinant nucleotide expression vector for use of any one of paragraphs 8 to 14, wherein the recombinant nucleotide expression vector is an AAV vector.

16. The recombinant nucleotide expression vector for use of paragraph 15, wherein the recombinant nucleotide expression vector is a replication defective AAV vector. 17. The recombinant nucleotide expression vector for use of paragraph 15 or 16, wherein the recombinant nucleotide expression vector is an AAV9 or AAVrh10 vector.

18. The recombinant nucleotide expression vector for use of any one of paragraphs 8 to 17, wherein the recombinant nucleotide expression vector is delivered to the CSF of the human subject by intrathecal, intracerebroventricular, lumbar puncture or intranasal administration.

19. The recombinant nucleotide expression vector for use of any one of paragraphs 8 to 18, wherein the human subject is deficient in IDS activity.

20. A formulation for use in the treatment of a human subject diagnosed with MPS II, which comprises a recombinant nucleotide expression vector encoding human IDS, wherein the formulation is suitable for administration to the CSF of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

3.1.3. Set 3

1. Use of a glycosylated recombinant human iduronate-2-sulfatase (IDS) precursor for the manufacture of a medicament for the treatment of a human subject diagnosed with mucopolysaccharidosis type II (MPS II), wherein the glycosylated recombinant human IDS precursor is produced by human neuronal or human glial cells, and wherein the treatment comprises delivering to the cerebrospinal fluid (CSF) of said human subject a therapeutically effective amount of the glycosylated recombinant human IDS precursor.

2. The use of paragraph 1, wherein the glycosylated recombinant human IDS precursor is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis.

3. The use of paragraph 1, wherein the glycosylated recombinant human IDS precursor is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

4. The use of any one of paragraphs 1 to 3, wherein the glycosylated recombinant human IDS precursor is secreted from a depot of cells in the central nervous system genetically engineered to secrete said glycosylated recombinant human IDS precursor.

5. The use of paragraph 4, in which the depot is formed in a human subject's brain.

6. The use of any one of paragraphs 1 to 5, in which the human subject is deficient in IDS activity.

7. The use of any one of paragraphs 1 to 6, in which the glycosylated recombinant human IDS precursor comprises the amino acid sequence of SEQ ID NO. 1.

8. Use of a recombinant nucleotide expression vector encoding human IDS for the manufacture of a medicament for the treatment of a human subject diagnosed with MPS II, wherein said recombinant nucleotide expression vector when used to transduce a primary human neuronal cell in culture directs the expression of a secreted glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated, and wherein the treatment comprises administering to the CSF of said human subject the recombinant nucleotide expression vector.

9. Use of a recombinant nucleotide expression vector encoding human IDS for the manufacture of a medicament for the treatment of a human subject diagnosed with MPS II, wherein the recombinant nucleotide expression vector is suitable for administration to the cerebrospinal fluid of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated, and wherein the treatment comprises administering to the CSF of said human subject the recombinant nucleotide expression vector.

10. The use of paragraph 9, wherein secretion of said glycosylated human IDS precursor is confirmed by transducing a human neuronal cell line with said recombinant nucleotide expression vector in cell culture.

11. The use of paragraph 9 or 10, wherein secretion of said glycosylated human IDS precursor is confirmed in the presence and absence of mannose-6-phosphate.

12. The use of any one of paragraphs 8 to 11, in which the human IDS comprises the amino acid sequence of SEQ ID NO. 1.

13. The use of any one of paragraphs 8 to 12, wherein the recombinant nucleotide expression vector comprises a neuron-specific promoter that controls the expression of the glycosylated human IDS precursor in human neuronal cells or a glial cell-specific promoter that controls the expression of the glycosylated human IDS precursor in human glial cells.

14. The use of any one of paragraphs 8 to 13, wherein the recombinant nucleotide expression vector encodes a leader peptide that ensures proper co- and post-translational processing of the glycosylated human IDS precursor in human neuronal cells or human glial cells.

15. The use of any one of paragraphs 8 to 14, wherein the recombinant nucleotide expression vector is an AAV vector.

16. The use of paragraph 15, wherein the recombinant nucleotide expression vector is a replication defective AAV vector.

17. The use of paragraph 15 or 16, wherein the recombinant nucleotide expression vector is an AAV9 or AAVrh10 vector.

18. The use of any one of paragraphs 8 to 17, wherein the recombinant nucleotide expression vector is delivered to the CSF of the human subject by intrathecal, intracerebroventricular, lumbar puncture or intranasal administration.

19. The use of any one of paragraphs 8 to 18, wherein the human subject is deficient in IDS activity.

20. Use of a formulation for the manufacture of a medicament for the treatment of a human subject diagnosed with MPS II, wherein the formulation comprises a recombinant nucleotide expression vector encoding human IDS, and wherein the formulation is suitable for administration to the CSF of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

3.1.4. Set 4

1. A method for treating a human subject diagnosed with mucopolysaccharidosis type II (MPS II), comprising delivering to the cerebrospinal fluid (CSF) of said human subject a therapeutically effective amount of a glycosylated recombinant human iduronate-2-sulfatase (IDS) precursor produced by human neuronal or human glial cells.

2. The method of paragraph 1, wherein the glycosylated recombinant human IDS precursor is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis.

3. The method of paragraph 1, wherein the glycosylated recombinant human IDS precursor is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

4. The method of any one of paragraphs 1 to 3, wherein the glycosylated recombinant human IDS precursor is secreted from a depot of cells in the central nervous system genetically engineered to secrete said glycosylated recombinant human IDS precursor.

5. The method of paragraph 4, in which the depot is formed in a human subject's brain.

6. The method of any one of paragraphs 1 to 5, in which the human subject is deficient in IDS activity.

7. The method of any one of paragraphs 1 to 6, in which the glycosylated recombinant human IDS precursor comprises the amino acid sequence of SEQ ID NO. 1.

8. A method for treating a human subject diagnosed with MPS II, comprising administering to the CSF of said human subject a recombinant nucleotide expression vector encoding human IDS, wherein said recombinant nucleotide expression vector when used to transduce a primary human neuronal cell in culture directs the expression of a secreted glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

9. A method for treating a human subject diagnosed with MPS II, comprising administering to the CSF of said human subject a recombinant nucleotide expression vector encoding human IDS, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

10. The method of paragraph 9, wherein secretion of said glycosylated human IDS precursor is confirmed by transducing a human neuronal cell line with said recombinant nucleotide expression vector in cell culture.

11. The method of paragraph 9 or 10, wherein secretion of said glycosylated human IDS precursor is confirmed in the presence and absence of mannose-6-phosphate.

12. The metho of any one of paragraphs 8 to 11, in which the human IDS comprises the amino acid sequence of SEQ ID NO. 1.

13. The method of any one of paragraphs 8 to 12, wherein the recombinant nucleotide expression vector comprises a neuron-specific promoter that controls the expression of the glycosylated human IDS precursor in human neuronal cells or a glial cell-specific promoter that controls the expression of the glycosylated human IDS precursor in human glial cells.

14. The method of any one of paragraphs 8 to 13, wherein the recombinant nucleotide expression vector encodes a leader peptide that ensures proper co- and post-translational processing of the glycosylated human IDS precursor in human neuronal cells or human glial cells.

15. The method of any one of paragraphs 8 to 14, wherein the recombinant nucleotide expression vector is an AAV vector.

16. The method of paragraph 15, wherein the recombinant nucleotide expression vector is a replication defective AAV vector.

17. The method of paragraph 15 or 16, wherein the recombinant nucleotide expression vector is an AAV9 or AAVrh10 vector.

18. The method of any one of paragraphs 8 to 17, wherein the recombinant nucleotide expression vector is delivered to the CSF of the human subject by intrathecal, intracerebroventricular, lumbar puncture or intranasal administration.

19. The method of any one of paragraphs 8 to 18, wherein the human subject is deficient in IDS activity.

20. A method for treating a human subject diagnosed with MPS II, comprising administering to the CSF of said human subject a formulation comprising a recombinant nucleotide expression vector encoding human IDS, wherein the formulation is suitable for administration to the CSF of human brain, so that a depot is formed in the human central nervous system that secretes a glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated.

3.1.5. Set 5

1. A method for treating a human subject diagnosed with mucopolysaccharidosis type II (MPS II), comprising delivering to the cerebrospinal fluid (CSF) of said human subject a therapeutically effective amount of a glycosylated recombinant human iduronate-2-sulfatase (IDS) precursor produced by human neuronal or human glial cells.

2. A method of treating a human subject diagnosed with mucopolysaccharidosis type II (MPS II), comprising:
delivering to the cerebrospinal fluid (CSF) of said human subject, a therapeutically effective amount of a glycosylated recombinant human iduronate-2-sulfatase (IDS) precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated, does not contain detectable NeuGc, and is mannose-6-phosphorylated.

3. A method of treating a human subject diagnosed with mucopolysaccharidosis type II (MPS II), comprising:
delivering to the cerebrospinal fluid (CSF) of said human subject, a therapeutically effective amount of a glycosylated recombinant human iduronate-2-sulfatase (IDS) precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated, does not contain detectable NeuGc and/or α-Gal antigen, and is mannose-6-phosphorylated.

4. The method of any one of paragraphs 1 to 3, in which the glycosylated recombinant human IDS precursor is delivered to the CSF from a depot of cells in the central nervous system genetically engineered to secrete said glycosylated recombinant human IDS precursor into the CSF.

5. The method of paragraph 4, in which the depot is formed in the human subject's brain.

6. The method of any one of paragraphs 1 to 5, in which the human subject is deficient in IDS activity.

7. The method of any one of paragraphs 1 to 6, in which the glycosylated recombinant human IDS precursor comprises the amino acid sequence of SEQ ID NO. 1.

8. A method of treating a human subject diagnosed with mucopolysaccharidosis type II (MPS II), comprising administering to the cerebrospinal fluid (CSF) of said human subject a recombinant nucleotide expression vector encoding human iduronate-2-sulfatase (IDS), wherein said recombinant nucleotide expression vector when used to transduce a primary human neuronal cell in culture directs the expression of a secreted glycosylated human IDS precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated and mannose-6-phosphorylated.

9. A method of treating a human subject diagnosed with mucopolysaccharidosis type II (MPS II), comprising:
administering to the cerebrospinal fluid of the brain of said human subject, a therapeutically effective amount of a recombinant nucleotide expression vector encoding human IDS, so that a depot is formed in the subject's central nervous system that secretes a glycosylated human IDS precursor that is α2,6-sialylated and mannose-6-phosphorylated.

10. The method of paragraph 9, in which secretion of said glycosylated human IDS precursor that is α2,6-sialylated is confirmed by transducing a human neuronal cell line with said recombinant nucleotide expression vector in cell culture.

11. The method of paragraph 9, in which secretion of said glycosylated human IDS precursor that is mannose-6-phosphorylated is confirmed by transducing a human neuronal cell line with said recombinant nucleotide expression vector in cell culture.

12. The method of paragraph 10 or 11, in which secretion is confirmed in the presence and absence of mannose-6-phosphate.

13. A method of treating a human subject diagnosed with mucopolysaccharidosis type II (MPS II), comprising:
administering to the cerebrospinal fluid of the brain of said human subject, a therapeutically effective amount of a recombinant nucleotide expression vector encoding human IDS, so that a depot is formed that secretes a glycosylated human IDS precursor containing a α2,6-sialylated glycan;
wherein said recombinant nucleotide expression vector, when used to transduce human neuronal cells in culture results in secretion of said glycosylated human IDS precursor containing a α2,6-sialylated glycan in said cell culture.

14. A method of treating a human subject diagnosed with mucopolysaccharidosis type II (MPS II), comprising:
administering to the cerebrospinal fluid of the brain of said human subject, a therapeutically effective amount of a recombinant nucleotide expression vector encoding human IDS, so that a depot is formed that secretes a glycosylated human IDS precursor that contains a mannose-6-phosphate;

wherein said recombinant nucleotide expression vector, when used to transduce human neuronal cells in culture results in secretion of said glycosylated human IDS precursor that is mannose-6-phosphorylated in said cell culture.

15. A method of treating a human subject diagnosed with mucopolysaccharidosis type II (MPS II), comprising:

administering to the cerebrospinal fluid of the brain of said human subject, a therapeutically effective amount of a recombinant nucleotide expression vector encoding human IDS, so that a depot is formed that secretes a glycosylated human IDS precursor that contains a formylglycine;

wherein said recombinant nucleotide expression vector, when used to transduce human neuronal cells in culture results in secretion of said glycosylated human IDS precursor that contains a formylglycine in said cell culture.

16. The method of any one of paragraphs 8 to 15, in which the human IDS comprises the amino acid sequence of SEQ ID NO. 1.

17. The method of any one of paragraphs 8 to 15, wherein the recombinant nucleotide expression vector encodes a leader peptide.

18. The method of any one of paragraphs 8 to 15, in which the recombinant nucleotide expression vector is a replication defective AAV vector.

19. The method of any one of paragraphs 8 to 15, in which the recombinant nucleotide expression vector is delivered to the CSF of the human subject by intrathecal, intracerebroventricular, lumbar puncture or intranasal administration.

20. The method of any one of paragraphs 8 to 15, in which the human subject is deficient in IDS activity.

4. BRIEF DESCRIPTION OF THE DRAWINGS

FIG. 1. The amino acid sequence of human IDS (SEQ ID NO: 1). A post-translational formylglycine modification of $C^{84}$ (shown in bold in FIG. 1) is required for enzyme activity. Eight N linked glycosylation sites ($N^{31}$, $N^{115}$, $N^{144}$, $N^{246}$, $N^{280}$, $N^{325}$, $N^{513}$ and $N^{537}$) are bold and boxed. One tyrosine-O-sulfation site (Y) is bold and the full sulfation site sequence (PSSEKY$^{165}$ENTKTCRGPD; SEQ ID NO: 45) is boxed. The N-terminus of the mature 42 kDa and mature 14 kDa polypeptides are indicated by horizontal arrows. In the brain, the N-terminus of the mature 42 kDa form starts at positions 34 or 36 as follows: $T^{34}$DALNVLLI (SEQ ID NO: 46); and $A^{36}$LNVLLIIV (SEQ ID NO: 47) as indicated in FIG. 1. (See, Sleat, 2005, Proteomics 5: 1520-1532, Table S2). Two of the eight N-linked glycosylation sites, namely $N^{280}$ and $N^{116}$, are mannose-6-phophorylated in IDS obtained from human brain. (Sleat et al., 2006, Mol & Cell Proeomics 5.4: 686-701, reported at Table V).

FIG. 2. Multiple sequence alignment of hIDS with known orthologs. The names of the species and protein IDs are as follows: SP|P22304|IDS_HUMAN [*Homo sapiens*]; TR|K6ZGI9_PANTR [*Pan troglodytes* (Chimpanzee)]; TR|K7BKV4_PANTR [*Pan troglodytes* (Chimpanzee)]; TR|H9FTX2_MACMU [*Macaca mulatta* (Rhesus macaque)]; TRF7EJG2 CALJA [*Callithrix jacchus* (White-tufted-ear marmoset)]; TR|U3DTL8_CALJA [*Callithrix jacchus* (White-tufted-ear marmoset)]; TR|G7NRX7_MACMU [*Macaca mulatta* (Rhesus macaque)]; TR|G7Q1V9_MACFA [*Macaca fascicularis* (Crab-eating macaque; Cynomologous monkey)]; TR|H2PX10_PONAB [*Pongo abelii* (Sumatran orang-utan)]; TR|A0A0D9R4D1_CHLSB [*Chlorocebus sabaeus* (Green monkey)]; TR|G1RST81G1RST8_NOMLE [*Nomascus leucogenys* (Northern white-cheeked gibbon)]; UPI0000D9F625 [*Macaca mulatta* (Rhesus macaque)]; UPI000274358B [*Pan paniscus* (Pygmy chimpanzee; Bonobo)]; UPI00027F6FC5 [*Papio anubis* (Olive baboon)]; UPI00027FAE03 [*Saimiri boliviensis* (Bolivian squirrel monkey)]; UPI0003ABBF28 [*Macaca fascicularis* (Crab-eating macaque; Cynomologous monkey)]; UPI000533297F [*Rhinopithecus roxellana* (Golden snub-nosed monkey; Pygathrix roxellana)]; UPI0005F40BD2 [*Colobus angolensis* palliates (Peters' Angolan colobus)] (SEQ ID NOs: 27-44).

FIG. 3. MPS II mutations in hIDS and corresponding disease phenotypes, mild, intermediate or severe. (from Uniprot).

FIG. 4. Human IDS processing as reported in Millat et al., 1997, Exp. Cell. Res. 230: 362-367, at FIG. 7.

Figure 5:
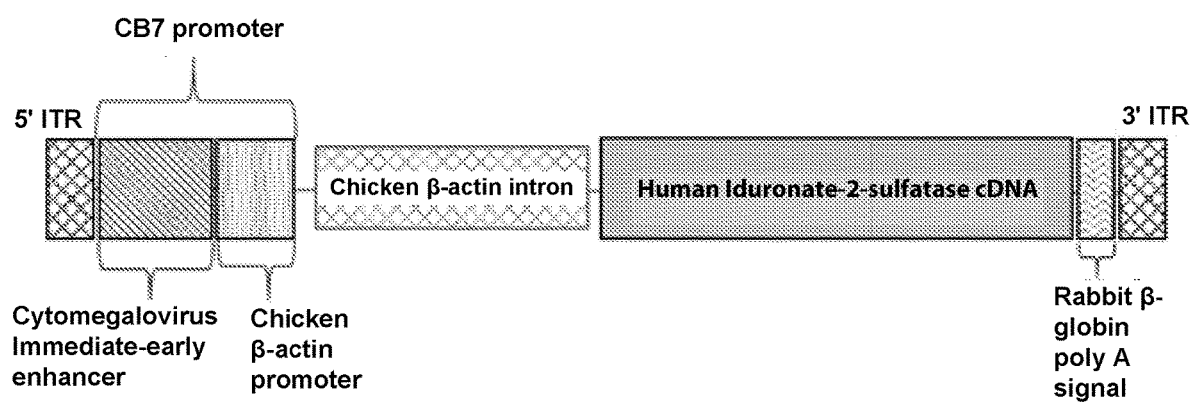

FIG. 5. Schematic Representation of Construct 1.

FIG. 6. Clustal Multiple Sequence Alignment of AAV capsids 1-9 (SEQ ID NOs: 16-26). Amino acid substitutions (shown in bold in the bottom rows) can be made to AAV9 and AAV8 capsids by "recruiting" amino acid residues from the corresponding position of other aligned AAV capsids. Sequence regions designated by "HVR"=hypervariable regions.

5. DETAILED DESCRIPTION OF THE INVENTION

The invention involves the delivery of recombinant human iduronate-2-sulfatase (rhIDS) produced by human neuronal or glial cells to the cerebrospinal fluid (CSF) of the central nervous system (CNS) of a human subject diagnosed with mucopolysaccharidosis II (MPS II), including, but not limited to patients diagnosed with Hunter syndrome. See, also, International Patent Application No. PCT/US2017/027770, filed Apr. 14, 2017 (published as WO/2017/181113 on Oct. 19, 2017), which is incorporated by reference herein in its entirety, for compositions and methods that can be used according to the invention described herein.

In a preferred embodiment, the treatment is accomplished via gene therapy—e.g., by administering a viral vector or other DNA expression construct encoding human IDS (hIDS), or a derivative of hIDS, to the CSF of a patient (human subject) diagnosed with MPS II, so that a permanent depot of transduced neuronal and/or glial cells is generated that continuously supplies the transgene product to the CNS. The rhIDS secreted from the neuronal/glial cell depot into the CSF will be endocytosed by cells in the CNS, resulting in "cross-correction" of the enzymatic defect in the recipient cells. Moreover, it has been found, unexpectedly, that the depot of transduced neural and glial cells in the CNS can deliver the recombinant enzyme to both the CNS and systemically, which may reduce or eliminate the need for systemic treatment, e.g., weekly i.v. injections of the enzyme.

In an alternative embodiment, the hIDS can be produced by human neuronal or glial cells in cell culture (e.g., bioreactors) and administered as an enzyme replacement therapy ("ERT"), e.g., by injecting the enzyme—into the CSF, directly into the CNS, and/or systemically. However, the gene therapy approach offers several advantages over ERT since systemic delivery of the enzyme will not result in treating the CNS because the enzyme cannot cross the blood brain barrier; and, unlike the gene therapy approach of the invention, direct delivery of the enzyme to the CSF and/or CNS would require repeat injections which are not only burdensome, but pose a risk of infection.

The hIDS encoded by the transgene can include, but is not limited to human IDS (hIDS) having the amino acid sequence of SEQ ID NO. 1 (as shown in FIG. 1), and derivatives of hIDS having amino acid substitutions, deletions, or additions, e.g., including but not limited to amino acid substitutions selected from corresponding non-conserved residues in orthologs of IDS shown in FIG. 2, with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inhert Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety.

For example, amino acid substitutions at a particular position of hIDS can be selected from among corresponding non-conserved amino acid residues found at that position in the IDS orthologs aligned in FIG. 2, with the proviso that such substitutions do not include any of the deleterious mutations shown in FIG. 3 or as reported by Sukegawa-Hayasaka et al., 2006, supra; Millat et al., 1998, supra; or Bonucelli et al., 2001, supra, each of which is incorporated by reference herein in its entirety. The resulting transgene product can be tested using conventional assays in vitro, in cell culture or test animals to ensure that the mutation does not disrupt IDS function. Preferred amino acid substitutions, deletions or additions selected should be those that maintain or increase enzyme activity, stability or half-life of IDS, as tested by conventional assays in vitro, in cell culture or animal models for MPS II. For example, the enzyme activity of the transgene product can be assessed using a conventional enzyme assay with, for example, 4-Methylumbelliferyl α-L-idopyranosiduronic acid 2-sulfate or 4-methylumbelliferyl sulfate as the substrate (see, e.g., Lee et al., 2015, Clin. Biochem. 48(18):1350-1353, Dean et al., 2006, Clin. Chem. 52(4):643-649 for exemplary IDS enzyme assays that can be used, each of which is incorporated by reference herein in its entirety). The ability of the transgene product to correct MPS II phenotype can be assessed in cell culture; e.g., by transducing MPS II cells in culture with a viral vector or other DNA expression construct encoding hIDS or a derivative; by adding the transgene product or a derivative to MPS II cells in culture; or by co-culturing MPS II cells with human neuronal/glial host cells engineered to express and secrete rhIDS or a derivative, and determining correction of the defect in the MPS II cultured cells, e.g., by detecting IDS enzyme activity and/or reduction in GAG storage in the MPS II cells in culture (see, e.g., Stroncek et al., 1999, Transfusion 39(4):343-350, which is incorporated by reference herein in its entirety).

Animal models for MPS II have been described that can be used to assess the therapeutics described herein. For example, a knockout mouse model (IDS-knockout) of MPS II was engineered by replacing exons 4 and 5 of the IDS gene with the neomycin resistance gene. (Garcia et al., 2007, J Inherit Metab Dis 30: 924-34). This IDS-knockout mouse exhibits many of the characteristics of MPS II, including skeletal abnormalities, hepatosplenomegaly, elevated urinary and tissue GAG, and brain storage lesions (Muenzer et al., 2001, Acta Paediatr Suppl 91:98-99) and was used to assess the effect of enzyme replacement therapy in MPS II in support of clinical trials for ERT. This mouse model, therefore, is a relevant model for studying the effects of gene therapy delivering rIDS produced by neuronal or glial cells as a treatment for MPS II (see, e.g., Polito and Cosma, 2009, Am. J. Hum. Genet. 85(2):296-301, which is incorporated by reference herein in its entirety).

Preferably, the hIDS transgene produced by the human neuronal/glial cells should be controlled by expression control elements that function in neurons and/or glial cells, e.g., the CB7 promoter (a chicken β-actin promoter and CMV enhancer), and can include other expression control elements that enhance expression of the transgene driven by the vector (e.g., chicken β-actin intron and rabbit β-globin poly A signal). The cDNA construct for the hIDS transgene should include a coding sequence for a signal peptide that ensures proper co- and post-translational processing (glycosylation and protein sulfation) by the transduced CNS cells. Such signal peptides used by CNS cells may include but are not limited to:

```
Oligodendrocyte-myelin glycoprotein (hOMG) signal
peptide:
                                          (SEQ ID NO: 2)
MEYQILKMSLCLFILLFLTPGILC Cellular repressor of E1A-stimulated genes 2
(hCREG2) signal peptide:
                                          (SEQ ID NO: 3)
MSVRRGRRPARPGTRLSWLLCCSALLSPAAG V-set and transmembrane domain containing 2B
(hVSTM2B) signal peptide:
                                          (SEQ ID NO: 4)
MEQRNRLGALGYLPPLLLHALLLFVADA Protocadherin alpha-1 (hPCADHA1) signal peptide:
                                          (SEQ ID NO: 5)
MVFSRRGGLGARDLLLWLLLLAAWEVGSG FAM19A1 (TAFA1) signal peptide:
                                          (SEQ ID NO: 6)
MAMVSAMSWVLYLWISACA Interleukin-2 signal peptide:
                                          (SEQ ID NO: 14)
MYRMQLLSCIALILALVTNS
```

Signal Peptides May Also be Referred to Herein as Leader Sequences or Leader Peptides.

The recombinant vector used for delivering the transgene should have a tropism for cells in the CNS, including but limited to neurons and/or glial cells. Such vectors can include non-replicating recombinant adeno-associated virus vectors ("rAAV"), particularly those bearing an AAV9 or AAVrh10 capsid are preferred. AAV variant capsids can be used, including but not limited to those described by Wilson in U.S. Pat. No. 7,906,111 which is incorporated by reference herein in its entirety, with AAV/hu.31 and AAV/hu.32 being particularly preferred; as well as AAV variant capsids described by Chatterjee in U.S. Pat. Nos. 8,628,966, 8,927, 514 and Smith et al., 2014, Mol Ther 22: 1625-1634, each of which is incorporated by reference herein in its entirety. However, other viral vectors may be used, including but not limited to lentiviral vectors, vaccinia viral vectors, or non-viral expression vectors referred to as "naked DNA" constructs.

Pharmaceutical compositions suitable for administration to the CSF comprise a suspension of the rhIDS vector in a formulation buffer comprising a physiologically compatible aqueous buffer, a surfactant and optional excipients. In certain embodiments, the pharmaceutical compositions are suitable for intrathecal administration. In certain embodiments, the pharmaceutical compositions are suitable for intracisternal administration (injection into the cisterna magna). In certain embodiments, the pharmaceutical compositions are suitable for injection into the subarachnoid space via a C1-2 puncture. In certain embodiments, the pharmaceutical compositions are suitable for intracerebroventricular administration. In certain embodiments, the pharmaceutical compositions are suitable for administration via lumbar puncture.

Therapeutically effective doses of the recombinant vector should be administered to the CSF via intrathecal administration (i.e., injection into the subarachnoid space so that the recombinant vectors distribute through the CSF and transduce cells in the CNS). This can be accomplished in a number of ways—e.g., by intracranial (cisternal or ventricular) injection, or injection into the lumbar cistern. For example intracisternal (IC) injection (into the cisterna magna) can be performed by CT-guided suboccipital puncture; or injection into the subarachnoid space can be performed via a C1-2 puncture when feasible for the patient; or lumbar puncture (typically diagnostic procedures performed in order to collect a sample of CSF) can be used to access the CSF. Alternatively, intracerebroventricular (ICV) administration (a more invasive technique used for the introduction of antiinfective or anticancer drugs that do not penetrate the blood-brain barrier) can be used to instill the recombinant vectors directly into the ventricles of the brain. Alternatively, intranasal administration may be used to deliver the recombinant vector to the CNS.

Because of the relatively rapid brain growth that occurs early in a developing child, the total dose of AAV9.hIDS administered IC depends on the assumed brain mass across different age strata. For brain mass by age for the study subjects see, eg., (A S Dekaban, Ann Neurol, 1978 October; 4(4): 345-56.

TABLE

Total dose administered by age

| Subject Age | Assumed brain mass (g) | Dose 1 (total GC) | Dose 2 (total GC) |
| --- | --- | --- | --- |
| ≥4 to <9 months | 600 | $7.8 \times 10^{12}$ | $3.9 \times 10^{13}$ |
| ≥9 to <18 months | 1000 | $1.3 \times 10^{13}$ | $6.5 \times 10^{13}$ |
| ≥18 months to <3 years | 1100 | $1.4 \times 10^{13}$ | $7.2 \times 10^{13}$ |
| ≥3 years | 1300 | $1.7 \times 10^{13}$ | $8.5 \times 10^{13}$ |

CSF concentrations can be monitored by directly measuring the concentration of rhIDS in the CSF fluid obtained from occipital or lumbar punctures, or estimated by extrapolation from concentrations of the rhIDS detected in the patient's serum.

By way of background, human IDS is translated as a 550 amino acid polypeptide that contains eight potential N-glycosylation sites ($N^{31}$, $N^{115}$, $N^{144}$, $N^{246}$, $N^{280}$, $N^{325}$, $N^{513}$ and $N^{537}$) depicted in FIG. 1 and includes a 25 amino acid signal sequence which is cleaved during processing. An initial 76 kDa intracellular precursor is converted into a phosphorylated 90 kDa precursor after modification of its oligosaccharide chains in the Golgi apparatus. This precursor is processed by glycosylation modifications and proteolytic cleavage through various intracellular intermediates to a major 55 kDa form. To summarize, after removal of the 25 aa signal sequence, proteolytic processing involves N-terminal proteolytic cleavage downstream of $N^{31}$ removing a propeptide of eight amino acids (residues 26-33), and C-terminal proteolytic cleavage upstream of $N^{513}$ which releases an 18 kDa polypeptide and produces a 62 kDa intermediate that is converted to a 55 kDa mature form. Further proteolytic cleavage yields a 45 kDa mature form located in the lysosomal compartment. (See FIG. 4 for diagram reproduced from Millat et al., 1997, Exp Cell Res 230: 362-367 ("Millat 1997"); Millat et al. 1997, Biochem J. 326: 243-247 ("Millat 1997a"); and Froissart et al., 1995, Biochem J. 309:425-430, each of which is incorporated by reference herein in its entirety).

A formylglycine modification of $C^{84}$ (shown in bold in FIG. 1) required for enzyme activity probably occurs as an early post-translational or co-translational event, most probably in the endoplasmic reticulum. (See, Millat 1997a, citing Schmidt et al., 1995, Cell 82: 271-278). Post-translational processing continues in the Golgi to include addition of complex sialic acid-containing glycans and acquisition of mannose-6-phosphate residues which tag the enzyme for delivery to the lysosomal compartment. (See, Clarke, 2008, Expert Opin Pharmacother 9: 311-317 for a concise review which is incorporated by reference herein in its entirety). While no single glycosylation site is essential for IDS stability, glycosylation at position $N^{280}$ is important for cellular internalization and lysosomal targeting via the mannose-6-phosphate (M6P) receptor. (Chung et al., 2014, Glycoconj J 31:309-315 at p. 310, first column). In the normal physiologic state, IDS is produced at very low levels and very little, if any, enzyme is secreted from the cell. (Clarke, 2008, supra).

The invention is based, in part, on the following principles:

(i) Neuronal and glial cells in the CNS are secretory cells that possess the cellular machinery for post-translational processing of secreted proteins—including glycosylation, mannose-6-phosphorylation, and tyrosine-O-sulfation—robust processes in the CNS. See, e.g., Sleat et al., 2005, Proteomics 5: 1520-1532, and Sleat 1996, J Biol Chem 271: 19191-98 which describes the human brain mannose-6-phosphate glycoproteome and notes that the brain contains more proteins with a much greater number of individual isoforms and mannose-6-phosphorylated proteins than found in other tissues; and Kanan et al., 2009, Exp. Eye Res. 89: 559-567 and Kanan & Al-Ubaidi, 2015, Exp. Eye Res. 133: 126-131 reporting the production of tyrosine-sulfated glycoproteins secreted by neuronal cells, each of which is incorporated by reference in its entirety for post-translational modifications made by human CNS cells.

(ii) The human brain produces multiple isoforms of natural/native IDS. In particular, N-terminal sequencing of human brain mannose-6-phosphorylated glycoproteins revealed that the N-terminal sequence of the mature 42 kDa chain of hIDS varies in the brain, starting at positions 34 or 36 as follows: $T^{34}$DALNVLLI; and $A^{36}$LNVLLIIV. (Sleat, 2005, Proteomics 5: 1520-1532, Table S2). Two of the eight N-linked glycosylation sites, namely $N^{280}$ and $N^{116}$, were found to be mannose-6-phophorylated in IDS obtained from human brain. (Sleat et al., 2006, Mol & Cell Proeomics 5.4: 686-701, reported at Table V).

(iii) During processing of hIDS, two polypeptides, 76 kDa and 90 kDa, are secreted by neural and glial cells, but only the 90 kDa polypeptide is mannose-6-phosphorylated, which is necessary for secreted forms of the enzyme to achieve cross correction. (See, Millat, 1997, FIG. 1 results for transduced lymphoblastoid cells, and Froissart 1995, FIG. 4 showing similar results for transduced fibroblasts—in culture medium, only the 90 kDa form is phosphorylated). Interestingly, it has been demonstrated that recombinant IDS produced by neuronal and glial cells may be endocytosed by recipient CNS cells more avidly than recombinant IDS produced by other cells such as kidney. Daniele 2002 demonstrated M6P-receptor mediated endocytosis of recombinant IDS from conditioned media of transduced neuronal and glial cell cultures by a recipient population of non-transduced neuronal and glial cells which properly processed the precursor to the 45 kDa mature active form. Uptake of the recombinant IDS produced by the neuronal and glial cell lines (74% endocytosis) far exceeded uptake of the enzyme produced by a kidney cell line (5.6% endocytosis). In each case, uptake was inhibited by M6P, indicating that recombinant IDS uptake was M6P-receptor mediated. (See Daniele 2002, Tables 2 and 4 and accompanying description in Results at pp. 205-206 summarized in Table 1 below).

TABLE 1

Summary of Results Reported in Daniele 2002

| Cell Line Source of rIDS | Media Enzyme Units | Recipient Cells: Units Recovered | | % Endocytosis (mean value) |
| --- | --- | --- | --- | --- |
| | | Neuronal | Glial | |
| Kidney$^{(transfected)}$ | 35 U | 1.7 U | 2.2 U | 5.6% |
| Neuronal$^{(Ad-tansduced)}$ | 12 U | 8.8 U | 8.8 U | 74% |
| Glial$^{(Ad-transduced)}$ | 14 U | 10.5 U | 10.5 U | 74% |

(iv) The gene therapy approach described herein should result in the continuous secretion of an hIDS glycoprotein precursor of about 90 kDa as measured by polyacrylamide gel electrophoresis (depending on the assay used) that is enzymatically active. First, the enzyme responsible for the formylglycine modification of $C^{84}$ which is required for IDS activity—the FGly-Generating Enzyme (FGE, aka SUMF1)—is expressed in the cerebral cortex of the human brain (gene expression data for SUMF1 may be found, for example, at GeneCards, accessible at http://www.genecards.org). Second, the secreted glycosylated/phosphorylated rIDS produced by transduced neurons and glial cells in situ should be taken up and correctly processed by untransduced neural and glial cells in the CNS. Without being bound to any theory, it appears that the secreted rhIDS precursor produced in situ by gene therapy may be more avidly endocytosed by recipient cells in the CNS than would traditional recombinant enzymes used for ERT if administered to the CNS. For example, Elaprase® (made in HT1080, a fibrosarcoma cell line) is a purified protein reported to have a molecular weight of about 76 kDa—not the 90 kDa species secreted by neuronal and glial cells that appears to be more heavily phosphorylated. While the eight N-linked glycosylation sites are reported to be fully occupied in Elaprase® and contain two bis-mannose-6-phosphate terminated glycans as well as complex highly sialylated glycans, the post-translational modification of $C^{84}$ to FGly, which is an absolute requirement for enzyme activity, is only about 50%. (Clarke, 2008, Expert Opin Pharmacother 9:311-317; Elaprase® Full Prescribing Information and EMA filing). Another recombinant product, Hunterase® is made in CHO cells. While reported to have higher FGly and activity than Elaprase®, mannose-6-phosphorylation and uptake did not differ. (Chung, 2014, Glycoconj J 31:309-315).

(v) The extracellular IDS efficacy in vivo depends on uptake (cell and lysosome internalization) through mannose-6-phosphate (M6P) and its active site formylglycine (FGly), which is converted from $C^{84}$ through post-translational modification by formylglycine-generating enzyme. As shown above in Table 1, brain cells (neuronal and glial cells) show higher enzyme activities when incubated with IDS precursor media secreted by transduced neuronal and glial cells than with IDS precursor media secreted by genetically engineered kidney cells. The resultant five-fold increase in activity can likely be attributed to the efficient uptake of IDS (See Daniele 2002, Tables 2 and 4). Commercial forms of IDS, which are generated by CHO cells or HT-1080 cells, have a FGly content of about 50% to 70%, which determines the enzyme activity. However, neuronal and glial cells may improve upon this activity, due to improvement of IDS uptake.

(vi) The cellular and subcellular trafficking/uptake of lysosomal proteins, including IDS, is through M6P. IDS from brain cells may contain higher M6P content, as reported in Daniele 2002, and in Sleat, Proteomics, 2005 (indicating that the human brain contains more (in both a quantitative and qualitative sense) Man6-P glycoproteins than other tissues). It is possible to measure the M6P content of an IDS precursor, as done in Daniele 2002. In the presence of inhibitory M6P (e.g., 5 mM), the uptake of IDS precursor generated by non-neuronal or non-glial cells, such as the genetically engineered kidney cells of Daniele 2002, is predicted to decrease to levels close to that of the control cells, as was shown in Daniele 2002. While in the presence of inhibitory M6P, the uptake of IDS precursor generated by brain cells, such as neuronal and glial cells, is predicted to remain at a high level, as was shown in Daniele 2002, where the uptake was four times higher than control cells and comparable to the level of IDS activity (or uptake) of IDS precursor generated by genetically engineered kidney cells without the presence of inhibitory M6P. This assay allows for a way to predict the M6P content in IDS precursor generated by brain cells, and, in particular, to compare the M6P content in IDS precursors generated by different types of cells. The gene therapy approach described herein should result in the continuous secretion of an hIDS precursor that may be taken up into neuronal and glial cells at a high level in the presence of inhibitory M6P in such an assay.

(vii) The M6P content and uptake of IDS precursor may also be demonstrated by 90 kDa and 76 kDa gel bands (e.g., SDS-PAGE gel bands). The 90 kDa is reported to be highly glycosylated/phosphorylated and contains M6P, while 76 kDa is not. A very broad gel band with a range from 76 kDa to 95 kDa and with an average MW of 80-85 kDa, similar to the IDS precursor gel band generated from genetically engineered kidney cells (Daniele 2002, FIG. 1), may be contrasted with a gel band of IDS precursor generated from brain cells. In Daniele 2002, the gel band cannot be obtained due to unsuccessful immunoprecipitation of the IDS precursor. The gene therapy approach described herein should result in the continuous secretion of an hIDS precursor that differs from the IDS precursor gel band generated from genetically engineered kidney cells.

(viii) The M6P content of commercial IDS precursor is 2 to 2.5 mol/mol, majority of which is present in a form of di-phosphorylated glycans. Although in average, every IDS precursor is phosphorylated, a normal distribution of glycans will have some IDS precursor with 2, 1 and 0 of di-phosphorylated M6P glycans assuming multiple phosphorylation sites. Uptake rate should be significant higher with multiple phosphorylation.

(ix) The glycosylation of hIDS by human cells of the CNS will result in the addition of glycans that can improve stability, half-life and reduce unwanted aggregation of the transgene product. Significantly, the glycans that are added to hIDS of the invention include 2,6-sialic acid, incorporating Neu5Ac ("NANA") but not its hydroxylated derivative, NeuGc (N-Glycolyl-neuraminic acid, i.e., "NGNA" or "Neu5Gc"). Such glycans are not present in recombinant IDS products, such as Hunterase®, made in CHO cells because CHO cells do not have the 2,6-sialyltransferase required to make this post-translational modification; nor do CHO cells produce bisecting GlcNAc, although they do add Neu5Gc (NGNA) as sialic acid not typical (and potentially immunogenic) to humans instead of Neu5Ac (NANA). See, e.g., Dumont et al., 2016, Critical Rev in Biotech 36(6):1110-1122 (Early Online pp. 1-13 at p. 5); and Hague et al., 1998 Electrophor 19:2612-2630 ("[t]he CHO cell line is considered 'phenotypically restricted,' in terms of glycosylation, due to the lack of an α2,6-sialyl-transferase"). Moreover, CHO cells can also produce an immunogenic glycan, the α-Gal antigen, which reacts with anti-α-Gal antibodies present in most individuals, and at high concentrations can trigger anaphylaxis. See, e.g., Bosques, 2010, Nat Biotech 28: 1153-1156. The human glycosylation pattern of the rhIDS of the invention should reduce immunogenicity of the transgene product and improve efficacy.

(x) Immunogenicity of a transgene product could be induced by various factors, including the immune condition of the patient, the structure and characteristics of the infused protein drug, the administration route, and the duration of treatment. Process-related impurities, such as host cell protein (HCP), host cell DNA, and chemical residuals, and product-related impurities, such as protein degradants and structural characteristics, such as glycosylation, oxidation and aggregation (sub-visible particles), may also increase immunogenicity by serving as an adjuvant that enhances the immune response. The amounts of process-related and product-related impurities can be affected by the manufacturing process: cell culture, purification, formulation, storage and handling, which can affect commercially manufactured IDS products. In gene therapy, proteins are produced in vivo, such that process-related impurities are not present and protein products are not likely to contain product-related impurities/degradants associated with proteins produced by recombinant technologies, such as protein aggregation and protein oxidation. Aggregation, for example, is associated with protein production and storage due to high protein concentration, surface interaction with manufacturing equipment and containers, and the purification process with certain buffer systems. But these conditions that promote aggregation are not present when a transgene is expressed in vivo. Oxidation, such as methionine, tryptophan and histidine oxidation, is also associated with protein production and storage, caused, for example, by stressed cell culture conditions, metal and air contact, and impurities in buffers and excipients. The proteins expressed in vivo may also oxidize in a stressed condition, but humans, like many organisms, are equipped with an antioxidation defense system, which not only reduces the oxidation stress, but can also repairs and/or reverses the oxidation. Thus, proteins produced in vivo are not likely to be in an oxidized form. Both aggregation and oxidation could affect the potency, pharmacokinetics (clearance) and can increase immunogenicity concerns. The gene therapy approach described herein should result in the continuous secretion of an hIDS precursor with a reduced immunogenicity compared to commercially manufactured products.

(xi) In addition to the N-linked glycosylation sites, hIDS contains a tyrosine ("Y") sulfation site (PSSEKY$^{165}$ENTKTCRGPD). (See, e.g., Yang et al., 2015, Molecules 20:2138-2164, esp. at p. 2154 which is incorporated by reference in its entirety for the analysis of amino acids surrounding tyrosine residues subjected to protein tyrosine sulfation. The "rules" can be summarized as follows: Y residues with E or D within +5 to −5 position of Y, and where position −1 of Y is a neutral or acidic charged amino acid—but not a basic amino acid, e.g., R, K, or H that abolishes sulfation). While not intending to be bound by any theory, sulfation of this site in hIDS may improve stability of the enzyme and binding affinity for substrate. Tyrosine-sulfation of hIDS—a robust post-translational process in human CNS cells—should result in improved processing and activity of transgene products. The significance of tyrosine-sulfation of lysosomal proteins has not been elucidated; but in other proteins it has been shown to increase avidity of protein-protein interactions (antibodies and receptors), and to promote proteolytic processing (peptide hormone). (See, Moore, 2003, J Biol. Chem. 278: 24243-46; and Bundegaard et al., 1995, The EMBO J 14: 3073-79). The tyrosylprotein sulfotransferase (TPST1) responsible for tyrosine-sulfation (which may occur as a final step in IDS processing) is apparently expressed at higher levels (based on mRNA) in the brain (gene expression data for TPST1 may be found, for example, at the EMBL-EBI Expression Atlas, accessible at http://www.ebi.ac.uk/gxa/home). Such post-translational modification, at best, is under-represented in CHO cell products. Unlike human CNS cells, CHO cells are not secretory cells and have a limited capacity for post-translational tyrosine-sulfation. (See, e.g., Mikkelsen & Ezban, 1991, Biochemistry 30: 1533-1537, esp. discussion at p. 1537).

For the foregoing reasons, the production of rhIDS by human neuronal and/or glial cells should result in a "biobetter" molecule for the treatment of MPS II accomplished via gene therapy—e.g., by administering a viral vector or other DNA expression construct encoding rhIDS to the CSF of a patient (human subject) diagnosed with an MPS II disease (including but not limited to Hunter) to create a permanent depot in the CNS that continuously supplies a fully human-glycosylated, mannose-6-phosphorylated, sulfated transgene product secreted by the transduced CNS cells. The hIDS transgene product secreted from the depot into the CSF will be endocytosed by cells in the CNS, resulting in "cross-correction" of the enzymatic defect in the MPS II recipient cells.

It is not essential that every rhIDS molecule produced either in the gene therapy or protein therapy approach be fully glycosylated, phosphorylated, and sulfated. Rather, the population of glycoproteins produced should have sufficient glycosylation (including 2,6-sialylation and mannose-6-phosphorylation) and sulfation to demonstrate efficacy. The goal of gene therapy treatment of the invention is to slow or arrest the progression of disease. Efficacy may be monitored by measuring cognitive function (e.g., prevention or decrease in neurocognitive decline); reductions in biomarkers of disease (such as GAG) in CSF and or serum; and/or increase in IDS enzyme activity in CSF and/or serum. Signs of inflammation and other safety events may also be monitored.

As an alternative, or an additional treatment to gene therapy, the rhIDS glycoprotein can be produced in human neural or glial cell lines by recombinant DNA technology and the glycoprotein can be administered to patients diagnosed with MPS II systemically and/or into the CSF for ERT). Human cell lines that can be used for such recombinant glycoprotein production include but are not limited to HT-22, SK-N-MC, HCN-1A, HCN-2, NT2, SH-SY5y, hNSC11, or ReNcell VM (see, e.g., Dumont et al., 2016, Critical Rev in Biotech 36(6):1110-1122 "Human cell lines for biopharmaceutical manufacturing: history, status, and future perspectives" which is incorporated by reference in its entirety for a review of the human cell lines that could be used for the recombinant production of the rHuGlyIDS glycoprotein). To ensure complete glycosylation, especially sialylation, and tyrosine-sulfation, the cell line used for production can be enhanced by engineering the host cells to co-express α-2,6-sialyltransferase (or both α-2,3- and α-2,6-sialyltransferases) and/or TPST-1 and TPST-2 enzymes responsible for tyrosine-O-sulfation.

While the delivery of rhIDS should minimize immune reactions, the clearest potential source of toxicity related to CNS-directed gene therapy is generating immunity against the expressed rhIDS protein in human subjects who are genetically deficient for IDS and, therefore, potentially not tolerant of the protein and/or the vector used to deliver the transgene.

Thus, in a preferred embodiment, it is advisable to co-treat the patient with immune suppression therapy—especially when treating patients with severe disease who have close to zero levels of IDS. Immune suppression therapies involving a regimen of tacrolimus or rapamycin (sirolimus) in combination with mycophenolic acid, or other immune suppression regimens used in tissue transplantation procedures can be employed. Such immune suppression treatment may be administered during the course of gene therapy, and in certain embodiments, pre-treatment with immune suppression therapy may be preferred. Immune suppression therapy can be continued subsequent to the gene therapy treatment, based on the judgment of the treating physician, and may thereafter be withdrawn when immune tolerance is induced; e.g., after 180 days.

Combinations of delivery of the rhIDS to the CSF accompanied by delivery of other available treatments are encompassed by the methods of the invention. The additional treatments may be administered before, concurrently or subsequent to the gene therapy treatment. Available treatments for MPS II that could be combined with the gene therapy of the invention include but are not limited to enzyme replacement therapy using Elaprase® administered systemically or to the CSF; and/or HSCT therapy.

In certain embodiments, described herein is a method for treating a human subject diagnosed with mucopolysaccharidosis type II (MPS II), comprising delivering to the cerebrospinal fluid (CSF) of said human subject a therapeutically effective amount of a recombinant human iduronate-2-sulfatase (IDS) precursor produced by human neuronal or human glial cells.

In certain embodiments, described herein is a method of treating a human subject diagnosed with mucopolysaccharidosis type II (MPS II), comprising delivering to the cerebrospinal fluid (CSF) of said human subject, a therapeutically effective amount of a recombinant human iduronate-2-sulfatase (IDS) glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated, does not contain detectable NeuGc, and is mannose-6-phosphorylated.

In certain embodiments, described herein is a method of treating a human subject diagnosed with mucopolysaccharidosis type II (MPS II), comprising delivering to the cerebrospinal fluid (CSF) of said human subject, a therapeutically effective amount of a recombinant human iduronate-2-sulfatase (IDS) glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated, does not contain detectable NeuGc and/or α-Gal antigen, and is mannose-6-phosphorylated.

In certain embodiments, the human IDS precursor is delivered to the CSF from a depot of cells in the central nervous system genetically engineered to secrete said IDS precursor into the CSF. In certain embodiments, the depot is formed in the subject's brain. In certain embodiments, the human subject is deficient in IDS activity. In certain embodiments, the human IDS comprises the amino acid sequence of SEQ ID NO. 1.

In certain embodiments, described herein is a method of treating a human subject diagnosed with mucopolysaccharidosis type II (MPS II), comprising administering to the cerebrospinal fluid (CSF) of said human subject a recombinant nucleotide expression vector encoding human iduronate-2-sulfatase (IDS), wherein said expression vector when used to transduce a primary human neuronal cell in culture directs the expression of a secreted human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated and mannose-6-phosphorylated.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed in the subject's central nervous system that secretes a recombinant human IDS glycoprotein precursor that is α2,6-sialylated and mannose-6-phosphorylated.

In certain embodiments, secretion of said recombinant human IDS glycoprotein precursor that is α2,6-sialylated is confirmed by transducing a human neuronal cell line with said recombinant nucleotide expression vector in cell culture. In certain embodiments, secretion of said recombinant human IDS glycoprotein precursor that is mannose-6-phosphorylated is confirmed by transducing a human neuronal cell line with said recombinant nucleotide expression vector in cell culture. In certain embodiments, the secretion is confirmed in the presence and absence of mannose-6-phosphate.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed that secretes a glycosylated IDS precursor containing a α2,6-sialylated glycan; wherein said recombinant vector, when used to transduce human neuronal cells in culture results in secretion of said glycosylated IDS precursor containing a α2,6-sialylated glycan in said cell culture.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed that secretes a glycosylated IDS precursor that contains a mannose-6-phosphate; wherein said recombinant vector, when used to transduce human neuronal cells in culture results in secretion of said glycosylated IDS precursor that is mannose-6-phosphorylated in said cell culture.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed that secretes a glycosylated IDS precursor that contains a formylglycine; wherein said recombinant vector, when used to transduce human neuronal cells in culture results in secretion of said glycosylated IDS precursor that contains a formylglycine in said cell culture.

In certain embodiments, the human IDS comprises the amino acid sequence of SEQ ID NO. 1. In certain embodiments, the IDS transgene encodes a leader peptide. In certain embodiments, the expression vector is a replication defective AAV vector. In certain embodiments, the expression vector is delivered to the CSF of the subject by intrathecal (e.g., intracisternal, C1-2 puncture if feasible for the patient, or lumbar puncture), intracerebroventricular, or intranasal administration. In certain embodiments, the human subject is deficient in IDS activity.

In preferred embodiments, the glycosylated IDS does not contain detectable NeuGc and/or α-Gal. The phrase "detectable NeuGc and/or α-Gal" used herein means NeuGc and/or α-Gal moieties detectable by standard assay methods known in the art. For example, NeuGc may be detected by HPLC according to Hara et al., 1989, "Highly Sensitive Determination of N-Acetyl- and N-Glycolylneuraminic Acids in Human Serum and Urine and Rat Serum by Reversed-Phase Liquid Chromatography with Fluorescence Detection." J. Chromatogr., B: Biomed. 377: 111-119, which is hereby incorporated by reference for the method of detecting NeuGc. Alternatively, NeuGc may be detected by mass spectrometry. The α-Gal may be detected using an ELISA, see, for example, Galili et al., 1998, "A sensitive assay for measuring alpha-Gal epitope expression on cells by a monoclonal anti-Gal antibody." Transplantation. 65(8):1129-32, or by mass spectrometry, see, for example, Ayoub et al., 2013, "Correct primary structure assessment and extensive glyco-profiling of cetuximab by a combination of intact, middle-up, middle-down and bottom-up ESI and MALDI mass spectrometry techniques." Landes Bioscience. 5(5): 699-710. See also the references cited in Platts-Mills et al., 2015, "Anaphylaxis to the Carbohydrate Side-Chain Alpha-gal" Immunol Allergy Clin North Am. 35(2): 247-260.

5.1 Processing, N-Glycosylation and Tyrosine Sulfation 5.1.1. Processing

Human IDS includes a 25 amino acid signal sequence which is cleaved during processing. An initial 76 kDa intracellular IDS precursor is converted into a phosphorylated 90 kDa IDS precursor after modification of its oligosaccharide chains in the Golgi apparatus. This precursor is processed by glycosylation modifications and proteolytic cleavage through various intracellular intermediates to a major 55 kDa form. To summarize, after removal of the 25 aa signal sequence, proteolytic processing involves N-terminal proteolytic cleavage downstream of $N^3$ removing a propeptide of eight amino acids (residues 26-33), and C-terminal proteolytic cleavage upstream of $N^{513}$ which releases an 18 kDa polypeptide and produces a 62 kDa intermediate that is converted to a 55 kDa mature form. Further proteolytic cleavage yields a 45 kDa mature form located in the lysosomal compartment. (See FIG. 4 for diagram reproduced from Millat et al., 1997, Exp Cell Res 230: 362-367 ("Millat 1997"); Millat et al. 1997, Biochem J. 326: 243-247 ("Millat 1997a"); and Froissart et al., 1995, Biochem J. 309:425-430, each of which is incorporated by reference herein in its entirety).

A formylglycine modification of $C^{84}$ (shown in bold in FIG. 1) required for enzyme activity probably occurs as an early post-translational or co-translational event, most probably in the endoplasmic reticulum. (See, Millat 1997a, citing Schmidt et al., 1995, Cell 82: 271-278). Post-translational processing continues in the Golgi to include addition of complex sialic acid-containing glycans and acquisition of mannose-6-phosphate residues which tag the enzyme for delivery to the lysosomal compartment. (See, Clarke, 2008, Expert Opin Pharmacother 9: 311-317 for a concise review which is incorporated by reference herein in its entirety).

In a specific embodiment, HuGlyIDS used in accordance with the methods described herein, when expressed in a neuronal or glial cell, in vivo or in vitro, can be the 90 kDa (e.g., 85 kDa, 86 kDa, 87 kDa, 88 kDa, 89 kDa, 90 kDa, 91 kDa, 92 kDa, 93 kDa, 94 kDa, or 95 kDa) mannose-6-phosphorylated form of the enzyme. IDS produced from neuronal and glial cells may contain higher M6P content, as reported in Daniele 2002, and in Sleat, Proteomics, 2005 (indicating that the human brain contains more (in both a quantitative and qualitative sense) M6P glycoproteins than other tissues). It is possible to measure the M6P content of an IDS precursor, as done in Daniele 2002.

Accordingly, in certain embodiments, HuGlyIDS used in accordance with the methods described herein, when expressed in a neuronal or glial cell, in vivo or in vitro, is mannose-6-phosphorylated at a higher level than IDS expressed in a non-neuronal or glial cell. In particular, HuGlyIDS used in accordance with the methods described herein, when expressed in a neuronal or glial cell, in vivo or in vitro, is mannose-6-phosphorylated at a higher level than IDS expressed in a HT1080 or CHO cell. In certain embodiments, the mannose-6-phosphorylation level of the expressed IDS is measured by uptake of the IDS by a human neuronal cell in the presence of M6P (e.g., 5 mM M6P). In certain embodiments, when expressed in a neuronal or glial cell, in vivo or in vitro, 10%-20%, 20%-30%, 30%-40%, 40%-50%, 50%-60%, 60%-70%, 70%-80%, 80%-90%, or 90%-100% of HuGlyIDS molecules used in accordance with the methods described herein are mannose-6-phosphorylated.

5.1.2. N-Glycosylation

Neuronal and glial cells in the CNS are secretory cells that possess the cellular machinery for post-translational processing of secreted proteins—including glycosylation and tyrosine-O-sulfation. hIDS has eight asparaginal ("N") glycosylation sites identified in FIG. 1 ($N^{31}ST$; $N^{115}FS$; $N^{144}HT$; $N^{246}IT$; $N^{280}IS$; $N^{325}ST$; $N^{513}FS$; $N^{537}DS$). Two of the eight N-linked glycosylation sites, namely $N^{280}$ and $N^{116}$, are mannose-6-phophorylated in IDS obtained from human brain. (Sleat et al., 2006, Mol & Cell Proeomics 5.4: 686-701, reported at Table V). While no single glycosylation site is essential for IDS stability, glycosylation at position $N^{280}$ is important for cellular internalization and lysosomal targeting via the mannose-6-phosphate (M6P) receptor. (Chung et al., 2014, Glycoconj J 31:309-315 at p. 310, first column). In the normal physiologic state, IDS is produced at very low levels and very little, if any, enzyme is secreted from the cell. (Clarke, 2008, supra).

It is not essential that every molecule produced either in the gene therapy or protein therapy approach be fully glycosylated and sulfated. Rather, the population of glycoproteins produced should have sufficient glycosylation and sulfation to demonstrate efficacy.

In a specific embodiment, HuGlyIDS used in accordance with the methods described herein, when expressed in a neuronal or glial cell, in vivo or in vitro, could be glycosylated at 100% of its N-glycosylation sites. However, one of skill in the art will appreciate that not every N-glycosylation site of HuGlyIDS need be N-glycosylated in order for benefits of glycosylation to be attained. Rather, benefits of glycosylation can be realized when only a percentage of N-glycosylation sites are glycosylated, and/or when only a percentage of expressed IDS molecules are glycosylated. Accordingly, in certain embodiments, HuGlyIDS used in accordance with the methods described herein, when expressed in a neuronal or glial cell, in vivo or in vitro, is glycosylated at 10%-20%, 20%-30%, 30%-40%, 40%-50%, 50%-60%, 60%-70%, 70%-80%, 80%-90%, or 90%-100% of its available N-glycosylation sites. In certain embodiments, when expressed in a neuronal or glial cell, in vivo or in vitro, 10%-20%, 20%-30%, 30%-40%, 40%-50%, 50%-60%, 60%-70%, 70%-80%, 80%-90%, or 90%-100% of HuGlyIDS molecules used in accordance with the methods described herein are glycosylated at least one of their available N-glycosylation sites.

In a specific embodiment, at least 10%, 20% 30%, 40%, 50%, 60%, 70%, 75%, 80%, 85%, 90%, 95%, or 99% of the N-glycosylation sites present in HuGlyIDS used in accordance with the methods described herein are glycosylated at an Asn residue (or other relevant residue) present in an N-glycosylation site, when the HuGlyIDS is expressed in a neuronal or glial cell, in vivo or in vitro. That is, at least 50%, 60%, 70%, 75%, 80%, 85%, 90%, 95%, or 99% of the N-glycosylation sites of the resultant HuGlyIDS are glycosylated.

In another specific embodiment, at least 10%, 20% 30%, 40%, 50%, 60%, 70%, 75%, 80%, 85%, 90%, 95%, or 99% of the N-glycosylation sites present in a HuGlyIDS molecule used in accordance with the methods described herein are glycosylated with an identical attached glycan linked to the Asn residue (or other relevant residue) present in an N-glycosylation site, when the HuGlyIDS is expressed in a neuronal or glial cell, in vivo or in vitro. That is, at least 50%, 60%, 70%, 75%, 80%, 85%, 90%, 95%, or 99% of the N-glycosylation sites of the resultant HuGlyIDS have an identical attached glycan.

Importantly, when the IDS proteins used in accordance with the methods described herein are expressed in neuronal or glial cells, the need for in vitro production in prokaryotic host cells (e.g., E. coli) or eukaryotic host cells (e.g., CHO cells) is circumvented. Instead, as a result of the methods described herein (e.g., use of neuronal or glial cells to express IDS), N-glycosylation sites of the IDS proteins are advantageously decorated with glycans relevant to and beneficial to treatment of humans, and, in particular, at the target location of treatment. Such an advantage is unattainable when CHO cells or E. coli are utilized in protein production, because e.g., CHO cells (1) do not express 2,6 sialyltransferase and thus cannot add 2,6 sialic acid during N-glycosylation and (2) can add Neu5Gc as sialic acid instead of Neu5Ac; and because E. coli does not naturally contain components needed for N-glycosylation. Furthermore, such an advantage may be unattainable when human cells that are not neuronal or glial cells are utilized in protein production. Accordingly, in one embodiment, an IDS protein expressed in a neuronal or glial cell to give rise to a HuGlyIDS used in the methods of treatment described herein is glycosylated in the manner in which a protein is N-glycosylated in human neuronal or glial cells, but is not glycosylated in the manner in which proteins are glycosylated in CHO cells. In another embodiment, an IDS protein expressed in a neuronal or glial cell to give rise to a HuGlyIDS used in the methods of treatment described herein is glycosylated in the manner in which a protein is N-glycosylated in a neuronal or glial cells, wherein such glycosylation is not naturally possible using a prokaryotic host cell, e.g., using E. coli. In one embodiment, an IDS protein expressed in a human neuronal or glial cell to give rise to a HuGlyIDS used in the methods of treatment described herein is glycosylated in the manner in which a protein is N-glycosylated in human neuronal or glial cells, but is not glycosylated in the manner in which proteins are glycosylated in human cells which are not neuronal or glial cells.

Assays for determining the glycosylation pattern of proteins are known in the art. For example, hydrazinolysis can be used to analyze glycans. First, polysaccharides are released from their associated protein by incubation with hydrazine (the Ludger Liberate Hydrazinolysis Glycan Release Kit, Oxfordshire, UK can be used). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans can be purified on carbon columns and subsequently labeled at the reducing end with the fluorophor 2-amino benzamide. The labeled polysaccharides can be separated on a GlycoSep-N column (GL Sciences) according to the HPLC protocol of Royle et al, Anal Biochem 2002, 304(1):70-90. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit can be confirmed and additionally in homogeneity of the polysaccharide composition can be identified. Specific peaks of low molecular weight can be analyzed by MALDI-MS/MS and the result used to confirm the glycan sequence. Each peak corresponds to a polymer consisting of a certain number of repeat units and fragments thereof. The chromatogram thus allows measurement of the polymer length distribution. The elution time is an indication for polymer length, while fluorescence intensity correlates with molar abundance for the respective polymer.

Homogeneity of the glycan patterns associated with proteins, as it relates to both glycan length and numbers glycans present across glycosylation sites, can be assessed using methods known in the art, e.g., methods that measure glycan length and hydrodynamic radius. Size exclusion-HPLC allows the measurement of the hydrodynamic radius. Higher numbers of glycosylation sites in a protein lead to higher variation in hydrodynamic radius compared to a carrier with less glycosylation sites. However, when single glycan chains are analyzed, they may be more homogenous due to the more controlled length. Glycan length can measured by hydrazinolysis, SDS PAGE, and capillary gel electrophoresis. In addition, homogeneity can also mean that certain glycosylation site usage patterns change to a broader/narrower range. These factors can be measured by Glycopeptide LC-MS/MS.

N-glycosylation confers numerous benefits on the HuGlyIDS used in the methods described herein. Such benefits are unattainable by production of proteins in *E. coli*, because *E. coli* does not naturally possess components needed for N-glycosylation. Further, some benefits are unattainable through protein production in, e.g., CHO cells, because CHO cells lack components needed for addition of certain glycans (e.g., 2,6 sialic acid) and because CHO cells can add glycans, e.g., Neu5Gc not typical to humans, and the α-Gal antigen which is immunogenic in most individuals and at high concentrations can trigger anaphylaxis. Even further, some benefits are unattainable through protein production in human cells that are not neuronal or glial cells. Thus, the expression of IDS in human neuronal or glial cells results in the production of HuGlyIDS comprising beneficial glycans that otherwise would not be associated with the protein if produced in CHO cells, in *E. coli*, or in human cells which are not neuronal or glial cells.

5.1.3. Tyrosine Sulfation

In addition to the N-linked glycosylation sites, hIDS contains a tyrosine ("Y") sulfation site (PSSEKY$^{165}$ENTKTCRGPD). (See, e.g., Yang et al., 2015, Molecules 20:2138-2164, esp. at p. 2154 which is incorporated by reference in its entirety for the analysis of amino acids surrounding tyrosine residues subjected to protein tyrosine sulfation. The "rules" can be summarized as follows: Y residues with E or D within +5 to −5 position of Y, and where position −1 of Y is a neutral or acidic charged amino acid—but not a basic amino acid, e.g., R, K, or H that abolishes sulfation).

Importantly, tyrosine-sulfated proteins cannot be produced in *E. coli*, which naturally does not possess the enzymes required for tyrosine-sulfation. Further, CHO cells are deficient for tyrosine sulfation—they are not secretory cells and have a limited capacity for post-translational tyrosine-sulfation. See, e.g., Mikkelsen & Ezban, 1991, Biochemistry 30: 1533-1537. Advantageously, the methods provided herein call for expression of IDS, e.g., HuGlyIDS, in neurons or glial cells, which are secretory and do have capacity for tyrosine sulfation. Assays for detection tyrosine sulfation are known in the art. See, e.g., Yang et al., 2015, Molecules 20:2138-2164.

Tyrosine-sulfation of hIDS—a robust post-translational process in human CNS cells—should result in improved processing and activity of transgene products. The significance of tyrosine-sulfation of lysosomal proteins has not been elucidated; but in other proteins it has been shown to increase avidity of protein-protein interactions (antibodies and receptors), and to promote proteolytic processing (peptide hormone). (See, Moore, 2003, J Biol. Chem. 278: 24243-46; and Bundegaard et al., 1995, The EMBO J 14: 3073-79). The tyrosylprotein sulfotransferase (TPST1) responsible for tyrosine-sulfation (which may occur as a final step in IDS processing) is apparently expressed at higher levels (based on mRNA) in the brain (gene expression data for TPST1 may be found, for example, at the EMBL-EBI Expression Atlas, accessible at http://www.ebi-.ac.uk/gxa/home).

5.2 Constructs and Formulations

For use in the methods provided herein are viral vectors or other DNA expression constructs encoding iduronate-2-sulfatase (IDS), e.g., human IDS (hIDS). The viral vectors and other DNA expression constructs provided herein include any suitable method for delivery of a transgene to the cerebrospinal fluid (CSF). The means of delivery of a transgene include viral vectors, liposomes, other lipid-containing complexes, other macromolecular complexes, synthetic modified mRNA, unmodified mRNA, small molecules, non-biologically active molecules (e.g., gold particles), polymerized molecules (e.g., dendrimers), naked DNA, plasmids, phages, transposons, cosmids, or episomes. In some embodiments, the vector is a targeted vector, e.g., a vector targeted to neuronal cells.

In some aspects, the disclosure provides for a nucleic acid for use, wherein the nucleic acid encodes an IDS, e.g., hIDS, operatively linked to a promoter selected from the group consisting of: cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter and opsin promoter.

In certain embodiments, provided herein are recombinant vectors that comprise one or more nucleic acids (e.g. polynucleotides). The nucleic acids may comprise DNA, RNA, or a combination of DNA and RNA. In certain embodiments, the DNA comprises one or more of the sequences selected from the group consisting of promoter sequences, the sequence of the gene of interest (the transgene, e.g., IDS), untranslated regions, and termination sequences. In certain embodiments, viral vectors provided herein comprise a promoter operably linked to the gene of interest.

In certain embodiments, nucleic acids (e.g., polynucleotides) and nucleic acid sequences disclosed herein may be codon-optimized, for example, via any codon-optimization technique known to one of skill in the art (see, e.g., review by Quax et al., 2015, Mol Cell 59:149-161).

In another aspect, the disclosure provides for a formulation comprising a recombinant nucleotide expression vector encoding human IDS, wherein the formulation is suitable for administration to the cerebrospinal fluid of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain α-Gal antigen, and/or is mannose-6-phosphorylated. For example, the formulation may contain buffer (such as, a buffer having a particular pH, or a buffer containing a particular ingredient) that makes it suitable for administration to the cerebrospinal fluid of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain α-Gal antigen, and/or is mannose-6-phosphorylated. In a specific embodiment, the buffer comprises a physiologically compatible aqueous buffer, a surfactant and optional excipients.

In another aspect, the disclosure provides for a kit comprising a recombinant nucleotide expression vector encoding human IDS and a pharmaceutically acceptable carrier, wherein the recombinant nucleotide expression vector is suitable for administration to the cerebrospinal fluid (CSF) of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated. In another aspect, the disclosure provides for a kit comprising a formulation comprising a recombinant nucleotide expression vector encoding human IDS, wherein the formulation is suitable for administration to the CSF of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated. A kit described herein comprises the recombinant nucleotide expression vector or the formulation in one or more containers. Optionally associated with such one or more containers can be a notice in the form prescribed by a governmental agency regulating the manufacture, use or sale of pharmaceuticals or biological products, which notice reflects approval by the agency of manufacture, use or sale for human administration.

The formulations and kits encompassed herein can be used in accordance with the methods for treating a human patient as provided in this disclosure.

5.2.1. mRNA

In certain embodiments, the vectors provided herein are modified mRNA encoding for the gene of interest (e.g., the transgene, for example, IDS). The synthesis of modified and unmodified mRNA for delivery of a transgene to the CSF is taught, for example, in Hocquemiller et al., 2016, Human Gene Therapy 27(7):478-496, which is incorporated by reference herein in its entirety. In certain embodiments, provided herein is a modified mRNA encoding for IDS, e.g., hIDS.

5.2.2. Viral Vectors

Viral vectors include adenovirus, adeno-associated virus (AAV, e.g., AAV9, AAVrh10), lentivirus, helper-dependent adenovirus, herpes simplex virus, poxvirus, hemagglutinin virus of Japan (HVJ), alphavirus, vaccinia virus, and retrovirus vectors. Retroviral vectors include murine leukemia virus (MLV)- and human immunodeficiency virus (HIV)-based vectors. Alphavirus vectors include semliki forest virus (SFV) and sindbis virus (SIN). In certain embodiments, the viral vectors provided herein are recombinant viral vectors. In certain embodiments, the viral vectors provided herein are altered such that they are replication-deficient in humans. In certain embodiments, the viral vectors are hybrid vectors, e.g., an AAV vector placed into a "helpless" adenoviral vector. In certain embodiments, provided herein are viral vectors comprising a viral capsid from a first virus and viral envelope proteins from a second virus. In specific embodiments, the second virus is vesicular stomatitus virus (VSV). In more specific embodiments, the envelope protein is VSV-G protein.

In certain embodiments, the viral vectors provided herein are HIV based viral vectors. In certain embodiments, HIV-based vectors provided herein comprise at least two polynucleotides, wherein the gag and pol genes are from an HIV genome and the env gene is from another virus.

In certain embodiments, the viral vectors provided herein are herpes simplex virus-based viral vectors. In certain embodiments, herpes simplex virus-based vectors provided herein are modified such that they do not comprise one or more immediately early (IE) genes, rendering them non-cytotoxic.

In certain embodiments, the viral vectors provided herein are MLV based viral vectors. In certain embodiments, MLV-based vectors provided herein comprise up to 8 kb of heterologous DNA in place of the viral genes.

In certain embodiments, the viral vectors provided herein are lentivirus-based viral vectors. In certain embodiments, lentiviral vectors provided herein are derived from human lentiviruses. In certain embodiments, lentiviral vectors provided herein are derived from non-human lentiviruses. In certain embodiments, lentiviral vectors provided herein are packaged into a lentiviral capsid. In certain embodiments, lentiviral vectors provided herein comprise one or more of the following elements: long terminal repeats, a primer binding site, a polypurine tract, att sites, and an encapsidation site.

In certain embodiments, the viral vectors provided herein are alphavirus-based viral vectors. In certain embodiments, alphavirus vectors provided herein are recombinant, replication-defective alphaviruses. In certain embodiments, alphavirus replicons in the alphavirus vectors provided herein are targeted to specific cell types by displaying a functional heterologous ligand on their virion surface.

In certain embodiments, the viral vectors provided herein are AAV based viral vectors. In preferred embodiments, the viral vectors provided herein are AAV9 or AAVrh10 based viral vectors. In certain embodiments, the AAV9 or AAVrh10 based viral vectors provided herein retain tropism for CNS cells. Multiple AAV serotypes have been identified. In certain embodiments, AAV-based vectors provided herein comprise components from one or more serotypes of AAV. In certain embodiments, AAV based vectors provided herein comprise components from one or more of AAV1, AAV2, AAV3, AAV4, AAV5, AAV6, AAV7, AAV8, AAV9, AAVrh10, AAV10 or AAV11. In preferred embodiments, AAV based vectors provided herein comprise components from one or more of AAV8, AAV9, AAVrh10, AAV10, or AAV11 serotypes. AAV9-based viral vectors are used in the methods described herein. Nucleic acid sequences of AAV based viral vectors and methods of making recombinant AAV and AAV capsids are taught, for example, in U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety. In one aspect, provided herein are AAV (e.g., AAV9 or AAVrh10)-based viral vectors encoding a transgene (e.g., IDS). In specific embodiments, provided herein are AAV9-based viral vectors encoding IDS. In more specific embodiments, provided herein are AAV9-based viral vectors encoding hIDS.

Provided in particular embodiments are AAV9 vectors comprising an artificial genome comprising (i) an expression cassette containing the transgene under the control of regulatory elements and flanked by ITRs; and (ii) a viral capsid that has the amino acid sequence of the AAV9 capsid protein or is at least 95%, 96%, 97%, 98%, 99% or 99.9% identical to the amino acid sequence of the AAV9 capsid protein (SEQ ID NO: 26) while retaining the biological function of the AAV9 capsid. In certain embodiments, the encoded AAV9 capsid has the sequence of SEQ ID NO: 26 with 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions and retaining the biological function of the AAV9 capsid. FIG. 6 provides a comparative alignment of the amino acid sequences of the capsid proteins of different AAV serotypes with potential amino acids that may be substituted at certain positions in the aligned sequences based upon the comparison in the row labeled SUBS. Accordingly, in specific embodiments, the AAV9 vector comprises an AAV9 capsid variant that has 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions identified in the SUBS row of FIG. 6 that are not present at that position in the native AAV9 sequence.

In certain embodiments, the AAV that is used in the methods described herein is Anc80 or Anc80L65, as described in Zinn et al., 2015, Cell Rep. 12(6): 1056-1068, which is incorporated by reference in its entirety. In certain embodiments, the AAV that is used in the methods described herein comprises one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In certain embodiments, the AAV that is used in the methods described herein is AAV.7m8, as described in U.S. Pat. Nos. 9,193,956; 9,458,517; and 9,587,282 and US patent application publication no. 2016/0376323, each of which is incorporated herein by reference in its entirety. In certain embodiments, the AAV that is used in the methods described herein is any AAV disclosed in U.S. Pat. No. 9,585,971, such as AAV-PHP.B. In certain embodiments, the AAV that is used in the methods described herein is an AAV disclosed in any of the following patents and patent applications, each of which is incorporated herein by reference in its entirety: U.S. Pat. Nos. 7,906,111; 8,524,446; 8,999,678; 8,628,966; 8,927,514; 8,734,809; 9,284,357; 9,409,953; 9,169,299; 9,193,956; 9,458,517; and 9,587,282 US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In certain embodiments, a single-stranded AAV (ssAAV) may be used supra. In certain embodiments, a self-complementary vector, e.g., scAAV, may be used (see, e.g., Wu, 2007, Human Gene Therapy, 18(2):171-82, McCarty et al, 2001, Gene Therapy, Vol 8, Number 16, Pages 1248-1254; and U.S. Pat. Nos. 6,596,535; 7,125,717; and 7,456,683, each of which is incorporated herein by reference in its entirety).

In certain embodiments, the viral vectors used in the methods described herein are adenovirus based viral vectors. A recombinant adenovirus vector may be used to transfer in the IDS. The recombinant adenovirus can be a first generation vector, with an E1 deletion, with or without an E3 deletion, and with the expression cassette inserted into either deleted region. The recombinant adenovirus can be a second generation vector, which contains full or partial deletions of the E2 and E4 regions. A helper-dependent adenovirus retains only the adenovirus inverted terminal repeats and the packaging signal (phi). The transgene is inserted between the packaging signal and the 3'ITR, with or without stuffer sequences to keep the artificial genome close to wild-type size of approx. 36 kb. An exemplary protocol for production of adenoviral vectors may be found in Alba et al., 2005, "Gutless adenovirus: last generation adenovirus for gene therapy," Gene Therapy 12:S18-S27, which is incorporated by reference herein in its entirety.

In certain embodiments, the viral vectors used in the methods described herein are lentivirus based viral vectors. A recombinant lentivirus vector may be used to transfer in the IDS. Four plasmids are used to make the construct: Gag/pol sequence containing plasmid, Rev sequence containing plasmids, Envelope protein containing plasmid (i.e. VSV-G), and Cis plasmid with the packaging elements and the IDS gene.

For lentiviral vector production, the four plasmids are co-transfected into cells (i.e., HEK293 based cells), whereby polyethylenimine or calcium phosphate can be used as transfection agents, among others. The lentivirus is then harvested in the supernatant (lentiviruses need to bud from the cells to be active, so no cell harvest needs/should be done). The supernatant is filtered (0.45 µm) and then magnesium chloride and benzonase added. Further downstream processes can vary widely, with using TFF and column chromatography being the most GMP compatible ones. Others use ultracentrifugation with/without column chromatography. Exemplary protocols for production of lentiviral vectors may be found in Lesch et al., 2011, "Production and purification of lentiviral vector generated in 293T suspension cells with baculoviral vectors," Gene Therapy 18:531-538, and Ausubel et al., 2012, "Production of CGMP-Grade Lentiviral Vectors," Bioprocess Int. 10(2):32-43, both of which are incorporated by reference herein in their entireties.

In a specific embodiment, a vector for use in the methods described herein is one that encodes an IDS (e.g., hIDS) such that, upon transduction of cells in the CNS, or a relevant cell (e.g., a neuronal cell in vivo or in vitro), a glycosylated variant of IDS is expressed by the transduced cell. In a specific embodiment, a vector for use in the methods described herein is one that encodes an IDS (e.g., hIDS) such that, upon transduction of a cell in the CNS, or a relevant cell (e.g., a neuronal cell in vivo or in vitro), a sulfated variant of IDS is expressed by the cell.

5.2.3. Promoters and Modifiers of Gene Expression

In certain embodiments, the vectors provided herein comprise components that modulate gene delivery or gene expression (e.g., "expression control elements"). In certain embodiments, the vectors provided herein comprise components that modulate gene expression. In certain embodiments, the vectors provided herein comprise components that influence binding or targeting to cells. In certain embodiments, the vectors provided herein comprise components that influence the localization of the polynucleotide (e.g., the transgene) within the cell after uptake. In certain embodiments, the vectors provided herein comprise components that can be used as detectable or selectable markers, e.g., to detect or select for cells that have taken up the polynucleotide.

In certain embodiments, the viral vectors provided herein comprise one or more promoters. In certain embodiments, the promoter is a constitutive promoter. In alternate embodiments, the promoter is an inducible promoter. The native IDS gene, like most housekeeping genes, primarily uses a GC-rich promoter. In a preferred embodiment, strong constitutive promoters that provide for sustained expression of hIDS are used. Such promoters include "CAG" synthetic promoters that contain: "C"—the cytomegalovirus (CMV) early enhancer element; "A"—the promoter as well as the first exon and intron of the chicken beta-actin gene; and "G"—the splice acceptor of the rabbit beta-globin gene (see, Miyazaki et al., 1989, Gene 79: 269-277; and Niwa et al., Gene 108: 193-199).

In certain embodiments, the promoter is a CB7 promoter (see Dinculescu et al., 2005, Hum Gene Ther 16: 649-663, incorporated by reference herein in its entirety). In some embodiments, the CB7 promoter includes other expression control elements that enhance expression of the transgene driven by the vector. In certain embodiments, the other expression control elements include chicken β-actin intron and/or rabbit β-globin polA signal. In certain embodiments, the promoter comprises a TATA box. In certain embodiments, the promoter comprises one or more elements. In certain embodiments, the one or more promoter elements may be inverted or moved relative to one another. In certain embodiments, the elements of the promoter are positioned to function cooperatively. In certain embodiments, the elements of the promoter are positioned to function independently. In certain embodiments, the viral vectors provided herein comprise one or more promoters selected from the group consisting of the human CMV immediate early gene promoter, the SV40 early promoter, the Rous sarcoma virus (RS) long terminal repeat, and rat insulin promoter. In certain embodiments, the vectors provided herein comprise one or more long terminal repeat (LTR) promoters selected from the group consisting of AAV, MLV, MMTV, SV40, RSV, HIV-1, and HIV-2 LTRs. In certain embodiments, the vectors provided herein comprise one or more tissue specific promoters (e.g., a neuronal cell-specific promoter).

In certain embodiments, the viral vectors provided herein comprise one or more regulatory elements other than a promoter. In certain embodiments, the viral vectors provided herein comprise an enhancer. In certain embodiments, the viral vectors provided herein comprise a repressor. In certain embodiments, the viral vectors provided herein comprise an intron or a chimeric intron. In certain embodiments, the viral vectors provided herein comprise a polyadenylation sequence.

5.2.4. Signal Peptides

In certain embodiments, the vectors provided herein comprise components that modulate protein delivery. In certain embodiments, the viral vectors provided herein comprise one or more signal peptides. In certain embodiments, the signal peptides allow for the transgene product (e.g., IDS) to achieve the proper packaging (e.g. glycosylation) in the cell. In certain embodiments, the signal peptides allow for the transgene product (e.g., IDS) to achieve the proper localization in the cell. In certain embodiments, the signal peptides allow for the transgene product (e.g., IDS) to achieve secretion from the cell. Examples of signal peptides to be used in connection with the vectors and transgenes provided herein may be found in Table 1. Signal peptides may also be referred to herein as leader sequences or leader peptides.

TABLE 2

Signal peptides for use with the vectors provided herein.

| SEQ ID NO. | Signal Peptide | Sequence |
|---|---|---|
| 2 | Oligodendrocyte-myelin glycoprotein (hOMG) signal peptide | MEYQILKMSLCLFILLFLTP GILC |
| 3 | Cellular repressor of E1A-stimulated genes 2 (hCREG2) signal peptide | MSVRRGRRPARPGTRLSWLL CCSALLSPAAG |
| 4 | V-set and transmembrane domain containing 2B (hVSTM2B) signal peptide | MEQRNRLGALGYLPPLLLHA LLLFVADA |
| 5 | Protocadherin alpha-1 (hPCADHA1) signal peptide | MVFSRRGGLGARDLLLWLLL LAAWEVGSG |
| 6 | FAM19A1 (TAFA1) signal peptide | MAMVSAMSWVLYLWISACA |
| 7 | VEGF-A signal peptide | MNFLLSWVHW SLALLLYL HH AKWSQA |
| 8 | Fibulin-1 signal peptide | MERAAPSRRVPLPLLLLGGL ALLAAGVDA |
| 9 | Vitronectin signal peptide | MAPLRPLLILALLAWVALA |
| 10 | Complement Factor H signal peptide | MRLLAKIICLMLWAICVA |
| 11 | Opticin signal peptide | MRLLAFLSLLALVLQETGT |
| 12 | Albumin signal peptide | MKWVTFISLLFLFSSAYS |
| 13 | Chymotrypsinogen signal peptide | MAFLWLLSCWALLGTTFG |
| 14 | Interleukin-2 signal peptide | MYRMQLLSCIALILALVTNS |
| 15 | Trypsinogen-2 signal peptide | MNLLLILTFVAAAVA |

5.2.5. Untranslated Regions

In certain embodiments, the viral vectors provided herein comprise one or more untranslated regions (UTRs), e.g., 3' and/or 5' UTRs. In certain embodiments, the UTRs are optimized for the desired level of protein expression. In certain embodiments, the UTRs are optimized for the mRNA half life of the transgene. In certain embodiments, the UTRs are optimized for the stability of the mRNA of the transgene. In certain embodiments, the UTRs are optimized for the secondary structure of the mRNA of the transgene.

5.2.6. Inverted Terminal Repeats

In certain embodiments, the viral vectors provided herein comprise one or more inverted terminal repeat (ITR) sequences. ITR sequences may be used for packaging the recombinant gene expression cassette into the virion of the viral vector. In certain embodiments, the ITR is from an AAV, e.g., AAV9 (see, e.g., Yan et al., 2005, J. Virol., 79(1):364-379; U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety).

5.2.7. Transgenes

In certain embodiments, the vectors provided herein encode an IDS transgene. In specific embodiments, the IDS is controlled by appropriate expression control elements for expression in neuronal cells: In certain embodiments, the IDS (e.g., hIDS) transgene comprises the amino acid sequence of SEQ ID NO: 1. In certain embodiments, the IDS (e.g., hIDS) transgene comprises an amino acid sequence that is at least 85%, 86%, 87%, 88%, 89%, 90%, 91%, 92%, 93%, 94%, 95%, 96%, 97%, 98% or 99% identical to the sequence set forth in SEQ ID NO: 1.

The HuGlyIDS encoded by the transgene can include, but is not limited to human IDS (hIDS) having the amino acid sequence of SEQ ID NO. 1 (as shown in FIG. 1), and derivatives of hIDS having amino acid substitutions, deletions, or additions, e.g., including but not limited to amino acid substitutions selected from corresponding non-conserved residues in orthologs of IDS shown in FIG. 2, with the proviso with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inhert Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety.

For example, amino acid substitutions at a particular position of hIDS can be selected from among corresponding non-conserved amino acid residues found at that position in the IDS orthologs aligned in FIG. 2, with the proviso that such substitutions do not include any of the deleterious mutations shown in FIG. 3 or as reported by Sukegawa-Hayasaka et al., 2006, supra; Millat et al., 1998, supra; or Bonucelli et al., 2001, supra, each of which is incorporated by reference herein in its entirety. The resulting transgene product can be tested using conventional assays in vitro, in cell culture or test animals to ensure that the mutation does not disrupt IDS function. Preferred amino acid substitutions, deletions or additions selected should be those that maintain or increase enzyme activity, stability or half-life of IDS, as tested by conventional assays in vitro, in cell culture or animal models for MPS II. For example, the enzyme activity of the transgene product can be assessed using a conventional enzyme assay with, for example, 4-Methylumbelliferyl α-L-idopyranosiduronic acid 2-sulfate or 4-methylumbelliferyl sulfate as the substrate (see, e.g., Lee et al., 2015, Clin. Biochem. 48(18):1350-1353, Dean et al., 2006, Clin. Chem. 52(4):643-649 for exemplary IDS enzyme assays that can be used, each of which is incorporated by reference herein in its entirety). The ability of the transgene product to correct MPS II phenotype can be assessed in cell culture; e.g., by transducing MPS II cells in culture with a viral vector or other DNA expression construct encoding hIDS or a derivative; by adding the transgene product or a derivative to MPS II cells in culture; or by co-culturing MPS II cells with human neuronal/glial host cells engineered to express and secrete rhIDS or a derivative, and determining correction of the defect in the MPS II cultured cells, e.g., by detecting IDS enzyme activity and/or reduction in GAG storage in the MPS II cells in culture (see, e.g., Stroncek et al., 1999, Transfusion 39(4):343-350, which is incorporated by reference herein in its entirety).

5.2.8. Constructs

In certain embodiments, the viral vectors provided herein comprise the following elements in the following order: a) a first ITR sequence, b) a first linker sequence, c) a promoter sequence, d) a second linker sequence, e) an intron sequence, f) a third linker sequence, g) a sequence encoding the transgene (e.g., IDS), h) a fourth linker sequence, i) a poly A sequence, j) a fifth linker sequence, and k) a second ITR sequence.

In certain embodiments, the viral vectors provided herein comprise the following elements in the following order: a) a promoter sequence, and b) a sequence encoding the transgene (e.g., IDS). In certain embodiments, the viral vectors provided herein comprise the following elements in the following order: a) a promoter sequence, and b) a sequence encoding the transgene (e.g., IDS), wherein the transgene comprises a signal peptide.

In certain embodiments, the viral vectors provided herein comprise the following elements in the following order: a) a first ITR sequence, b) a first linker sequence, c) a promoter sequence, d) a second linker sequence, e) an intron sequence, f) a third linker sequence, g) a first UTR sequence, h) a sequence encoding the transgene (e.g., IDS), i) a second UTR sequence, j) a fourth linker sequence, k) a poly A sequence, l) a fifth linker sequence, and m) a second ITR sequence.

In certain embodiments, the viral vectors provided herein comprise the following elements in the following order: a) a first ITR sequence, b) a first linker sequence, c) a promoter sequence, d) a second linker sequence, e) an intron sequence, f) a third linker sequence, g) a first UTR sequence, h) a sequence encoding the transgene (e.g., IDS), i) a second UTR sequence, j) a fourth linker sequence, k) a poly A sequence, l) a fifth linker sequence, and m) a second ITR sequence, wherein the transgene comprises a signal peptide, and wherein the transgene encodes hIDS.

5.2.9. Manufacture and Testing of Vectors

The viral vectors provided herein may be manufactured using host cells. The viral vectors provided herein may be manufactured using mammalian host cells, for example, A549, WEHI, 10T1/2, BHK, MDCK, COS1, COST, BSC 1, BSC 40, BMT 10, VERO, W138, HeLa, 293, Saos, C2C12, L, HT1080, HepG2, primary fibroblast, hepatocyte, and myoblast cells. The viral vectors provided herein may be manufactured using host cells from human, monkey, mouse, rat, rabbit, or hamster.

The host cells are stably transformed with the sequences encoding the transgene and associated elements (i.e., the vector genome), and the means of producing viruses in the host cells, for example, the replication and capsid genes (e.g., the rep and cap genes of AAV). For a method of producing recombinant AAV vectors with AAV8 capsids, see Section IV of the Detailed Description of U.S. Pat. No. 7,282,199 B2, which is incorporated herein by reference in its entirety. Genome copy titers of said vectors may be determined, for example, by TAQMAN® analysis. Virions may be recovered, for example, by CsCl$_2$ sedimentation.

In vitro assays, e.g., cell culture assays, can be used to measure transgene expression from a vector described herein, thus indicating, e.g., potency of the vector. For example, the HT-22, SK-N-MC, HCN-1A, HCN-2, NT2, SH-SY5y, hNSC11, or ReNcell VM cell lines, or other cell lines that are derived from neuronal or glial cells or progenitors of neuronal or glial cells can be used to assess transgene expression. Once expressed, characteristics of the expressed product (i.e., HuGlyIDS) can be determined, including determination of the glycosylation and tyrosine sulfation patterns associated with the HuGlyIDS.

5.2.10. Compositions

Compositions are described comprising a vector encoding a transgene described herein and a suitable carrier. A suitable carrier (e.g., for administration to the CSF, and, for example, to neuronal cells) would be readily selected by one of skill in the art.

5.3 Gene Therapy

Methods are described for the administration of a therapeutically effective amount of a transgene construct to human subjects having MPS II. More particularly, methods for administration of a therapeutically effective amount of a transgene construct to patients having MPS II, in particular, for administration to the CSF are described. In particular embodiments, such methods for administration to the CSF of a therapeutically effective amount of a transgene construct can be used to treat to patients having Hunter's syndrome.

5.3.1. Target Patient Populations

In certain embodiments, therapeutically effective doses of the recombinant vector are administered to patients diagnosed with MPS II. In specific embodiments, the patients have been diagnosed with mild MPS II. In specific embodiments, the patients have been diagnosed with severe MPS II. In specific embodiments, the patients have been diagnosed with Hunter's syndrome.

In certain embodiments, therapeutically effective doses of the recombinant vector are administered to patients diagnosed with MPS II who have been identified as responsive to treatment with IDS, e.g., hIDS.

In certain embodiments, therapeutically effective doses of the recombinant vector are administered to pediatric patients. In certain embodiments, therapeutically effective doses of the recombinant vector are administered to patients that are less than three years old. In certain embodiments, therapeutically effective doses of the recombinant vector are administered to patients that are aged 2 to 4 years old. In certain embodiments, therapeutically effective doses of the recombinant vector are administered to patients that are 4 months old or older and less than 5 years old. In a specific embodiment, therapeutically effective doses of the recombinant vector are administered to patients that have severe MPS II and are 4 months old or older and less than 5 years old. In certain embodiments, therapeutically effective doses of the recombinant vector are administered to patients that are 18 months old or older and 8 years old or younger. In a specific embodiment, therapeutically effective doses of the recombinant vector are administered to patients that are pediatric male patients and are 18 months old or older and 8 years old or younger. In certain embodiments, therapeutically effective doses of the recombinant vector are administered to patients that are aged 3 to 8 years old. In certain embodiments, therapeutically effective doses of the recombinant vector are administered to patients that are aged 8 to 16 years old. In certain embodiments, therapeutically effective doses of the recombinant vector are administered to patients that are 10 years old or younger. In a specific embodiment, therapeutically effective doses of the recombinant vector are administered to patients that have severe MPS II and are 10 years old or younger. In certain embodiments, therapeutically effective doses of the recombinant vector are administered to patients that are more than 10 years old. In certain embodiments, therapeutically effective doses of the recombinant vector are administered to adolescent patients. In certain embodiments, therapeutically effective doses of the recombinant vector are administered to adult patients.

In certain embodiments, therapeutically effective doses of the recombinant vector are administered to patients diagnosed with MPS II who have been identified as responsive to treatment with IDS, e.g., hIDS, injected into the CSF prior to treatment with gene therapy.

5.3.2. Dosage and Mode of Administration

In certain embodiments, therapeutically effective doses of the recombinant vector are administered to the CSF via intrathecal administration (i.e., injection into the subarachnoid space so that the recombinant vectors distribute through the CSF and transduce cells in the CNS). This can be accomplished in a number of ways—e.g., by intracranial (cisternal or ventricular) injection, or injection into the lumbar cistern. In certain embodiments, intrathecal administration is performed via intracisternal (IC) injection (e.g., into the cisterna magna). In specific embodiments, intracisternal injection is performed by CT-guided suboccipital puncture. In specific embodiments, intrathecal injection is performed by lumbar puncture. In specific embodiments, injection into the subarachnoid space is performed by C1-2 puncture if feasible for the patient. In certain embodiments, therapeutically effective doses of the recombinant vector are administered to the CNS via intranasal administration. In certain embodiments, therapeutically effective doses of the recombinant vector are administered to the CNS via intraparenchymal injection. In certain embodiments, intraparenchymal injection is targeted to the striatum. In certain embodiments, intraparenchymal injection is targeted to the white matter. In certain embodiments, therapeutically effective doses of the recombinant vector are administered to the CSF by any means known to the art, for example, by any means disclosed in Hocquemiller et al., 2016, Human Gene Therapy 27(7):478-496, which is hereby incorporated by reference in its entirety.

For intrathecal administration, therapeutically effective doses of the recombinant vector should be administered to the CSF in an injection volume, preferably up to about 20 mL. A carrier suitable for intrathecal injection, such as Elliotts B Solution, should be used as a vehicle for the recombinant vectors. Elliots B Solution (generic name: sodium chloride, sodium bicarbonate, anhydrous dextrose, magnesium sulfate, potassium chloride, calcium chloride and sodium phosphate) is a sterile, nonpyrogenic, isotonic solution containing no bacteriostatic preservatives and is used as a diluent for intrathecal administration of chemotherapeutics.

In one embodiment, a non-replicating recombinant AAV9 vector expressing human iduronate-2-sulfatase (IDS) is used for treatment. In certain embodiments, the IDS expression cassette is flanked by inverted terminal repeats (ITRs) and expression is driven by a hybrid of the cytomegalovirus (CMV) enhancer and the chicken beta actin promoter (CB7). In certain embodiments, the transgene includes the chicken beta actin intron and a rabbit beta-globin polyadenylation (polyA) signal.

The rAAV9.hIDS is administered IC (by suboccipital injection) as a single flat dose ranging from $1.4 \times 10^{13}$ GC ($1.1 \times 10^{10}$ GC/g brain mass) to $7.0 \times 10^{13}$ GC ($5.6 \times 10^{10}$ GC/g brain mass) in a volume of about 5 to 20 ml. In the event the patient has neutralizing antibodies to AAV, doses at the high range may be used.

5.4 Combination Therapies

Combinations of administration of the HuGlyIDS to the CSF accompanied by administration of other available treatments are encompassed by the methods of the invention. The additional treatments may be administered before, concurrently or subsequent to the gene therapy treatment. Available treatments for MPS II that could be combined with the gene therapy of the invention include but are not limited to enzyme replacement therapy (ERT) using idursulfase administered systemically or to the CSF; and/or HSCT therapy. In another embodiment, ERT can be administered using the rHuGlyIDS glycoprotein produced in human neuronal and glial cell lines by recombinant DNA technology. Human neuronal and glial cell lines that can be used for such recombinant glycoprotein production include but are not limited to HT-22, SK-N-MC, HCN-1A, HCN-2, NT2, SH-SY5y, hNSC11, or ReNcell VM to name a few. To ensure complete glycosylation, especially sialylation, and tyrosine-sulfation, the cell line used for production can be enhanced by engineering the host cells to co-express α-2, 6-sialyltransferase (or both α-2,3- and α-2,6-sialyltransferases) and/or TPST-1 and TPST-2 enzymes responsible for tyrosine-O-sulfation.

5.5 Biomarkers/Sampling/Monitoring Efficacy

Efficacy may be monitored by measuring cognitive function (e.g., prevention or decrease in neurocognitive decline); reductions in biomarkers of disease (such as GAG) in CSF and or serum; and/or increase in IDS enzyme activity in CSF and/or serum. Signs of inflammation and other safety events may also be monitored.

5.5.1. Disease Markers

In certain embodiments, efficacy of treatment with the recombinant vector is monitored by measuring the level of a disease biomarker in the patient. In certain embodiments, the level of the disease biomarker is measured in the CSF of the patient. In certain embodiments, the level of the disease biomarker is measured in the serum of the patient. In certain embodiments, the level of the disease biomarker is measured in the urine of the patient. In certain embodiments, the disease biomarker is GAG. In certain embodiments, the disease biomarker is IDS enzyme activity. In certain embodiments, the disease biomarker is inflammation. In certain embodiments, the disease biomarker is a safety event.

5.5.2. Tests for Neurocognitive Function

In certain embodiments, efficacy of treatment with the recombinant vector is monitored by measuring the level of cognitive function in the patient. Cognitive function may be measured by any method known to one of skill in the art. In certain embodiments, cognitive function is measured via a validated instrument for measuring intelligence quotient (IQ). In specific embodiments, IQ is measured by Wechsler Abbreviated Scale of Intelligence, Second Edition (WASI-II). In certain embodiments, cognitive function is measured via a validated instrument for measuring memory. In specific embodiments, memory is measured by Hopkins Verbal Learning Test (HVLT). In certain embodiments, cognitive function is measured via a validated instrument for measuring attention. In specific embodiments, attention is measured by Test Of Variables of Attention (TOVA). In certain embodiments, cognitive function is measured via a validated instrument for measuring one or more of IQ, memory, and attention.

5.5.3. Physical Changes

In certain embodiments, efficacy of treatment with the recombinant vector is monitored by measuring physical characteristics associated with lysosomal storage deficiency in the patient. In certain embodiments, the physical characteristics are storage lesions. In certain embodiments, the physical characteristic is short stature. In certain embodiments, the physical characteristic is coarsened facial features. In certain embodiments, the physical characteristic is obstructive sleep apnea. In certain embodiments, the physical characteristic is hearing impairment. In certain embodiments, the physical characteristic is vision impairment. In specific embodiments, the visual impairment is due to corneal clouding. In certain embodiments, the physical characteristic is hydrocephalus. In certain embodiments, the physical characteristic is spinal cord compression. In certain embodiments, the physical characteristic is hepatosplenomegaly. In certain embodiments, the physical characteristics are bone and joint deformities. In certain embodiments, the physical characteristic is cardiac valve disease. In certain embodiments, the physical characteristics are recurrent upper respiratory infections. In certain embodiments, the physical characteristic is carpal tunnel syndrome. In certain embodiments, the physical characteristic is macroglossia (enlarged tongue). In certain embodiments, the physical characteristic is enlarged vocal cords and/or change in voice. Such physical characteristics may be measured by any method known to one of skill in the art.

| TABLE OF SEQUENCES | | |
|---|---|---|
| SEQ ID NO: | Description | Sequence |
| 1 | Human IDS amino acid sequence | MPPPRTGRGL LWLGLVLSSV CVALGSETQA NSTTDALNVL LIIVDDLRPS LGCYGDKLVR SPNIDQLASH SLLFQNAFAQ QAVCAPSRVS FLTGRRPDTT RLYDFNSYWR VHAGNFSTIP QYFKENGYVT MSVGKVFHPG ISSNHTDDSP YSWSFPPYHP SSEKYENTKT CRGPDGELHA NLLCPVDVLD VPEGTLPDKQ STEQAIQLLE KMKTSASPFF LAVGYHKPHI PFRYPKEFQK LYPLENITLA PDPEVPDGLP PVAYNPWMDI RQREDVQALN ISVPYGPIPV DFQRKIRQSY FASVSYLDTQ VGRLLSALDD LQLANSTIIA FTSDHGWALG EHGEWAKYSN FDVATHVPLI FYVPGRTASL PEAGEKLFPY LDPFDSASQL MEPGRQSMDL VELVSLFPTL AGLAGLQVPP RCPVPSFHVE LCREGKNLLK HFRFRDLEED PYLPGNPREL IAYSQYPRPS DIPQWNSDKP SLKDIKIMGY SIRTIDYRYT VWVGFNPDEF LANFSDIHAG ELYFVDSDPL QDHNMYNDSQ GGDLFQLLMP |

-continued

TABLE OF SEQUENCES

| SEQ ID NO: | Description | Sequence |
|---|---|---|
| 2 | Oligodendrocyte-myelin glycoprotein (hOMG) signal peptide | MEYQILKMSL CLFILLFLTP GILC |
| 3 | Cellular repressor of E1A-stimulated genes 2 (hCREG2) signal peptide | MSVRRGRRPA RPGTRLSWLL CCSALLSPAAG |
| 4 | V-set and transmembrane domain containing 2B (hVSTM2B) signal peptide | MEQRNRLGAL GYLPPLLLHA LLLFVADA |
| 5 | Protocadherin alpha-1 (hPCADHA1) signal peptide | MVFSRRGGLG ARDLLLWLLL LAAWEVGSG |
| 6 | FAM19A1 (TAFA1) signal peptide | MAMVSAMSWV LYLWISACA |
| 7 | VEGF-A signal peptide | MNFLLSWVHW SLALLLYLHH AKWSQA |
| 8 | Fibulin-1 signal peptide | MERAAPSRRV PLPLLLLGGL ALLAAGVDA |
| 9 | Vitronectin signal peptide | MAPLRPLLIL ALLAWVALA |
| 10 | Complement Factor H signal peptide | MRLLAKIICL MLWAICVA |
| 11 | Opticin signal peptide | MRLLAFLSLL ALVLQETGT |
| 12 | Albumin signal peptide | MKWVTFISLL FLFSSAYS |
| 13 | Chymotrypsinogen signal peptide | MAFLWLLSCW ALLGTTFG |
| 14 | Interleukin-2 signal peptide | MYRMQLLSCI ALILALVTNS |
| 15 | Trypsinogen-2 signal peptide | MNLLLILTFV AAAVA |
| 16 | AAV1 | MAADGYLPDWLEDNLSEGIREWWDLKPGAPKPKANQQKQD DGRGLVLPGYKYLGPFNGLDKGEPVNAADAAALEHDKAYD QQLKAGDNPYLRYNHADAEFQERLQEDTSFGGNLGRAVFQ AKKRVLEPLGLVEEGAKTAPGKKRPVEQSPQEPDSSSGIG KTGQQPAKKRLNFGQTGDSESVPDPQPLGEPPATPAAVGP TTMASGGGAPMADNNEGADGVGNASGNWHCDSTWLGDRVI TTSTRTWALPTYNNHLYKQISSASTGASNDNHYFGYSTPW GYFDFNRFHCHFSPRDWQRLINNNWGFRPKRLNFKLFNIQ VKEVTTNDGVTTIANNLTSTVQVFSDSEYQLPYVLGSAHQ GCLPPFPADVFMIPQYGYLTLNNGSQAVGRSSFYCLEYFP SQMLRTGNNFTFSYTFEEVPFHSSYAHSQSLDRLMNPLID QYLYYLNRTQNQSGSAQNKDLLFSRGSPAGMSVQPKNWLP GPCYRQRVSKTKTDNNNSNFTWTGASKYNLNGRESIINP GTAMASHKDDEDKFFPMSGVMIFGKESAGASNTALDNVMI TDEEEIKATNPVATERFGTVAVNFQSSSTDPATGDVHAMG ALPGMVWQDRDVYLQGPIWAKIPHTDGHFHPSPLMGGFGL |

TABLE OF SEQUENCES

| SEQ ID NO: | Description | Sequence |
|---|---|---|
|  |  | KNPPPQILIKNTPVPANPPAEFSATKFASFITQYSTGQVS VEIEWELQKENSKRWNPEVQYTSNYAKSANVDFTVDNNGL YTEPRPIGTRYLTRPL |
| 17 | AAV2 | MAADGYLPDWLEDTLSEGIRQWWKLKPGPPPPKPAERHKD DSRGLVLPGYKYLGPFNGLDKGEPVNEADAAALEHDKAYD RQLDSGDNPYLKYNHADAEFQERLKEDTSFGGNLGRAVFQ AKKRVLEPLGLVEEPVKTAPGKKRPVEHSPVEPDSSSGIG KAGQQPARKRLNFGQTGDADSVPDPQPLGQPPAAPSGLGT NTMATGSGAPMADNNEGADGVGNSSGNWHCDSTWMGDRVI TTSTRTWALPTYNNHLYKQISSQSGASNDNHYFGYSTPWG YFDFNRFHCHFSPRDWQRLINNNWGFRPKRLNFKLFNIQV KEVTQNDGTTTIANNLTSTVQVFTDSEYQLPYVLGSAHQG CLPPFPADVFMVPQYGYLTLNNGSQAVGRSSFYCLEYFPS QMLRTGNNFTFSYTFEDVPFHSSYAHSQSLDRLMNPLIDQ YLYYLSRTNTPSGTTTQSRLQFSQAGASDIRDQSRNWLPG PCYRQQRVSKTSADNNNSEYSWTGATKYHLNGRDSLVNPG PAMASHKDDEEKFFPQSGVLIFGKQGSEKTNVDIEKVMIT DEEEIRTTNPVATEQYGSVSTNLQRGNRQAATADVNTQGV LPGMVWQDRDVYLQGPIWAKIPHTDGHFHPSPLMGGFGLK HPPPQILIKNTPVPANPSTTFSAAKFASFITQYSTGQVSV EIEWELQKENSKRWNPEIQYTSNYNKSVNVDFTVDTNGVY SEPRPIGTRYLTRNL |
| 18 | AAV3-3 | MAADGYLPDWLEDNLSEGIREWWALKPGVPQPKANQQHQD NRRGLVLPGYKYLGPGNGLDKGEPVNEADAAALEHDKAYD QQLKAGDNPYLKYNHADAEFQERLQEDTSFGGNLGRAVFQ AKKRILEPLGLVEEAAKTAPGKKGAVDQSPQEPDSSSGVG KSGKQPARKRLNFGQTGDSESVPDPQPLGEPPAAPTSLGS NTMASGGGAPMADNNEGADGVGNSSGNWHCDSQWLGDRVI TTSTRTWALPTYNNHLYKQISSQSGASNDNHYFGYSTPWG YFDFNRFHCHFSPRDWQRLINNNWGFRPKKLSFKLFNIQV RGVTQNDGTTTIANNLTSTVQVFTDSEYQLPYVLGSAHQG CLPPFPADVFMVPQYGYLTLNNGSQAVGRSSFYCLEYFPS QMLRTGNNFQFSYTFEDVPFHSSYAHSQSLDRLMNPLIDQ YLYYLNRTQGTTSGTTNQSRLLFSQAGPQSMSLQARNWLP GPCYRQQRLSKTANDNNSNFPWTAASKYHLNGRDSLVNP GPAMASHKDDEEKFFPMHGNLIFGKEGTTASNAELDNVMI TDEEEIRTTNPVATEQYGTVANNLQSSNTAPTTGTVNHQG ALPGMVWQDRDVYLQGPIWAKIPHTDGHFHPSPLMGGFGL KHPPPQIMIKNTPVPANPPTTFSPAKFASFITQYSTGQVS VEIEWELQKENSKRWNPEIQYTSNYNKSVNVDFTVDTNGV YSEPRPIGTRYLTRNL |
| 19 | AAV4-4 | MTDGYLPDWLEDNLSEGVREWWALQPGAPKPKANQQHQDN ARGLVLPGYKYLGPGNGLDKGEPVNAADAAALEHDKAYDQ QLKAGDNPYLKYNHADAEFQQRLQGDTSFGGNLGRAVFQA KKRVLEPLGLVEQAGETAPGKKRPLIESPQQPDSSTGIGK KGKQPAKKKLVFEDETGAGDGPPEGSTSGAMSDDSEMRAA AGGAAVEGGQGADGVGNASGDWHCDSTWSEGHVTTTSTRT WVLPTYNNHLYKRLGESLQSNTYNGFSTPWGYFDFNRFHC HFSPRDWQRLINNNWGMRPKAMRVKIFNIQVKEVTTSNGE TTVANNLTSTVQIFADSSYELPYVMDAGQEGSLPPFPNDV FMVPQYGYCGLVTGNTSQQQTDRNAFYCLEYFPSQMLRTG NNFEITYSFEKVPFHSMYAHSQSLDRLMNPLIDQYLWGLQ STTTGTTLNAGTATTNFTKLRPTNFSNFKKNWLPGPSIKQ QGFSKTANQNYKIPATGSDSLIKYETHSTLDGRWSALTPG PPMATAGPADSKFSNSQLIFAGPKQNGNTATVPGTLIFTS EEELAATNATDTDMWGNLPGGDQSNSNLPTVDRLTALGAV PGMVWQNRDIYYQGPIWAKIPHTDGHFHPSPLIGGFGLKH PPPQIFIKNTPVPANPATTFSSTPVNSFITQYSTGQVSVQ IDWEIQKERSKRWNPEVQFTSNYGQQNSLLWAPDAAGKYT EPRAIGTRYLTHHL |
| 20 | AAV5 | MSFVDHPPDWLEEVGEGLREFLGLEAGPPKPKPNQQHQDQ ARGLVLPGYNYLGPGNGLDRGEPVNRADEVAREHDISYNE QLEAGDNPYLKYNHADAEFQEKLADDTSFGGNLGKAVFQA KKRVLEPFGLVEEGAKTAPTGKRIDDHFPKRKKARTEEDS KPSTSSDAEAGPSGSQQLQIPAQPASSLGADTMSAGGGGP LGDNNQGADGVGNASGDWHCDSTWMGDRVVTKSTRTWVLP SYNNHQYREIKSGSVDGSNANAYFGYSTPWGYFDFNRFHS HWSPRDWQRLINNYWGFRPRSLRVKIFNIQVKEVTVQDST TTIANNLTSTVQVFTDDDYQLPYVVGNGTEGCLPAFPPQV FTLPQYGYATLNRDNTENPTERSSFFCLEYFPSKMLRTGN |

TABLE OF SEQUENCES

| SEQ ID NO: | Description | Sequence |
|---|---|---|
| | | NFEFTYNFEEVPFHSSFAPSQNLFKLANPLVDQYLYRFVS TNNTGGVQFNKNLAGRYANTYKNWFPGPMGRTQGWNLGSG VNRASVSAFATTNRMELEGASYQVPPQPNGMTNNLQGSNT YALENTMIFNSQPANPGTTATYLEGNMLITSESETQPVNR VAYNVGGQMATNNQSSTTAPATGTYNLQEIVPGSVWMERD VYLQGPIWAKIPETGAHFHPSPAMGGFGLKHPPPMMLIKN TPVPGNIISFSDVPVSSFITQYSTGQVTVEMEWELKKENS KRWNPEIQYTNNYNDPQFVDFAPDSTGEYRTTRPIGTRYL TRPL |
| 21 | AAV6 | MAADGYLPDWLEDNLSEGIREWWDLKPGAPKPKANQQKQD DGRGLVLPGYKYLGPFNGLDKGEPVNAADAAALEHDKAYD QQLKAGDNPYLRYNHADAEFQERLQEDTSFGGNLGRAVFQ AKKRVLEPFGLVEEGAKTAPGKKRPVEQSPQEPDSSSGIG KTGQQPAKKRLNFGQTGDSESVPDPQPLGEPPATPAAVGP TTMASGGGAPMADNNEGADGVGNASGNWHCDSTWLGDRVI TTSTRTWALPTYNNHLYKQISSASTGASNDNHYFGYSTPW GYFDFNRFHCHFSPRDWQRLINNNWGFRPKRLNFKLFNIQ VKEVTTNDGVTTIANNLTSTVQVFSDSEYQLPYVLGSAHQ GCLPPFPADVFMIPQYGYLTLNNGSQAVGRSSFYCLEYFP SQMLRTGNNFTFSYTFEDVPFHSSYAHSQSLDRLMNPLID QYLYYLNRTQNQSGSAQNKDLLFSRGSPAGMSVQPKNWLP GPCYRQQRVSKTKTDNNSNFTWTGASKYNLNGRESIINP GTAMASHKDDKDKFFPMSGVMIFGKESAGASNTALDNVMI TDEEEIKATNPVATERFGTVAVNLQSSSTDPATGDVHVMG ALPGMVWQDRDVYLQGPIWAKIPHTDGHFHPSPLMGGFGL KHPPPQILIKNTPVPANPPAEFSATKFASFITQYSTGQVS VEIEWELQKENSKRWNPEVQYTSNYAKSANVDFTVDNNGL YTEPRPIGTRYLTRPL |
| 22 | AAV7 | MAADGYLPDWLEDNLSEGIREWWDLKPGAPKPKANQQKQD NGRGLVLPGYKYLGPFNGLDKGEPVNAADAAALEHDKAYD QQLKAGDNPYLRYNHADAEFQERLQEDTSFGGNLGRAVFQ AKKRVLEPLGLVEEGAKTAPAKKRPVEPSPQRSPDSSTGI GKKGQQPARKRLNFGQTGDSESVPDPQPLGEPPAAPSSVG SGTVAAGGGAPMADNNEGADGVGNASGNWHCDSTWLGDRV ITTSTRTWALPTYNNHLYKQISSETAGSTNDNTYFGYSTP WGYFDFNRFHCHFSPRDWQRLINNNWGFRPKKLRFKLFNI QVKEVTTNDGVTTIANNLTSTIQVFSDSEYQLPYVLGSAH QGCLPPFPADVFMIPQYGYLTLNNGSQSVGRSSFYCLEYF PSQMLRTGNNFEFSYSFEDVPFHSSYAHSQSLDRLMNPLI DQYLYYLARTQSNPGGTAGNRELQFYQGGPSTMAEQAKNW LPGPCFRQQRVSKTLDQNNNSNFAWTGATKYHLNGRNSLV NPGVAMATHKDDEDRFFPSSGVLIFGKTGATNKTTLENVL MTNEEEIRPTNPVATEEYGIVSSNLQAANTAAQTQVVNNQ GALPGMVWQNRDVYLQGPIWAKIPHTDGNFHPSPLMGGFG LKHPPPQILIKNTPVPANPPEVFTPAKFASFITQYSTGQV SVEIEWELQKENSKRWNPEIQYTSNFEKQTGVDFAVDSQG VYSEPRPIGTRYLTRNL |
| 23 | AAV8 | MAADGYLPDWLEDNLSEGIREWWALKPGAPKPKANQQKQD DGRGLVLPGYKYLGPFNGLDKGEPVNAADAAALEHDKAYD QQLQAGDNPYLRYNHADAEFQERLQEDTSFGGNLGRAVFQ AKKRVLEPLGLVEEGAKTAPGKKRPVEPSPQRSPDSSTGI GKKGQQPARKRLNFGQTGDSESVPDPQPLGEPPAAPSGVG PNTMAAGGGAPMADNNEGADGVGSSSGNWHCDSTWLGDRV ITTSTRTWALPTYNNHLYKQISNGTSGGATNDNTYFGYST PWGYFDFNRFHCHFSPRDWQRLINNNWGFRPKRLSFKLFN IQVKEVTQNEGTKTIANNLTSTIQVFTDSEYQLPYVLGSA HQGCLPPFPADVFMIPQYGYLTLNNGSQAVGRSSFYCLEY FPSQMLRTGNNFQFTYTFEDVPFHSSYAHSQSLDRLMNPL IDQYLYYLSRTQTTGGTANTQTLGFSQGGPNTMANQAKNW LPGPCYRQQRVSTITGQNNNSNFAWTAGTKYHLNGRNSLA NPGIAMATHKDDEERFFPSNGILIFGKQNAARDNADYSDV MLTSEEEIKTTNPVATEEYGIVADNLQQQNTAPQIGTVNS QGALPGMVWQNRDVYLQGPIWAKIPHTDGNFHPSPLMGGF GLKHPPPQILIKNTPVPADPPTTFNQSKLNSFITQYSTGQ VSVEIEWELQKENSKRWNPEIQYTSNYYKSTSVDFAVNTE GVYSEPRPIGTRYLTRNL |
| 24 | hu31 | MAADGYLPDWLEDTLSEGIRQWWKLKPGPPPPKPAERHKD DSRGLVLPGYKYLGPGNGLDKGEPVNAADAAALEHDKAYD QQLKAGDNPYLKYNHADAEFQERLKEDTSFGGNLGRAVFQ AKKRLLEPLGLVEEAAKTAPGKKRPVEQSPQEPDSSAGIG |

TABLE OF SEQUENCES

| SEQ ID NO: | Description | Sequence |
|---|---|---|
| | | KSGSQPAKKKLNFGQTGDTESVPDPQPIGEPPAAPSGVGS<br>LTMASGGGAPVADNNEGADGVGSSSGNWHCDSQWLGDRVI<br>TTSTRTWALPTYNNHLYKQISNSTSGGSSNDNAYFGYSTP<br>WGYFDFNRFHCHFSPRDWQRLINNNWGFRPKRLNFKLFNI<br>QVKEVTDNNGVKTIANNLTSTVQVFTDSDYQLPYVLGSAH<br>EGCLPPFPADVFMIPQYGYLTLNDGGQAVGRSSFYCLEYF<br>PSQMLRTGNNFQFSYEFENVPFHSSYAHSQSLDRLMNPLI<br>DQYLYYLSKTINGSGQNQQTLKFSVAGPSNMAVQGRNYIP<br>GPSYRQQRVSTTVTQNNNSEFAWPGASSWALNGRNSLMNP<br>GPAMASHKEGEDRFFPLSGSLIFGKQGTGRDNVDADKVMI<br>TNEEEIKTTNPVATESYGQVATNHQSAQAQAQTGWVQNQG<br>ILPGMVWQDRDVYLQGPIWAKIPHTDGNFHPSPLMGGFGM<br>KHPPPQILIKNTPVPADPPTAFNKDKLNSFITQYSTGQVS<br>VEIEWELQKENSKRWNPEIQYTSNYYKSNNVEFAVSTEGV<br>YSEPRPIGTRYLTRNL |
| 25 | hu32 | MAADGYLPDWLEDTLSEGIRQWWKLKPGPPPPKPAERHKD<br>DSRGLVLPGYKYLGPGNGLDKGEPVNAADAAALEHDKAYD<br>QQLKAGDNPYLKYNHADAEFQERLKEDTSFGGNLGRAVFQ<br>AKKRLLEPLGLVEEAAKTAPGKKRPVEQSPQEPDSSAGIG<br>KSGSQPAKKKLNFGQTGDTESVPDPQPIGEPPAAPSGVGS<br>LTMASGGGAPVADNNEGADGVGSSSGNWHCDSQWLGDRVI<br>TTSTRTWALPTYNNHLYKQISNSTSGGSSNDNAYFGYSTP<br>WGYFDFNRFHCHFSPRDWQRLINNNWGFRPKRLNFKLFNI<br>QVKEVTDNNGVKTIANNLTSTVQVFTDSDYQLPYVLGSAH<br>EGCLPPFPADVFMIPQYGYLTLNDGSQAVGRSSFYCLEYF<br>PSQMLRTGNNFQFSYEFENVPFHSSYAHSQSLDRLMNPLI<br>DQYLYYLSKTINGSGQNQQTLKFSVAGPSNMAVQGRNYIP<br>GPSYRQQRVSTTVTQNNNSEFAWPGASSWALNGRNSLMNP<br>GPAMASHKEGEDRFFPLSGSLIFGKQGTGRDNVDADKVMI<br>TNEEEIKTTNPVATESYGQVATNHQSAQAQAQTGWVQNQG<br>ILPGMVWQDRDVYLQGPIWAKIPHTDGNFHPSPLMGGFGM<br>KHPPPQILIKNTPVPADPPTAFNKDKLNSFITQYSTGQVS<br>VEIEWELQKENSKRWNPEIQYTSNYYKSNNVEFAVNTEGV<br>YSEPRPIGTRYLTRNL |
| 26 | AAV9 | MAADGYLPDWLEDNLSEGIREWWALKPGAPQPKANQQHQD<br>NARGLVLPGYKYLGPGNGLDKGEPVNAADAAALEHDKAYD<br>QQLKAGDNPYLKYNHADAEFQERLKEDTSFGGNLGRAVFQ<br>AKKRLLEPLGLVEEAAKTAPGKKRPVEQSPQEPDSSAGIG<br>KSGAQPAKKRLNFGQTGDTESVPDPQPIGEPPAAPSGVGS<br>LTMASGGGAPVADNNEGADGVGSSSGNWHCDSQWLGDRVI<br>TTSTRTWALPTYNNHLYKQISNSTSGGSSNDNAYFGYSTP<br>WGYFDFNRFHCHFSPRDWQRLINNNWGFRPKRLNFKLFNI<br>QVKEVTDNNGVKTIANNLTSTVQVFTDSDYQLPYVLGSAH<br>EGCLPPFPADVFMIPQYGYLTLNDGSQAVGRSSFYCLEYF<br>PSQMLRTGNNFQFSYEFENVPFHSSYAHSQSLDRLMNPLI<br>DQYLYYLSKTINGSGQNQQTLKFSVAGPSNMAVQGRNYIP<br>GPSYRQQRVSTTVTQNNNSEFAWPGASSWALNGRNSLMNP<br>GPAMASHKEGEDRFFPLSGSLIFGKQGTGRDNVDADKVMI<br>TNEEEIKTTNPVATESYGQVATNHQSAQAQAQTGWVQNQG<br>ILPGMVWQDRDVYLQGPIWAKIPHTDGNFHPSPLMGGFGM<br>KHPPPQILIKNTPVPADPPTAFNKDKLNSFITQYSTGQVS<br>VEIEWELQKENSKRWNPEIQYTSNYYKSNNVEFAVNTEGV<br>YSEPRPIGTRYLTRNL |
| 27 | SP\|P22304\|<br>IDS_HUMAN<br>[Homo<br>sapiens] | MPPPRTGRGLLWLGLVLSSVCVALGSETQANSTTDALNVL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGISSNHTDDSPYSWSFPPYHP<br>SSEKYENTKTCRGPDGELHANLLCPVDVLDVPEGTLPDKQ<br>STEQAIQLLEKMKTSASPFFLAVGYHKPHIPFRYPKEFQK<br>LYPLENITLAPDPEVPDGLPPVAYNPWMDIRQREDVQALN<br>ISVPYGPIPVDFQRKIRQSYFASVSYLDTQVGRLLSALDD<br>LQLANSTIIAFTSDHGWALGEHGEWAKYSNFDVATHVPLI<br>FYVPGRTASLPEAGEKLFPYLDPFDSASQLMEPGRQSMDL<br>VELVSLFPTLAGLAGLQVPPRCPVPSFHVELCREGKNLLK<br>HFRFRDLEEDPYLPGNPRELIAYSQYPRPSDIPQWNSDKP<br>SLKDIKIMGYSIRTIDYRYTVWVGFNPDEFLANFSDIHAG<br>ELYFVDSDPLQDHNMYNDSQGGDLFQLLMP |

TABLE OF SEQUENCES

| SEQ ID NO: | Description | Sequence |
|---|---|---|
| 28 | TR\|K6ZGI9_PANTR [*Pan troglodytes* (Chimpanzee)] | MPPPRTGRGLPWLGLVLSSVCVALGSETQANSTTDALNVLLIIVDDLRPSLGCYGDKLVRSPNIDQLASHSLLFQNAFAQQAVCAPSRVSFLTGRRPDTRLYDFNSYWRVHAGNFSTIPQYFKENGYVTMSVGKVFHPGISSNHTDDSPYSWSFPPYHPSSEKYENTKTCRGPDGELHANLLCPVDVLDVPEGTLPDKQSTEQAIQLLEKMKTSASPFFLAVGYHKPHIPFRYPKEFQKLYPLENITLAPDPEVPDGLPPVAYNPWMDIRQREDVQALNISVPYGPIPVDFQRKIRQSYFASVSYLDTQVGRLLSALDDLQLANSTIIAFTSDHGWALGEHGEWAKYSNFDVATHVPLMFYVPGRTASLPEAGEKLFPYLDPFDSASQLMEPGRQSMDLVELVSLFPTLAGLAGLQAPPRCPVPSFHVELCREGKNLLKHFRFRDLEEDPYLPGNPRELIAYSQYPRPSDIPQWNSDKPSLKDIKIMGYSIRTIDYRYTVWIGFNPDEFLANFSDIHAGELYFVDSDPLQDHNMYNDSQGGDLFQLLMP |
| 29 | TR\|K7BKV4_PANTR [*Pan troglodytes* (Chimpanzee)] | MPPPRTGRGLPWLGLVLSSVCVALGSETQANSTTDALNVLLIIVDDLRPSLGCYGDKLVRSPNIDQLASHSLLFQNAFAQQAVCAPSRVSFLTGRRPDTRLYDFNSYWRVHAGNFSTIPQYFKENGYVTMSVGKVFHPGISSNHTDDSPYSWSFPPYHPSSEKYENTKTCRGPDGELHANLLCPVDVLDVPEGTLPDKQSTEQAIQLLEKMKTSASPFFLAVGYHKPHIPFRYPKEFQKLYPLENITLAPDPEVPDGLPPVAYNPWMDIRQREDVQALNISVPYGPIPVDFQRKIRQSYFASVSYLDTQVGRLLSALDDLQLANSTIIAFTSDHGWALGEHGEWAKYSNFDVATHVPLMFYVPGRTASLPEAGEKLFPYLDPFDSASQLMEPGRQSMDLVELVSLFPTLAGLAGLQAPPRCPVPSFHVELCREGKNLLKHFRFRDLEEDPYLPGNPRELIAYSQYPRPSDIPQWNSDKPSLKDIKIMGYSIRTIDYRYTVWIGFNPDEFLANFSDIHAGELYFVDSDPLQDHNMYNDSQGGDLFQLLMP |
| 30 | TR\|H9FTX2_MACMU [*Macaca mulatta* (Rhesus macaque)] | MPTPGSGRGFLWLGLVLSSVCVALGCETQANSTTDALNILLIIVDDLRPSLGCYGDKLVRSPNIDQLASHSLLFQNAFAQQAVCAPSRVSFLTGRRPDTTRLYDFNSYWRVHAGNFSTIPQYFKENGYVTMSVGKVFHPGITSNHTDDSPYSWSFPPYHPSSEKYENTKTCRGPDGELHANLLCPVDVVDVPEGTLPDKQSTEQAIQLLEKMKTSASPFFLAVGYHKPHIPFRYPKEFQKLYPLENITLAPDSEVPDGLPPVAYNPWMDIRQREDVQALNISVPYGPIPVEFQRKIRQSYFASVSYLDTQVGRLLSALDDLQLANSTIVAFTSDHGWALGEHGEWAKYSNFDVATHVPLMFYVPGRTASLPEAGEKLFPYLDPFDSASELMEPGRQSMDLVELVSLFPTLAGLAGLQVPPRCPVPSFHVELCREGKNLLKHFRFRDLEEDPYLPGNPRELIAYSQYPRPADFPQWNSDKPSLKDIKIMGYSIRTIDYRYTVWVGFNPDEFLANFSDIHAGELYFVDSDPLQDHNMYNDSQGGDLFQLLMP |
| 31 | TRF7EJG2_CALJA [*Callithrix jacchus* (White-tufted-ear marmoset)] | MPPPRTSRCLLLLGLVLGSVCVTLGSQAQASSTTDALNVLLIIVDDLRPSLGCYGDKLVRSPNIDQLASHSLLFQNAFAQQAVCAPSRVSFLTGRRPDTTRLYDFNSYWRVHAGNFSTIPQYFKDNGYVTMSVGKVFHPGISSNHSDDSPYSWSFPPYHPSSEKYENTKTCRGPDGELHANLLCPVDVVDVPEGTLPDKQSTEEAIRLLEKMKTSASPFFLAVGYHKPHIPFRYPKEFQKLYPLENITLAPDPEVPDGLPPVAYNPWMDIRQREDVQALNISVPYGPIPVDFQRKIRQSYFASVSYLDTQVGHLLSALDDLQLANSTIVAFTSDHGWALGEHGEWAKYSNFDVATRVPLMFYVPGRTASLPEADEKLFPYVDPFHSASELMEPGRQSMDLVELVSLFPTLAGLAGLQVPPRCPVPSFHVELCREGKSLLKHFRFHGLEEDPYLPGNPRELIAYSQYPRPADFPQWNSDKPSLKYIKIMGYSIRTVDYRYTVWVGFNPDEFLANFSDIHAGELYFVDSDPLQDHNMYNDSQGGELFQSLMP |
| 32 | TR\|U3DTL8_CALJA [*Callithrix jacchus* (White-tufted-ear marmoset)] | MPPPRPSRCLLLLGLVLGSVCVTLGSQAQASSTTDALNVLLIIVDDLRPSLGCYGDKLVRSPNIDQLASHSLLFQNAFAQQAVCAPSRVSFLTGRRPDTTRLYDFNSYWRVHAGNFSTIPQYFKDNGYVTMSVGKVFHPGISSNHSDDSPYSWSFPPYHPSSEKYENTKTCRGPDGELHANLLCPVDVVDVPEGTLPDKQSTEEAIRLLEKMKTSASPFFLAVGYHKPHIPFRYPKEFQKLYPLENITLAPDPEVPDGLPPVAYNPWMDIRQREDVQALNISVPYGPIPVDFQRKIRQSYFASVSYLDTQVGHLLSALDDLQLANSTIVAFTSDHGWALGEHGEWAKYSNFDVATRVPLMFYVPGRTASLPEADEKLFPYVDPFHSASELMEPGRQSMDLVELVSLFPTLAGLAGLQVPPRCPVPSFHVELCREGKSLLKHFRFHGLEEDPYLPGNPRELIAYSQYPRPADFPQWNSDKPSLKYIKIMGYSIRTVDYRYTVWVGFNPDEFLANFSDIHAGELYFVDSDPLQDHNMYNDSQGGELFQSLMP |

| SEQ ID NO: | Description | Sequence |
|---|---|---|
| 33 | TR\|G7NRX7_MACMU [*Macaca mulatta* (Rhesus macaque)] | MPTPGSGRGFLWLGLVLSSVCVALGCETQANSTTDALNIL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGITSNHTDDSPYSWSFPPYHP<br>SSEKYENTKTCRGPDGELHANLLCPVDVVDVPEGTLPDKQ<br>STEQAIQLLEKMKTSASPFFLAVGYHKPHIPFRYPKEFQK<br>LYPLENITLAPDSEVPDGLPPVAYNPWMDIRQREDVQALN<br>ISVPYGPIPVEFQRKIRQSYFASVSYLDTQVGRLLSALDD<br>LQLANSTIVAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK<br>HFRFRDLEEDPYLPGNPRELIAYSQYPRPADFPQWNSDKP<br>SLKDIKIMGYSIRTIDYRYTVWVGFNPDEFLANFSDIHAG<br>ELYFVDSDPLQDHNMYNDSQGGDLLQLLMP |
| 34 | TR\|G7Q1V9_MACFA [*Macaca fascicularis* (Crab-eating macaque; Cynomologous monkey)] | MPTPGSGRGFLWLGLVLSSVCVALGCETQANSTTDALNIL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGITSNHTDDSPYSWSFPPYHP<br>SSEKYENTKTCRGPDGELHANLLCPVDVVDVPEGTLPDKQ<br>STEQAIQLLEKMKTSASPFFLAVGYHKPHIPFRYPKEFQK<br>LYPLENITLAPDSEVPDGLPPVAYNPWMDIRQREDVQALN<br>ISVPYGPIPVEFQRKIRQSYFASVSYLDTQVGHLLSALDD<br>LQLANSTIVAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK<br>HFRFRDLEEDPYLPGNPRELIAYSQYPRPADFPQWNSDKP<br>SLKDIKIMGYSIRTIDYRYTVWVGFNPDEFLANFSDIHAG<br>ELYFVDSDPLQDHNMYNDSQGGDLFQLLMP |
| 35 | TR\|E12PX10_PONAB [*Pongo abelii* (Sumatran orangutan)] | MPPPRTGRGLLWLGLVLSSVCVALGSETQADSTTDGLNVL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGISSNHTDDSPYSWSFPPYHP<br>SSEKYENTKTCRGPDGELHANLIAKKMCWMFPRAPCCDKQ<br>STEQAIQLLEKMKTSASPFFLAVGYHKPHIPFRYPKEFQK<br>LYPLENITLAPDPEVPDGLPPVAYNPWMDIRQREDVQALN<br>ISVPYGPIPVDFQQKIRQSYFASVSYLDTQVGRLLSTLDD<br>LQLANSTIIAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK<br>HFRFRDLEEDPYLPGNPRELIAYSQYPRPADIPQWNSDKP<br>SLKDIKIMGYSIRTIDYRYTVWVGFNPDEFLANFSDIHAG<br>ELYFVDSDPLQDHNMYNDSQGGDLFQLLMP |
| 36 | TR\|A0A0D9R4D1_CHLSB [*Chlorocebus sabaeus* (Green monkey)] | MPTPGSGRGFLWLGLVLSSVCVALGSETQANSTTDALNIL<br>LIIVDDLRPSLGCYGDKLVRSPNIDQLASHSLLFQNAFAQ<br>QAVCAPSRVSFLTGRRPDTTRLHNFNSYWRVHAGNFSTIP<br>QYFKENGYVTMSVGKVFHPGITSNHTDDSPYSWSFPPYHP<br>SSEKYENTKTCRGPDGELHANLLCPVDVVDVPEGTLPDKQ<br>STEQAIQLLEKMKTSASPFFLAVGYHKPHIPFRYPKEFQK<br>LYPLENITLAPDSEVPDGLPPVAYNPWMDIRQREDVQALN<br>ISVPYGPIPVEFQRKIRQSYFASVSYLDTQVGRLLSALDD<br>LQLANSTIVAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK<br>HFRFRDLEEDPYLPGNPRELIAYSQYPRPADFPQWNSDKP<br>NLKDIKIMGYSIRTIDYRYTVWVGFNPDEFLANFSDIHAG<br>ELYFVDSDPLQDHNMYNDSQGGDLFQLLMP |
| 37 | TR\|G1RST8\|G1RST8_NOMLE [*Nomascus leucogenys* (Northern white-cheeked gibbon)] | MSPPRTGQGLLWLGVVLSSVCVAXVTSPKPPSFVDALNVL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGISSNHTDDSPYSWSFPPYHP<br>SSXXXXXXKTCRGPDGELHANLCPVDVLDVPEGTLPDKQ<br>STEQAIQLLEKMKTSASPFFLAVGYHKPHIPFRYPKEFQK<br>LYPLENITLAPDPEVPDGLPPVAYNPWMDIRQREDVQALN<br>ISVPYGPIPVDFQRKIRQSYFASVSYLDTQVGRLLSALDD<br>LQLANSTIIAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK |

TABLE OF SEQUENCES

| SEQ ID NO: | Description | Sequence |
|---|---|---|
| | | HFRFRDLEEDPYLPGNPRELIAYSQYPRPADIPQWNSDKP<br>SLKDIKIMGYSIRTIDYRYTVWVGFSPDEFLANFSDIHAG<br>ELYFVDSDPLQDHNMYNDSQGGDLFQLLMP |
| 38 | UPI0000D9F625<br>[*Macaca mulatta* (Rhesus macaque)] | MPTPGSGRGFLWLGLVLSSVCVALGCETQANSTTDALNIL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGITSNHTDDSPYSWSFPPYHP<br>SSEKYENTKTCRGPDGELHANLLCPVDVVDVPEGTLPDKQ<br>STEQAIQLLEKMKTSASPFFLAVGYHKPHIPFRYPKEFQK<br>LYPLENITLAPDSEVPDGLPPVAYNPWMDIRQREDVQALN<br>ISVPYGPIPVEFQRKIRQSYFASVSYLDTQVGHLLSALDD<br>LQLANSTIVAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK<br>HFRFRDLEEDPYLPGNPRELIAYSQYPRPADFPQWNSDKP<br>SLKDIKIMGYSIRTIDYRYTVWVGFNPDEFLANFSDIHAG<br>ELYFVDSDPLQDHNMYNDSQGGDLLQLLMP |
| 39 | UPI000274358B<br>[*Pan paniscus* (Pygmy chimpanzee; Bonobo)] | MPPPRTGRGLLWLGLVLSSVCVALGSETQANSTTDALNVL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGISSNHTDDSPYSWSFPPYHP<br>SSEKYENTKTCRGPDGELHANLLCPVDVLDVPEGTLPDKQ<br>STEQAIRLLEKMKTSASPFFLAVGYHKPHIPFRYPKEFQK<br>LYPLENITLAPDPEVPDGLPPVAYNPWMDIRQREDVQALN<br>ISVPYGPIPVDFQRKIRQSYFASVSYLDTQVGRLLSALDD<br>LQLANSTIIAFTSDHGWALGEHGEWAKYSNFDVATHVPLM<br>FYVPGRTASLPEAGEKLFPYLDPFDSASQLMEPGRQSMDL<br>VELVSLFPTLAGLAGLQVPPRCPVPSFHVELCREGKNLLK<br>HFRFRDLEEDPYLPGNPRELIAYSQYPRPSDIPQWNSDKP<br>SLKDIKIMGYSIRTIDYRYTVWVGFNPDEFLANFSDIHAG<br>ELYFVDSDPLQDHNMYNDSQGGDLFQLLMP |
| 40 | UPI00027F6FC5<br>[*Papio Anubis* (Olive baboon)] | MPTPGSGRGFLWLGLVLSSVCVALGCEMQANSTTDALNIL<br>LIIVDDLRPSLGCYGDKLVRSPNIDQLASHSLLFQNAFAQ<br>QAVCAPSRVSFLTGRRPDTTRLYDFNSYWRVHAGNFSTIP<br>QYFKENGYVTMSVGKVFHPGITSNHTDDSPYSWSFPPYHP<br>SSEKYENTKTCRGPDGELHANLLCPVDVVDVPEGTLPDKQ<br>STEQAIQLLEKMKTSASPFFLAVGYHKPHIPFRYPKEFQK<br>LYPLENITLAPDSEVPDGLPPVAYNPWMDIRQREDVQALN<br>ISVPYGPIPVEFQRKIRQSYFASVSYLDTQVGRLLSALDD<br>LQLANSTIVAFTSDHGWALGEHGEWAKYSNFDVATHVPLM<br>FYVPGRTASLPEAGEKLFPYLDPFDSASELMEPGRQSMDL<br>VELVSLFPTLAGLAGLQVPPRCPVPSFHVELCREGKNLLK<br>HFRFRDLEEDPYLPGNPRELIAYSQYPRPADFPQWNSDKP<br>SLKDIKIMGYSIRTIDYRYTVWVGFNPDEFLANFSDIHAG<br>ELYFVDSDPLQDHNMYNDSQGGDLFQLLMP |
| 41 | UPI00027FAE03<br>[*Saimiri boliviensis* (Bolivian squirrel monkey)] | MPPPRTGLCLLLLGLVLGSVCVTLGSQAQANSTTDALNVL<br>LIIVDDLRPSLGCYGDKLVRSPNIDQLASHSLLFQNAFVQ<br>QAVCAPSRVSFLTGRRPDTTRLYDFNSYWRVHAGNFSTIP<br>QYFKDNGYVTMSVGKVFHPGISSNHSDDSPYSWSFPPYHP<br>SSEKYENTKTCRGPDGELHANLLCPVDVVDVPEGTLPDKQ<br>STEEAIRLLKKMKTSASPFFLAVGYHKPHIPFRYPKEFQK<br>LYPLENITLAPDPEVPDGLPPVAYNPWMDIRQREDVQALN<br>ISVPYGPIPVDFQRKIRQSYFASVSYLDTQVGHLLSALDD<br>LHLANSTIVAFTSDHGWALGEHGEWAKYSNFDVATRVPLM<br>FYVPGRTASLPETGEKLFPYVDPFHSASELMEPGRQSTDL<br>VELVSLFPTLAGLAGLQVPPRCPVPSFHIELCREGKNLLK<br>HFRFHGLEEDPYLPGNPRELIAYSQYPRPADFPQQNSDKP<br>SLKYIKIMGYSIRTVDYRYTVWVGFNPDEFLANFSDIHAG<br>ELYFVDSDPLQDHNMYNDSQGGELFQSLMP |
| 42 | UPI0003ABBF28<br>[*Macaca fascicularis* (Crab-eating macaque; Cynomologous monkey)] | MPTPGSGRGFLWLGLVLSSVCVALGCETQANSTTDALNIL<br>LIIVDDLRPSLGCYGDKLVRSPNIDQLASHSLLFQNAFAQ<br>EAVCAPSRVSFLTGRRPDTTRLYDFNSYWRVHAGNFSTIP<br>QYFKENGYVTMSVGKVFHPGITSNHTDDSPYSWSFPPYHP<br>SSEKYENTKTCRGPDGELHANLLCPVDVVDVPEGTLPDKQ<br>STEQAIQLLEKMKTSASPFFLAVGYHKPHIPFRYPKEFQK<br>LYPLENITLAPDSEVPDGLPPVAYNPWMDIRQREDVQALN<br>ISVPYGPIPVEFQRKIRQSYFASVSYLDTQVGRLLSALDD<br>LQLANSTIVAFTSDHGWALGEHGEWAKYSNFDVATHVPLM<br>FYVPGRTASLPEAGEKLFPYLDPFDSASELMEPGRQSMDL |

-continued

TABLEOFSEQUENCES

| SEQ ID NO: | Description | Sequence |
|---|---|---|
| | | VELVSLFPTLAGLAGLQVPPRCPVPSFHVELCREGKNLLK HFRFRDLEEDPYLPGNPRELIAYSQYPRPADFPQWNSDKP SLKDIKIMGYSIRTIDYRYTVWVGFNPDEFLANFSDIHAG ELYFVDSDPLQDHNMYNDSQGGDLFQLLMP |
| 43 | UPI000533297F [*Rhinopithecus roxellana* (Golden snub-nosed monkey; Pygathrix roxellana)] | MPTPASGRGFLWLGLVLSSVCVALGSETQANSTTDALNIL LIIVDDLRPSLGCYGDKLVRSPNIDQLASHSLLFQNAFAQ FQAVCAPSRVSFLTGRRPDTTRLYDFNSYWRVHAGNFSTIP QYFKENGYVTMSVGKVFHPGITSNHTDDSPYSWSFPPYHP SSEKYENTKTCRGPDGELHANLLCPVDVVDVPEGTLPDKQ STEQAVQLLEKMKTSASPFFLAVGYHKPHIPFRYPKEFQK LYPLENITLAPDSEVPDGLPPVAYNPWMDIRQREDVQALN ISVPYGPIPVDFQRKIRQSYFASVSYLDTQVGHLLSALDD LQLANSTIVAFTSDHGWALGEHGEWAKYSNFDVATHVPLM FYVPGRTASLPEAGEKLFPYLDPFDSASELMEPGRQSMDL VELVSLFPTLAGLAGLQVPPRCPVPSFHVELCREGKNLLK HFRFRDLEEDPYLPGNPRELIAYSQYPRPADFPQWNSDKP SLKDIKIMGYSIRTIDYRYTVWVGFNPDEFLANFSDIHAG ELYFVDSDPFQDHNMYNDSQGGDLFQLLMP |
| 44 | UPI0005F40BD2 [*Colobus angolensis palliates* (Peters' Angolan colobus)] | MPTPASGRGFLWLGLVLRSVCVALGSETQANSTTDALNIL LIIVDDLRPSLGCYGDKLVRSPNIDQLASHSLLFQNAFAQ QAVCTPSHVSFLTGRRPDTTRLYDFNSYWRVHAGNFSTIP QYFKENGYVTMSVGKVFHPGITSNHTDDSPYSWSFPPYHP SSEKYENTKTCRGPDGELHANLLCPVDVVDVPEGTLPDKQ STEQAIQLLEKMKTSASPFFLAVGYHKPHIPFRYPKEFQK LYPLENITLAPDSEVPDGLPPVAYNPWMDIRQREDVQALN ISVPYGPIPVDFQRKIRQSYFASVSYLDTQVGHLLSALDD LQLANSTIVAFTSDHGWALGEHGEWAKYSNFDVATHVPLM FYVPGRTASLPEAGEKLFPYLDPFDSASELMEPGRQSMDL VELVSLFPTLAGLAGLQVPPRCPVPSFHVELCREGKNLLK HFRFRDLEEDPYLPGNPRELIAYSQYPRPADFPQWNSDKP SLKDIKIMGYSIRTIDYRYTVWVGFNPDEFLANFSDIHAG ELYFVDSDPLQDHNMYNDSQGGDLFQLLMP |

6. EXAMPLES

6.1 Example 1: hIDS cDNA

A hIDS cDNA-based vector is constructed comprising a transgene comprising hIDS (SEQ ID NO:1). The transgene also comprises nucleic acids comprising a signal peptide chosen from the group listed in Table 2. Optionally, the vector additionally comprises a promoter.

6.2 Example 2: Substituted hIDS cDNAs

A hIDS cDNA-based vector is constructed comprising a transgene comprising hIDS having amino acid substitutions, deletions, or additions compared to the hIDS sequence of SEQ ID NO:1, e.g., including but not limited to amino acid substitutions selected from corresponding non-conserved residues in orthologs of IDS shown in FIG. 2, with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inhert Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety. The transgene also comprises nucleic acids comprising a signal peptide chosen from the group listed in Table 2. Optionally, the vector additionally comprises a promoter.

6.3 Example 3: Treatment of MPS II in Animals Models with hIDS or Substituted hIDS An hIDS cDNA-based vector is deemed useful for treatment of MPS II when expressed as a transgene. An animal model for MPS II, for example a mouse model described in Garcia et al., 2007, J Inherit Metab Dis 30: 924-34 or Muenzer et al., 2001, Acta Paediatr Suppl 91:98-99 is administered a recombinant vector that encodes hIDS intrathecally at a dose sufficient to deliver and maintain a therapeutically effective concentration of the transgene product in the CSF of the animal. Following treatment, the animal is evaluated for improvement in symptoms consistent with the disease in the particular animal model.

6.1 Example 4: Treatment of MPS II with hIDS or Substituted hIDS

An hIDS cDNA-based vector is deemed useful for treatment of MPS II when expressed as a transgene. A subject presenting with MPS II is administered a cDNA-based vector that encodes hIDS (e.g., such as Construct 1 (see below) intrathecally at a dose sufficient to deliver and maintain a therapeutic concentration of the transgene product in the CSF. Following treatment, the subject is evaluated for improvement in symptoms of MPS II.

6.2 Example 5: A Phase I/II Multicenter, Open-Label Study to Evaluate the Safety, Tolerability, and Pharmacodynamics of Construct 1 in Pediatric Subjects with MPS II (Hunter Syndrome)

6.2.1. Synopsis

Investigational Product, Dose, and Route of Administration

Construct 1: AAV9.CB7.hIDS (recombinant adeno-associated virus serotype 9 capsid containing human iduronate-2-sulfatase expression cassette). See paragraph [0019] and FIG. 5.

Product will be delivered as a single intracisternal (IC) dose.

Two dose levels will be evaluated, $1.3 \times 10^{10}$ genome copies (GC)/g brain mass (Dose 1) and $6.5 \times 10^{10}$ GC/g brain mass (Dose 2). Total dose administered will account for estimated brain size of study subjects based on their age. Total volume of product administered will not exceed 5 mL.

Objectives

Primary Objective:

To evaluate the safety and tolerability of Construct 1 through 24 weeks following a single IC dose administered to pediatric subjects who have severe MPS II Secondary Objectives:

To evaluate the long-term safety and tolerability of Construct 1

To evaluate the effect of Construct 1 on biomarkers in cerebrospinal fluid (CSF), plasma, and urine To evaluate the effect of Construct 1 on neurodevelopmental parameters of cognitive, behavioral, and adaptive function To evaluate vector shedding in CSF, plasma, and urine Exploratory Objectives:

To evaluate immunogenicity of Construct 1

To explore the effect of Construct 1 on physical changes to the CNS

To explore the effect of Construct 1 on systemic manifestations of disease

To explore the effect of Construct 1 on auditory capacity

To explore the effect of Construct 1 on biomarkers in plasma and urine in subjects who temporarily discontinue IV ERT (ELAPRASE®)

To explore the effect of Construct 1 on quality of life (QOL) and sleep measures.

Study Design and Methodology

This is a Phase I/II, first-in-human, multicenter, open-label, single arm dose escalation study of Construct 1. No control group is included. Approximately 6 pediatric subjects who have severe MPS II could be enrolled into 2 dose cohorts, $1.3 \times 10^{10}$ GC/g brain mass (Dose 1) or $6.5 \times 10^{10}$ GC/g brain mass (Dose 2) and will receive a single dose of Construct 1 administered by IC injection. Safety will be the primary focus for the initial 24 weeks after treatment (primary study period). Following completion of the primary study period, subjects will continue to be assessed (safety and efficacy) for up to a total of 104 weeks following treatment with Construct 1. At the end of the study, subjects will be invited to participate in a long-term follow-up study.

The first 3 eligible subjects will be enrolled into the Dose 1 cohort ($1.3 \times 10^{10}$ GC/g brain mass). After Construct 1 administration to the first subject, there will be an 8-week observation period for safety. The Internal Safety Committee (ISC) will review the safety data obtained during the first 8 weeks (including data obtained during the Week 8 visit) for this subject, and if there are no safety concerns, the $2^{nd}$ subject may be enrolled. The same process will be used to enroll the $3^{rd}$ subject. If no safety review trigger (SRT) event is observed, all available safety data for the Dose 1 cohort obtained up to and including the Week 8 visit for the $3^{rd}$ subject will be evaluated by the Independent Data Monitoring Committee (IDMC). If the decision is to proceed to the second dose ($6.5 \times 10^{10}$ GC/g brain mass), the subsequent 2 subjects will follow the same dosing scheme as the initial dose cohort with dosing of each subsequent subject occurring after all safety data obtained during the first 8 weeks (including data obtained during the Week 8 visit) for the last dosed subject have been reviewed. The ISC will review all subject safety data obtained up to and including the Week 2 visit of the $2^{nd}$ subject and may determine that it is safe to proceed with dosing of the $3^{rd}$ subject immediately after this assessment. All available safety data for the Dose 2 cohort will be evaluated by the IDMC after the Week 8 visit for the $3^{rd}$ subject in the Dose 2 cohort.

Potential subjects will be screened up to 35 days prior to dosing to determine eligibility for the study. Those subjects who meet the eligibility criteria will be admitted to the hospital between Day -2 and the morning of Day 1 (according to institutional practice), and baseline assessments will be performed pre-dose. Subjects will receive a single IC dose of Construct 1 on Day 1 and will remain in the hospital for approximately 30-36 hours after dosing for observation. Subsequent assessments in the primary study period (i.e., through Week 24) will be performed weekly through Week 4 and at Weeks 8, 12, 16, 20, and 24. After the primary study period, visits will be at Weeks 28, 32, 40, 48, 52, 56, 64, 78, and 104. The Week 12, 40, and 64 visits may be performed by a home health nurse. The Week 20 and 28 assessments will be limited to evaluation of AEs and concomitant therapies by telephone contact.

All subjects will initially receive immune suppression (IS) in the study based on findings of potential immunogenicity in the nonclinical safety/toxicology study conducted in animals and will include corticosteroids (methylprednisolone 10 mg/kg intravenously [IV] once on Day 1 predose and oral prednisone starting at 0.5 mg/kg/day on Day 2 with gradual tapering and discontinuation by Week 12), tacrolimus (1 mg twice daily [BID] by mouth [PO] Day 2 to Week 24 with target blood level of 4-8 ng/mL and tapering over 8 weeks between Week 24 and 32) and sirolimus (a loading dose of 1 mg/m$^2$ every 4 hours×3 doses on Day -2 and then from Day -1: sirolimus 0.5 mg/m$^2$/day divided in BID dosing with target blood level of 4-8 ng/ml until Week 48). Neurologic assessments and tacrolimus/sirolimus blood level monitoring will be conducted as per Table 3. The doses of sirolimus and tacrolimus will be adjusted to maintain blood levels in the target range.

No IS therapy is planned after Week 48. If IS is required after Week 48 to control a clinically-relevant immune response, the appropriate immunosuppressive regimen will be determined by the principal investigator (PI), in discussion with the Medical Monitor and Sponsor, as clinically indicated.

Efficacy assessments will include neurocognitive function, auditory capacity, brain MRI, liver and spleen size, and measurements of levels of pharmacodynamic (PD) biomarkers in CSF, plasma, and urine. Neurocognitive or adaptive scales performed as part of subjects' standard of care while participating in the trial may also be collected, as determined by the study sponsor after discussing with the site.

Endpoints

Primary Endpoints:

Safety through Week 24: AEs and serious adverse events (SAEs)

Secondary Endpoints:

Safety through Week 104: AE reporting, laboratory evaluations, vital signs, ECGs, physical examinations, and neurologic assessments Biomarkers in CSF (GAGs, I2S activity), plasma (GAGs, I2S activity), and urine (GAGs)

Neurodevelopmental parameters of cognitive, behavioral, and adaptive function:

Bayley Scales of Infant and Toddler Development, $3^{rd}$ Edition (BSID-III) (Bayley, 2005) or Kaufman Assessment Battery for Children, $2^{nd}$ Edition (KABC-II) (Kaufman, 2004)

Vineland Adaptive Behavior Scales, 2nd Edition, Comprehensive Interview Form (VABS-II) (Sparrow et al., 2005)

Vector concentration in CSF, plasma, and urine by quantitative polymerase chain reaction (PCR) to Construct 1 deoxyribonucleic acid (DNA)

Exploratory Endpoints:

Immunogenicity measurements

Neutralizing antibody titers to AAV9 and binding antibody titers to I2S in CSF and serum Enzyme-linked immunospot (ELISPOT) assay: T-cell response to AAV9 and I2S Flow cytometry: AAV- and I2S-specific regulatory T cells CNS structural abnormalities assessed by magnetic resonance imaging (MM) of the brain Liver and spleen size assessed by MM and ultrasound of the abdomen Auditory capacity changes measured by auditory brainstem response (ABR) testing Plasma and urinary GAGs in subjects who temporarily discontinue IV ERT (ELAPRASE®)

PedsQL (Version 4)

Global impression of sleep scale

The total duration of the study may be 104 weeks post-dose with a primary safety evaluation time point of 24 weeks. Screening may take up to 35 days.

Diagnosis and Criteria for Inclusion and Exclusion

To be eligible to participate in this study, a subject must meet all the following inclusion criteria:

1. The subject's legal guardian(s) is(are) willing and able to provide written, signed informed consent after the nature of the study has been explained, and prior to any research-related procedures.
2. Is a male
3. Meets one of the following criteria:
  a. Has a documented diagnosis of MPS II AND is ≥4 months to <5 years of age AND a has a neurocognitive testing score >55 and ≤77 (BSID-III or KABC-II), OR
  b. Has a documented diagnosis of MPS II AND is ≥4 months and <5 years of age AND has a decline of ≥1 standard deviation on sequential neurocognitive testing (BSID-III or KABC-II) and a testing score >55, OR
  c. Has a relative diagnosed with severe MPS II who has the same IDS mutation as the subject AND in the opinion of a geneticist has inherited a severe form of MPS II
4. Has sufficient auditory and visual capacity, with or without aids, to complete the required protocol testing, and be compliant with wearing the aid, if applicable, on testing days Subjects who meet any of the following exclusion criteria will not be eligible to participate in the study:

1. Has a contraindication for an IC injection, including any of the following:
  a. Review of baseline MRI testing by the team of neuroradiologists/neurosurgeons participating in study (1 per site) shows a contraindication for an IC injection
  b. History of prior head/neck surgery, which resulted in a contraindication to IC injection, based on review of available information by the team of neuroradiologists/neurosurgeons participating in study
  c. Has any contraindication to computed tomography (CT), contrast agent, or to general anesthesia
  d. Has any contraindication to MRI or gadolinium
  e. Has estimated glomerular filtration rate (eGFR)<30 mL/min/1.73 $m^2$
2. Has any condition that would contraindicate treatment with prednisone, tacrolimus or sirolimus
3. Has any neurocognitive deficit not attributable to MPS II or diagnosis of a neuropsychiatric condition that may in the opinion of the PI confound interpretation of study results
4. Has any contraindication to lumbar puncture
5. Has a ventricular shunt
6. Has undergone hematopoietic stem cell transplantation (HSCT)
7. Has had prior treatment with an AAV-based gene therapy product
8. Has received idursulfase [ELAPRASE®] via intrathecal (IT) administration
9. Has received idursulfase [ELAPRASE®] IV and experienced a serious hypersensitivity reaction, including anaphylaxis, deemed related to IV idursulfase [ELAPRASE®] administration.
10. Has received any investigational product within 30 days of Day 1 or 5 half-lives before signing of the Informed Consent Form (ICF), whichever is longer
11. Has any history of lymphoma or history of another cancer, other than squamous cell or basal cell carcinoma of the skin, that has not been in full remission for at least 3 months before screening
12. Has a platelet count <100,000 per microliter (μL)
13. Has aminotransferase (ALT) or aspartate aminotransferase (AST) >3×ULN or total bilirubin >1.5×ULN at screening unless the subject has a previously known history of Gilbert's syndrome and a fractionated bilirubin that shows conjugated bilirubin <35% of total bilirubin
14. Uncontrolled hypertension (systolic blood pressure [BP]>180 mmHg, diastolic BP >100 mmHg) despite maximal medical treatment
15. Has a history of human immunodeficiency virus (HIV) or hepatitis B or hepatitis C virus infection, or positive screening tests for hepatitis B surface antigen or hepatitis B core antibody, or hepatitis C or HIV antibodies
16. Is a first-degree family member of a clinical site employee or any other individual involved with the conduct of the study or is a clinical site employee or other individual involved with the conduct of the study
17. Has a clinically significant ECG abnormality that, in the opinion of the PI, would compromise the subject's safety
18. Has a serious or unstable medical or psychological condition that, in the opinion of the PI, would compromise the subject's safety or successful participation in the study or interpretation of study results 19. Has uncontrolled seizures that in opinion of the PI would put the subject at undue risk Exclusion Criteria Related to Immunosuppressive Therapy:

20. Has a history of a hypersensitivity reaction to tacrolimus, sirolimus, or prednisone
21. Has a history of a primary immunodeficiency (e.g., common variable immunodeficiency syndrome), splenectomy, or any underlying condition that predisposes the subject to infection
22. Has herpes zoster (VZV), cytomegalovirus (CMV), or Epstein-Barr virus (EBV) infection that has not completely resolved at least 12 weeks prior to screening
23. Has any infection requiring hospitalization or treatment with parenteral anti-infectives not resolved at least 8 weeks prior to Visit 2
24. Has any active infection requiring oral anti-infectives (including antivirals) within 10 days prior to Visit 2
25. Has a history of active tuberculosis (TB) or a positive Quantiferon-TB Gold test during screening
26. Has any live vaccine within 8 weeks prior to signing the ICF
27. Had major surgery within 8 weeks before signing the ICF or major surgery planned during the study period
28. Anticipate the need for adenoidectomy or tonsillectomy within 6 months of enrollment
29. Has an absolute neutrophil count <1.3×10$^3$/μL
30. Has any condition or laboratory abnormality that the PI believes would not be appropriate for immunosuppressive therapy Statistical Methods All data will be presented in subject data listings. Categorical variables will be summarized using frequencies and percentages, and continuous variables will be summarized using descriptive statistics (n, mean, standard deviation, median, minimum, and maximum). Graphical displays will be presented as appropriate. Safety and PD endpoints will be reported by dose group and may also be reported for the 2 dose groups combined.

Sample Size and Power Calculation: No formal calculation was performed to determine sample size.

6.2.2. Abbreviations and Terms

| Abbreviation | Term |
| --- | --- |
| AAV | Adeno-associated virus |
| AAV9 | AAV vector of serotype 9 |
| AE(s) | Adverse event(s) |
| ALP | Alkaline phosphatase |
| ALT | Alanine aminotransferase |
| AST | Aspartate aminotransferase |
| BBB | Blood-brain barrier |
| BID | Twice a day |
| BP | Blood pressure |
| BSID | Bayley Scales of Infant and Toddler Development |
| BSL | Biosafety level |
| CB7 | Hybrid C4 and CB (chicken beta actin promoter) |
| CBC | Complete blood count |
| cDNA | Consensus DNA |
| CFR | Code of Federal Regulations |
| CI | Confidence interval |
| CMV | Cytomegalovirus |
| CNS | Central nervous system |
| CoA | Certificate of analysis |
| CRF | Case Report Form |
| CSF | Cerebrospinal fluid |
| CT | Computed tomography |
| CTA | Clinical Trial Agreement |
| CTCAE | Common Terminology Criteria for Adverse Events |
| CZ | Crystal Zenith ® |
| DLT(s) | Dose-limiting toxicity(ies) |
| DNA | Deoxyribonucleic acid |
| DRG | Dorsal root ganglia |
| EBV | Epstein-Barr virus |
| ECG | Electrocardiogram |
| EDC | Electronic Data Capture |
| eGFR | Estimated glomerular filtration rate |
| ELISA | Enzyme-Linked Immunosorbent Assay |
| ELISPOT | Enzyme-linked immunospot |
| EOS | End of Study |
| ERT | Enzyme replacement therapy |
| ET | Early Termination |
| FDA | US Food and Drug Administration |
| GAG(s) | Glycosaminoglycan(s) |
| GAN | Giant Axonal Neuropathy |
| GC | Genome copies |
| GCP | Good Clinical Practice |
| GLP | Good Laboratory Practice |
| GM3 | Monosialodihexosylganglioside |
| HDL | High-density lipoprotein |
| Hep | hepatitis |
| Hex | Hexosaminidase |
| hIDS | Human iduronate-2-sulfatase |
| HIPAA | Health Insurance Portability and Accounting Act |
| HIV | Human immunodeficiency virus |
| HSCT | Hematopoietic stem cell transplantation |
| I2S | Iduronate-2-sulfatase |
| IB | Investigator's Brochure |
| IC | Intracisternal(ly) |
| ICF | Informed Consent Form |
| ICH | International Council for Harmonisation |
| ICV | Intracerebroventricular |
| IDMC | Independent Data Monitoring Committee |
| IDS | Iduronate-2-sulfatase gene |
| IEC(s) | Independent Ethics Committee(s) |
| IgG | Immunoglobulin G |
| IND | Investigation New Drug |
| IP | Investigational product |
| IQ | Intelligence quotient |
| IRB | Institutional Review Board |
| IS | immune suppression/immunosuppression |
| IT | Intrathecal(ly) |
| ITR(s) | Inverted terminal repeat(s) |
| IV | Intravenous(ly) |
| KABC | Kaufman Assessment Battery for Children |
| KIDS | Kinder Infant Development Scale |
| KSPD | Kyoto Scale of Psychological Development |
| LDL | Low-density lipoprotein |
| LIMP2 | Lysosomal membrane protein |
| MED | Minimum effective dose |
| MedDRA | Medical Dictionary of Regulatory Activities |
| MMF | Mycophenolate mofetil |
| MPS I | Mucopolysaccharidosis type I |
| MPS II | Mucopolysaccharidosis type II |
| MPS III | Sanfilippo syndrome |
| MPS VII | Mucopolysaccharidosis type VII |
| MRI | Magnetic resonance imaging |
| MTD | Maximum tolerated dose |
| mTORC1 | Mammalian/mechanistic target of rapamycin complex 1 |
| N | Number in sample |
| NAB | Neutralizing antibody |
| NCI | National Cancer Institute |
| NHP(s) | Non-human primate(s) |
| NIH | National Institutes of Health |
| NOAEL | No-observable-adverse-effect level |
| PBMC(s) | Peripheral blood mononuclear cell(s) |
| PCR | Polymerase chain reaction |
| PD | Pharmacodynamic(s) |
| PgP | P-glycoprotein |
| PI | Principal Investigator |
| PML | Progressive multifocal leukoencephalopathy |
| PO | By mouth/orally |

| Abbreviation | Term |
| --- | --- |
| PT | Prothrombin time or Preferred Term |
| PTT | Partial thromboplastin time |
| PVAN | Polyoma virus-associated nephropathy |
| QD | Daily |
| qPCR | Quantitative polymerase chain reaction |
| RBC | Red blood cell |
| RG1 | Risk Group 1 |
| Construct 1 | Recombinant adeno-associated virus serotype 9 capsid containing human iduronate-2-sulfatase expression cassette |
| SAE(s) | Serious adverse event(s) |
| SAP | Statistical analysis plan |
| SDV | Source document verification |
| SMA | Spinal Muscular Atrophy |
| SOC | System Organ Class |
| SRT | Safety review trigger |
| TB | Tuberculosis |
| TEAE(s) | Treatment-emergent adverse event(s) |
| Treg | Regulatory T cell |
| ULN | Upper limit of normal |
| U.S. | United States |
| US | Ultrasound |
| USMs | Urgent safety measures |
| VZV | Varicella zoster virus |
| WBC | White blood cell (count) |
| WHO | World Health Organization |

6.2.3. Investigational Plan

Endpoints
Primary Endpoints
Safety through Week 24: AEs and SAEs
Secondary Endpoints
Safety through Week 104: AE reporting, laboratory evaluations, vital signs, electrocardiograms (ECGs), physical examinations, and neurologic assessments
Biomarkers in CSF (GAGs, I2S activity), plasma (GAGs, I2S activity), and urine (GAGs)
Neurodevelopmental parameters of cognitive, behavioral, and adaptive function:
  Bayley Scales of Infant and Toddler Development, 3rd Edition (BSID-III) (Bayley, 2005) or Kaufman Assessment Battery for Children, 2nd Edition (KABC-II) (Kaufman, 2004)
  Vineland Adaptive Behavior Scales, 2nd Edition, Comprehensive Interview Form (VABS-II) (Sparrow et al., 2005)
Vector concentration in CSF, plasma, and urine by quantitative polymerase chain reaction (PCR) to Construct 1 DNA
Exploratory Endpoints
Immunogenicity measurements
  Neutralizing antibody titers to AAV9 and binding antibody titers to I2S in CSF and serum
  Enzyme-linked immunospot (ELISPOT) assay: T-cell response to AAV9 and I2S
  Flow cytometry: AAV- and I2S-specific regulatory T cells
CNS structural abnormalities assessed by MRI of the brain
Liver and spleen size assessed by MRI of the abdomen
Auditory capacity changes measured by auditory brainstem response (ABR) testing
Plasma and urinary GAGss in subjects who temporarily discontinue IV ERT (ELAPRASE®)
PedsQL (Version 4)
Global impression of sleep scale
Study Design This is a Phase I/II, first-in-human, multicenter, open-label, single arm dose escalation study of Construct 1. Approximately 6 pediatric subjects with severe MPS II could be enrolled into 2 dose cohorts, $1.3 \times 10^{10}$ GC/g brain mass (Dose 1) or $6.5 \times 10^{10}$ GC/g brain mass (Dose 2), and will receive a single dose of Construct 1 administered by IC injection. Safety will be the primary focus for the initial 24 weeks after treatment (primary study period). Following completion of the primary study period, subjects will continue to be assessed (safety and efficacy) for up to a total of 104 weeks following treatment with Construct 1. At the end of the study, all subjects will be invited to participate in a long-term follow-up study.

Potential subjects will be screened up to 35 days prior to dosing to determine eligibility for the study. Those subjects who meet the eligibility criteria will be admitted to the hospital between Day −2 and the morning of Day 1 (according to institutional practice), and baseline assessments will be performed pre-dose. Subjects will receive a single IC dose of Construct 1 on Day 1 and will remain in the hospital for approximately 30 to 36 hours after dosing for observation. Subsequent assessments in the primary study period (i.e., through Week 24) will be performed weekly through Week 4 and at Weeks 8, 12, 16, 20, and 24. After the primary study period, visits will be at Weeks 28, 32, 40, 48, 52, 56, 64, 78, and 104. The Week 12, 40, and 64 visits may be performed by a home health nurse. The Week 20 and 28 assessments will be limited to evaluation of AEs and concomitant therapies by telephone contact.

All subjects will initially receive IS in the study based on findings in the nonclinical studies. IS therapy will include corticosteroids (methylprednisolone 10 mg/kg IV once on Day 1 predose and oral prednisone starting at 0.5 mg/kg/day on Day 2 with gradual tapering and discontinuation by Week 12), tacrolimus (1 mg twice daily [BID] by mouth [PO] Day 2 to Week 24 with target blood level of 4-8 ng/mL and tapering over 8 weeks between Week 24 and 32), and sirolimus (a loading dose of 1 mg/m² every 4 hours×3 doses on Day −2 and then from Day −1: sirolimus 0.5 mg/m²/day divided in twice a day dosing with target blood level of 4-8 ng/ml until Week 48). Neurologic assessments and tacrolimus/sirolimus blood level monitoring will be conducted as per Table 3. The doses of sirolimus and tacrolimus will be adjusted to maintain blood levels in the target range.

No IS therapy is planned after Week 48. If IS is required after Week 48 to control a clinically relevant immune response, the appropriate immunosuppressive regimen will be determined by the principal investigator (PI), in discussion with the Medical Monitor and Sponsor, as clinically indicated.

The safety and tolerability of Construct 1 will be monitored through assessment of AEs and serious adverse events (SAEs), chemistry, hematology, urinalysis, markers of CSF inflammation, immunogenicity, vector shedding (vector concentration), vital signs, electrocardiograms (ECGs), and physical examinations including neurological assessments.

Efficacy assessments will include neurocognitive and adaptive function, auditory capacity, brain MRI, liver and spleen size, measurements of levels of PD biomarkers in CSF, plasma, and urine.

6.2.4. Subject Population and Selection

Selection of Study Population

Approximately 6 pediatric subjects ages ≥4 months to <5 years who have documented neurocognitive deficits due to MPS II or who have a genotype and family history consistent with an inherited form of severe MPS II will be treated with investigational product (IP).

Inclusion Criteria

To be eligible to participate in this study, a subject must meet all the following criteria:

1. The subject's legal guardian is (are) willing and able to provide written, signed informed consent after the nature of the study has been explained, and prior to any research-related procedures.
2. Is a male
3. Meets one of the following criteria:
    a. Has a documented diagnosis of MPS II AND is ≥4 months to <5 years of age AND a has a neurocognitive testing score >55 and ≤77 (BSID-III or KABC-II), OR
    b. Has a documented diagnosis of MPS II AND is ≥4 months and <5 years of age AND has a decline of ≥1 standard deviation on sequential neurocognitive testing (BSID-III or KABC-II) and a testing score >55, OR
    c. Has relative diagnosed with severe MPS II carrying the same IDS mutation as the subject AND in the opinion of a geneticist has inherited a severe form of MPS II
4. Has sufficient auditory and visual capacity, with or without aids, to complete the required protocol testing, and be compliant with wearing the aid, if applicable, on testing days.

Exclusion Criteria

A subject who meets any of the following exclusion criteria will not be eligible to participate in the study:

1. Has a contraindication for an IC injection, including any of the following:
    a. Review of baseline MRI testing by the team of neuroradiologists/neurosurgeons participating in study (1 per site) shows a contraindication for an IC injection
    b. History of prior head/neck surgery, which resulted in a contraindication to IC injection, based on review of available information by the team of neuroradiologists/neurosurgeons participating in study
    c. Has any contraindication to computed tomography (CT), contrast agent or general anesthesia
    d. Has any contraindication to MRI or gadolinium
    e. Has estimated glomerular filtration rate (eGFR)<30 mL/min/1.73 m$^2$
2. Has any condition that would contraindicate treatment with prednisone, tacrolimus, or sirolimus.
3. Has any neurocognitive deficit not attributable to MPS II or diagnosis of a neuropsychiatric condition that may in the opinion of the PI confound interpretation of study results.
4. Has any contraindication to lumbar puncture
5. Has a ventricular shunt
6. Has undergone hematopoietic stem cell transplantation (HSCT).
7. Has had prior treatment with an AAV-based gene therapy product.
8. Has received idursulfase via intrathecal (IT) administration
9. Has received IV idursulfase [ELAPRASE®] and experienced a serious hypersensitivity reaction, including anaphylaxis, deemed related to IV idursulfase [ELAPRASE®] administration.
10. Has received any investigational product within 30 days of Day 1 or 5 half-lives before signing of the Informed Consent Form (ICF), whichever is longer
11. Has any history of lymphoma or history of another cancer, other than squamous cell or basal cell carcinoma of the skin, that has not been in full remission for at least 3 months before screening.
12. Platelet count <100,000 per microliter (µL)
13. Has aminotransferase (ALT) or aspartate aminotransferase (AST) >3×ULN or total bilirubin >1.5×ULN at screening unless the subject has a previously known history of Gilbert's syndrome and a fractionated bilirubin that shows conjugated bilirubin <35% of total bilirubin.
14. Uncontrolled hypertension (systolic blood pressure [BP]>180 mmHg, diastolic BP >100 mmHg) despite maximal medical treatment.
15. Has a history of human immunodeficiency virus (HIV) or hepatitis B or hepatitis C virus infection, or positive screening tests for hepatitis B surface antigen or hepatitis B core antibody, or hepatitis C or HIV antibodies.
16. Is a first-degree family member of a clinical site employee or any other individual involved with the conduct of the study or is a clinical site employee or other individual involved with the conduct of the study.
17. Has a clinically significant ECG abnormality that, in the opinion of the PI, would compromise the subject's safety.
18. Has a serious or unstable medical or psychological condition that, in the opinion of the PI, would compromise the subject's safety or successful participation in the study or interpretation of study results.
19. Has uncontrolled seizures that in opinion of the PI would put the subject at undue risk.

Exclusion Criteria Related to Immunosuppressive Therapy:

20. A history of a hypersensitivity reaction to tacrolimus, sirolimus, or prednisone
21. A history of a primary immunodeficiency (e.g., common variable immunodeficiency syndrome), splenectomy, or any underlying condition that predisposes the subject to infection
22. Herpes zoster (VZV), cytomegalovirus (CMV), or Epstein-Barr virus (EBV) infection that has not completely resolved at least 12 weeks prior to screening
23. Any infection requiring hospitalization or treatment with parenteral anti-infectives not resolved at least 8 weeks prior to Visit 2
24. Any active infection requiring oral anti-infectives (including antivirals) within 10 days prior to Visit 2
25. History of active tuberculosis (TB) or a positive Quantiferon-TB Gold test during screening
26. Any live vaccine within 8 weeks prior to signing the ICF
27. Major surgery within 8 weeks before signing the ICF or major surgery planned during the study period
28. Anticipate the need for adenoidectomy or tonsillectomy within 6 months of enrollment
29. Absolute neutrophil count <1.3×10$^3$/µL
30. Any condition or laboratory abnormality that the PI believes would not be appropriate for immunosuppressive therapy

6.2.5. Treatments

Treatments Administered

The investigational product (IP), Construct 1 (see FIG. 5), will be given as a single dose IC administration. Two dose levels: $1.3 \times 10^{10}$ GC/g brain mass (Dose 1) or $6.5 \times 10^{10}$ GC/g brain mass (Dose 2). Total dose administered (total GC) will be adjusted to account for differences in brain size by age. Total volume of product administered will not exceed 5 mL.

No reference therapy will be administered during this study. IS therapy will be given in addition to IP, as described below.

Investigational Product

Construct 1 is a non-replicating recombinant AAV of serotype 9 capsid containing an hIDS expression cassette. See paragraph [0019].

| | |
|---|---|
| Product | Construct 1 |
| Gene | hIDS |
| Control Elements: | CB7 promoter, chicken beta actin intron, rabbit beta-globin polyadenylation signal |
| AAV | 9 |

AAV = adeno-associated virus;
CB = chicken beta-actin;
hIDS = human iduronate-2-sulfatase Construct 1 is a non-replicating recombinant AAV9 vector that allows for efficient expression of the human iduronate-2-sulfatase (hIDS) product in the central nervous system (CNS) following intrathecal (IT) administration. The vector genome contains an hIDS expression cassette flanked by AAV2 inverted terminal repeats (ITRs). Expression from the cassette is driven by a CB7 promoter, a hybrid between a cytomegalovirus (CMV) immediate-early enhancer and the chicken β-actin promoter. Transcription from this promoter is enhanced by the presence of the chicken β-actin intron (CI). The polyadenylation signal for the expression cassette is from the rabbit β-globin (RBG) gene. A schematic representation of Construct 1 is illustrated in FIG. 5.

The final IP is supplied as a frozen solution of the AAV vector active ingredient (AAV9.CB7.hIDS) in modified Elliotts B° solution with 0.001% Pluronic® F68, filled into 2-mL in CRYSTAL ZENITH® (CZ) vials, and sealed with a latex-free rubber stopper and aluminum flip-off seal. Vials should be stored at ≤−60° C. The concentration (in GC/mL) of each IP lot will be reported in the Certificate of Analysis (CoA). Detailed dosing instructions, based on the product concentration, will be provided in the Administration Manual.

Immunosuppressive Therapy

Corticosteroids

In the morning of vector administration (Day 1 predose), subjects will receive methylprednisolone 10 mg/kg IV (maximum of 500 mg) over at least 30 minutes. The methylprednisolone should be administered before the lumbar puncture and IC injection of IP. Premedication with acetaminophen and an antihistamine is optional and at the discretion of the investigator.

On Day 2, oral prednisone will be started with the goal to discontinue prednisone by Week 12. The dose of prednisone will be as follows:

Day 2 to the end of Week 2: 0.5 mg/kg/day

Week 3 and 4: 0.35 mg/kg/day

Week 5-8: 0.2 mg/kg/day

Week 9-12: 0.1 mg/kg

Prednisone will be discontinued after Week 12. The exact dose of prednisone can be adjusted to the next higher clinically practical dose.

Sirolimus 2 days prior to vector administration (Day −2): a loading dose of sirolimus 1 mg/m² every 4 hours×3 doses will be administered From Day −1: sirolimus 0.5 mg/m²/day divided in twice a day dosing with target blood level of 4-8 ng/ml Sirolimus will be discontinued after the Week 48 visit.

Tacrolimus

Tacrolimus will be started on Day 2 (the day following IP administration) at a dose of 1 mg twice daily and adjusted to achieve a blood level 4-8 ng/mL for 24 Weeks.

Starting at Week 24 visit, tacrolimus will be tapered off over 8 weeks. At Week 24 the dose will be decreased by approximately 50%. At Week 28 the dose will be further decreased by approximately 50%. Tacrolimus will be discontinued at Week 32.

Tacrolimus and sirolimus blood level monitoring will be conducted as per Table 3. Dosing adjustments are discussed in paragraphs [00220]-[00222].

Method of Assigning Subjects to Treatment

Eligible subjects will be enrolled and assigned sequentially to a dose cohort with the initial 3 subjects assigned to get $1.3 \times 10^{10}$ GC/g brain mass; the subsequent 3 subjects will be assigned to get $6.5 \times 10^{10}$ GC/g brain mass pending review of safety data by the IDMC.

Dosing Considerations

Investigational Product

Refer to paragraphs [00175] to [00186] for a description of the plan to sequentially dose subjects, including review of safety data between individual subjects and after each cohort has been dosed at any dose level.

Immunosuppressive Therapy

Prednisone dosing will start at 0.5 mg/kg/day and will be gradually tapered off by the Week 12 visit.

Tacrolimus dose adjustments will be made to maintain whole blood trough concentrations within 4 to 8 ng/mL for the first 24 Weeks. At Week 24 the dose will be decreased by approximately 50%. At Week 28 the dose will be further decreased by approximately 50%. Tacrolimus will be discontinued at Week 32. Sirolimus dose adjustments will be made to maintain whole blood trough concentrations within 4 to 8 ng/mL. In most subjects, dose adjustments can be based on the equation: new dose=current dose×(target concentration/current concentration). Subjects should continue on the new maintenance dose for at least 7 to 14 days before further dosage adjustment with concentration monitoring.

The following medications and procedures are prohibited:

No IT ERT is allowed within 6 months of screening.

Any investigational product within the 30 days or 5 half-lives, whichever is longer, prior to signing the ICF or at any time during the study (through Week 104)

Live vaccines should be avoided while on sirolimus and/or tacrolimus

Strong inhibitors of CYP3A4 and/or P-glycoprotein (PgP) (such as ketoconazole, voriconazole, itraconazole, posaconazole, erythromycin, telithromycin or clarithromycin) or strong inducers of CYP3A4 and or Pgp (such as rifampin or rifabutin) should be avoided while on sirolimus and/or tacrolimus Grapefruit juice inhibits CYP3A-enzymes resulting in increased tacrolimus and sirolimus whole blood trough concentrations. Subjects should avoid eating grapefruit or drinking grapefruit juice with tacrolimus and/or sirolimus.

Permitted Medications and Procedures

Subjects will be permitted to remain on a stable regimen of IV ERT as well as any supportive measures (e.g., physical therapy). According to local hospital standard of care, subjects will be permitted to receive medication to prevent claustrophobia during MM and receive general anesthesia for lumbar puncture, MM, and neuroconduction studies (ABRs or sensory evoked potentials).

Medications other than that described above, which are considered necessary for the subject's safety and wellbeing (e.g., for hypertension), may be given at the discretion of the Investigator in accordance with local standard of care and recorded in the appropriate sections of the CRF.

EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

What is claimed is:

1. A method for treating a human subject diagnosed with mucopolysaccharidosis type II (MPS II), comprising delivering to the cerebrospinal fluid (CSF) of the brain of the human subject a therapeutically effective amount of a glycosylated recombinant human iduronate-2-sulfatase (IDS) precursor produced by the human subject's neuronal or human glial cells transduced with a recombinant adeno-associated virus (AAV) vector carrying an expression cassette encoding the IDS precursor, by a single dose administration of the recombinant AAV vector via intracisternal (IC) injection or intracerebroventricular (ICV) injection to the human subject.

2. The method of claim 1, wherein the glycosylated recombinant human IDS precursor, is about 90 kDa as measured by polyacrylamide gel electrophoresis.

3. The method of claim 1, wherein the recombinant AAV comprises an AAV9 capsid protein.

4. The method of claim 1, wherein the recombinant AAV comprises an AAVrh10 capsid protein.

5. The method of claim 1, wherein the recombinant AAV comprises a recombinant AAV capsid protein.

6. The method of claim 1, wherein the single dose is from about $1.1 \times 10^{10}$ genome copies (GC)/g brain mass to about $6.5 \times 10^{10}$ GC/g brain mass.

7. The method of claim 1, wherein the single dose is from about $7.8 \times 10^{12}$ GC to about $8.5 \times 10^{13}$ GC.

8. The method of claim 1, wherein the single dose is $1.3 \times 10^{10}$ GC/g brain mass.

9. The method of claim 1, wherein the single dose is $6.5 \times 10^{10}$ GC/g brain mass.

10. The method of claim 1, wherein the human subject is 10 years old or younger.

11. The method of claim 1, wherein the human subject is between about 4 months old to about or less than about 5 years old.

12. The method of claim 1, wherein the human subject is about or at most about 18 months old.

13. The method of claim 1, wherein the human subject is about or at least about 3 years old.

14. The method of claim 1, wherein the human subject is about 3 years old to about 8 years old.

15. The method of claim 1, wherein the human subject is a pediatric human subject.

16. The method of claim 1, wherein the expression cassette comprises a CB7 promoter.

* * * * *

SEQUENCE LISTING

```
<160> NUMBER OF SEQ ID NOS: 48

<210> SEQ ID NO 1
<211> LENGTH: 550
<212> TYPE: PRT
<213> ORGANISM: Homo sapiens
<220> FEATURE:
<223> OTHER INFORMATION: Human IDS amino acid sequence

<400> SEQUENCE: 1

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190
```

```
Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 2
<211> LENGTH: 24
<212> TYPE: PRT
<213> ORGANISM: Artificial Sequence
<220> FEATURE:
<223> OTHER INFORMATION: Oligodendrocyte-myelin glycoprotein (hOMG)
      signal peptide
```

```
<400> SEQUENCE: 2

Met Glu Tyr Gln Ile Leu Lys Met Ser Leu Cys Leu Phe Ile Leu Leu
1               5                   10                  15

Phe Leu Thr Pro Gly Ile Leu Cys
            20

<210> SEQ ID NO 3
<211> LENGTH: 31
<212> TYPE: PRT
<213> ORGANISM: Artificial Sequence
<220> FEATURE:
<223> OTHER INFORMATION: Cellular repressor of E1A-stimulated genes
      2(hCREG2) signal peptide

<400> SEQUENCE: 3

Met Ser Val Arg Arg Gly Arg Arg Pro Ala Arg Pro Gly Thr Arg Leu
1               5                   10                  15

Ser Trp Leu Leu Cys Cys Ser Ala Leu Leu Ser Pro Ala Ala Gly
            20                  25                  30

<210> SEQ ID NO 4
<211> LENGTH: 28
<212> TYPE: PRT
<213> ORGANISM: Artificial Sequence
<220> FEATURE:
<223> OTHER INFORMATION: V-set and transmembrane domain containing
      2B(hVSTM2B) signal peptide

<400> SEQUENCE: 4

Met Glu Gln Arg Asn Arg Leu Gly Ala Leu Gly Tyr Leu Pro Pro Leu
1               5                   10                  15

Leu Leu His Ala Leu Leu Leu Phe Val Ala Asp Ala
            20                  25

<210> SEQ ID NO 5
<211> LENGTH: 29
<212> TYPE: PRT
<213> ORGANISM: Artificial Sequence
<220> FEATURE:
<223> OTHER INFORMATION: Protocadherin alpha-1 (hPCADHA1) signal peptide

<400> SEQUENCE: 5

Met Val Phe Ser Arg Arg Gly Gly Leu Gly Ala Arg Asp Leu Leu Leu
1               5                   10                  15

Trp Leu Leu Leu Leu Ala Ala Trp Glu Val Gly Ser Gly
            20                  25

<210> SEQ ID NO 6
<211> LENGTH: 19
<212> TYPE: PRT
<213> ORGANISM: Artificial Sequence
<220> FEATURE:
<223> OTHER INFORMATION: FAM19A1 (TAFA1) signal peptide

<400> SEQUENCE: 6

Met Ala Met Val Ser Ala Met Ser Trp Val Leu Tyr Leu Trp Ile Ser
1               5                   10                  15

Ala Cys Ala

<210> SEQ ID NO 7
<211> LENGTH: 26
<212> TYPE: PRT
<213> ORGANISM: Artificial Sequence
<220> FEATURE:
```

<223> OTHER INFORMATION: VEGF-A signal peptide

<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala
            20                  25

<210> SEQ ID NO 8
<211> LENGTH: 29
<212> TYPE: PRT
<213> ORGANISM: Artificial Sequence
<220> FEATURE:
<223> OTHER INFORMATION: Fibulin-1 signal peptide

<400> SEQUENCE: 8

Met Glu Arg Ala Ala Pro Ser Arg Arg Val Pro Leu Pro Leu Leu Leu
1               5                   10                  15

Leu Gly Gly Leu Ala Leu Leu Ala Ala Gly Val Asp Ala
            20                  25

<210> SEQ ID NO 9
<211> LENGTH: 19
<212> TYPE: PRT
<213> ORGANISM: Artificial Sequence
<220> FEATURE:
<223> OTHER INFORMATION: Vitronectin signal peptide

<400> SEQUENCE: 9

Met Ala Pro Leu Arg Pro Leu Leu Ile Leu Ala Leu Leu Ala Trp Val
1               5                   10                  15

Ala Leu Ala

<210> SEQ ID NO 10
<211> LENGTH: 18
<212> TYPE: PRT
<213> ORGANISM: Artificial Sequence
<220> FEATURE:
<223> OTHER INFORMATION: Complement Factor H signal peptide

<400> SEQUENCE: 10

Met Arg Leu Leu Ala Lys Ile Ile Cys Leu Met Leu Trp Ala Ile Cys
1               5                   10                  15

Val Ala

<210> SEQ ID NO 11
<211> LENGTH: 19
<212> TYPE: PRT
<213> ORGANISM: Artificial Sequence
<220> FEATURE:
<223> OTHER INFORMATION: Opticin signal peptide

<400> SEQUENCE: 11

Met Arg Leu Leu Ala Phe Leu Ser Leu Leu Ala Leu Val Leu Gln Glu
1               5                   10                  15

Thr Gly Thr

<210> SEQ ID NO 12
<211> LENGTH: 18
<212> TYPE: PRT
<213> ORGANISM: Artificial Sequence
<220> FEATURE:
<223> OTHER INFORMATION: Albumin signal peptide

```
<400> SEQUENCE: 12

Met Lys Trp Val Thr Phe Ile Ser Leu Leu Phe Leu Phe Ser Ser Ala
1               5                   10                  15

Tyr Ser

<210> SEQ ID NO 13
<211> LENGTH: 18
<212> TYPE: PRT
<213> ORGANISM: Artificial Sequence
<220> FEATURE:
<223> OTHER INFORMATION: Chymotrypsinogen signal peptide

<400> SEQUENCE: 13

Met Ala Phe Leu Trp Leu Leu Ser Cys Trp Ala Leu Leu Gly Thr Thr
1               5                   10                  15

Phe Gly

<210> SEQ ID NO 14
<211> LENGTH: 20
<212> TYPE: PRT
<213> ORGANISM: Artificial Sequence
<220> FEATURE:
<223> OTHER INFORMATION: Interleukin-2 signal peptide

<400> SEQUENCE: 14

Met Tyr Arg Met Gln Leu Leu Ser Cys Ile Ala Leu Ile Leu Ala Leu
1               5                   10                  15

Val Thr Asn Ser
            20

<210> SEQ ID NO 15
<211> LENGTH: 15
<212> TYPE: PRT
<213> ORGANISM: Artificial Sequence
<220> FEATURE:
<223> OTHER INFORMATION: Trypsinogen-2 signal peptide

<400> SEQUENCE: 15

Met Asn Leu Leu Leu Ile Leu Thr Phe Val Ala Ala Ala Val Ala
1               5                   10                  15

<210> SEQ ID NO 16
<211> LENGTH: 736
<212> TYPE: PRT
<213> ORGANISM: Artificial Sequence
<220> FEATURE:
<223> OTHER INFORMATION: AAV1

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

-continued

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

-continued

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 17
<211> LENGTH: 735
<212> TYPE: PRT
<213> ORGANISM: Artificial Sequence
<220> FEATURE:
<223> OTHER INFORMATION: AAV2

<400> SEQUENCE: 17

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
        180                 185                 190

Ala Ala Pro Ser Gly Leu Gly Thr Asn Thr Met Ala Thr Gly Ser Gly
    195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560
```

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 18
<211> LENGTH: 736
<212> TYPE: PRT
<213> ORGANISM: Artificial Sequence
<220> FEATURE:
<223> OTHER INFORMATION: AAV3-3

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

```
Ala Ala Pro Thr Ser Leu Gly Ser Asn Thr Met Ala Ser Gly Gly
            195                 200                 205
Ala Pro Met Ala Asp Asn Asn Glu Gly Ala Asp Gly Val Gly Asn Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Phe Arg Pro Lys Lys Leu Ser Phe Lys Leu Phe Asn Ile Gln Val
305                 310                 315                 320
Arg Gly Val Thr Gln Asn Asp Gly Thr Thr Thr Ile Ala Asn Asn Leu
            325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
            405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
            435                 440                 445
Gln Gly Thr Thr Ser Gly Thr Thr Asn Gln Ser Arg Leu Leu Phe Ser
            450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
            485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
            515                 520                 525
Asp Asp Glu Glu Lys Phe Phe Pro Met His Gly Asn Leu Ile Phe Gly
            530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
            565                 570                 575
Tyr Gly Thr Val Ala Asn Asn Leu Gln Ser Ser Asn Thr Ala Pro Thr
            580                 585                 590
Thr Gly Thr Val Asn His Gln Gly Ala Leu Pro Gly Met Val Trp Gln
            595                 600                 605
```

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                    645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 19
<211> LENGTH: 734
<212> TYPE: PRT
<213> ORGANISM: Artificial Sequence
<220> FEATURE:
<223> OTHER INFORMATION: AAV4-4

<400> SEQUENCE: 19

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

```
Trp Val Leu Pro Thr Tyr Asn His Leu Tyr Lys Arg Leu Gly Glu
            245                 250                 255

Ser Leu Gln Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
    275                 280                 285

Arg Leu Ile Asn Asn Asn Trp Gly Met Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
    530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655
```

```
Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
        690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 20
<211> LENGTH: 724
<212> TYPE: PRT
<213> ORGANISM: Artificial Sequence
<220> FEATURE:
<223> OTHER INFORMATION: AAV5

<400> SEQUENCE: 20

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285
```

-continued

```
Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700
```

Ser Thr Gly Glu Tyr Arg Thr Thr Arg Pro Ile Gly Thr Arg Tyr Leu
705                 710                 715                 720

Thr Arg Pro Leu

<210> SEQ ID NO 21
<211> LENGTH: 736
<212> TYPE: PRT
<213> ORGANISM: Artificial Sequence
<220> FEATURE:
<223> OTHER INFORMATION: AAV6

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 22
<211> LENGTH: 737
<212> TYPE: PRT

<213> ORGANISM: Artificial Sequence
<220> FEATURE:
<223> OTHER INFORMATION: AAV7

<400> SEQUENCE: 22

```
Met Ala Ala Asp Gly Tyr Leu Pro Asp Trp Leu Glu Asp Asn Leu Ser
1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380
```

```
Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
        450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
            565                 570                 575

Glu Tyr Gly Ile Val Ser Ser Asn Leu Gln Ala Ala Asn Thr Ala Ala
        580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
        690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 23
<211> LENGTH: 738
<212> TYPE: PRT
<213> ORGANISM: Artificial Sequence
<220> FEATURE:
<223> OTHER INFORMATION: AAV8
```

<400> SEQUENCE: 23

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400
```

```
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                485                 490                 495
Gln Asn Asn Asn Ser Asn Phe Ala Trp Thr Ala Gly Thr Lys Tyr His
                500                 505                 510
Leu Asn Gly Arg Asn Ser Leu Ala Asn Pro Gly Ile Ala Met Ala Thr
        515                 520                 525
His Lys Asp Asp Glu Glu Arg Phe Phe Pro Ser Asn Gly Ile Leu Ile
    530                 535                 540
Phe Gly Lys Gln Asn Ala Ala Arg Asp Asn Ala Asp Tyr Ser Asp Val
545                 550                 555                 560
Met Leu Thr Ser Glu Glu Glu Ile Lys Thr Thr Asn Pro Val Ala Thr
                565                 570                 575
Glu Glu Tyr Gly Ile Val Ala Asp Asn Leu Gln Gln Gln Asn Thr Ala
            580                 585                 590
Pro Gln Ile Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
            660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
    690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 24
<211> LENGTH: 736
<212> TYPE: PRT
<213> ORGANISM: Artificial Sequence
<220> FEATURE:
<223> OTHER INFORMATION: hu31

<400> SEQUENCE: 24

Met Ala Ala Asp Gly Tyr Leu Pro Asp Trp Leu Glu Asp Thr Leu Ser
1               5                   10                  15
```

```
Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Gly Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

```
Asp Arg Leu Met Asn Pro Leu Ile Asp Gln Tyr Leu Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Ser Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 25
<211> LENGTH: 736
<212> TYPE: PRT
<213> ORGANISM: Artificial Sequence
<220> FEATURE:
<223> OTHER INFORMATION: hu32

<400> SEQUENCE: 25

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480
```

-continued

Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 26
<211> LENGTH: 736
<212> TYPE: PRT
<213> ORGANISM: Artificial Sequence
<220> FEATURE:
<223> OTHER INFORMATION: AAV9

<400> SEQUENCE: 26

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110

```
Asn Leu Gly Arg Ala Val Phe Gln Ala Lys Lys Arg Leu Glu Pro
            115                 120                 125
Leu Gly Leu Val Glu Glu Ala Ala Lys Thr Ala Pro Gly Lys Lys Arg
130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
            515                 520                 525
```

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 27
<211> LENGTH: 550
<212> TYPE: PRT
<213> ORGANISM: Homo sapiens
<220> FEATURE:
<223> OTHER INFORMATION: SP/P22304/IDS_human

<400> SEQUENCE: 27

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
             165                 170                 175

Glu Leu His Ala Asn Leu Leu Cys Pro Val Asp Val Leu Asp Val Pro
             180                 185                 190

Glu Gly Thr Leu Pro Asp Lys Gln Ser Thr Glu Gln Ala Ile Gln Leu
             195                 200                 205

Leu Glu Lys Met Lys Thr Ser Ala Ser Pro Phe Phe Leu Ala Val Gly
             210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
             245                 250                 255

Asp Gly Leu Pro Pro Val Ala Tyr Asn Pro Trp Met Asp Ile Arg Gln
             260                 265                 270

Arg Glu Asp Val Gln Ala Leu Asn Ile Ser Val Pro Tyr Gly Pro Ile
             275                 280                 285

Pro Val Asp Phe Gln Arg Lys Ile Arg Gln Ser Tyr Phe Ala Ser Val
             290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
             325                 330                 335

Trp Ala Leu Gly Glu His Gly Glu Trp Ala Lys Tyr Ser Asn Phe Asp
             340                 345                 350

Val Ala Thr His Val Pro Leu Ile Phe Tyr Val Pro Gly Arg Thr Ala
             355                 360                 365

Ser Leu Pro Glu Ala Gly Glu Lys Leu Phe Pro Tyr Leu Asp Pro Phe
             370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
             405                 410                 415

Gln Val Pro Pro Arg Cys Pro Val Pro Ser Phe His Val Glu Leu Cys
             420                 425                 430

Arg Glu Gly Lys Asn Leu Leu Lys His Phe Arg Phe Arg Asp Leu Glu
             435                 440                 445

Glu Asp Pro Tyr Leu Pro Gly Asn Pro Arg Glu Leu Ile Ala Tyr Ser
             450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
             485                 490                 495

Tyr Arg Tyr Thr Val Trp Val Gly Phe Asn Pro Asp Glu Phe Leu Ala
             500                 505                 510

Asn Phe Ser Asp Ile His Ala Gly Glu Leu Tyr Phe Val Asp Ser Asp
             515                 520                 525

Pro Leu Gln Asp His Asn Met Tyr Asn Asp Ser Gln Gly Gly Asp Leu
             530                 535                 540

Phe Gln Leu Leu Met Pro
545                 550

<210> SEQ ID NO 28
<211> LENGTH: 550

```
<212> TYPE: PRT
<213> ORGANISM: Pan troglodytes (Chimpanzee)
<220> FEATURE:
<223> OTHER INFORMATION: TR/K6ZGI9_PANTR

<400> SEQUENCE: 28
```

| | | | | | | | | | | | | | | |
|---|---|---|---|---|---|---|---|---|---|---|---|---|---|---|
| Met | Pro | Pro | Pro | Arg | Thr | Gly | Arg | Gly | Leu | Pro | Trp | Leu | Gly | Leu | Val |
| 1 | | | | 5 | | | | | 10 | | | | | 15 |

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Pro Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

```
Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Ala Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Ile Gly Phe Asn Pro Asp Glu Phe Leu Ala
                500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
530                 535                 540

Phe Gln Leu Leu Met Pro
545                 550

<210> SEQ ID NO 29
<211> LENGTH: 550
<212> TYPE: PRT
<213> ORGANISM: Pan troglodytes (Chimpanzee)
<220> FEATURE:
<223> OTHER INFORMATION: TR/K7BKV4_PANTR

<400> SEQUENCE: 29

Met Pro Pro Pro Arg Thr Gly Arg Gly Leu Pro Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190
```

Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
                260                 265                 270

Arg Glu Asp Val Gln Ala Leu Asn Ile Ser Val Pro Tyr Gly Pro Ile
            275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
                340                 345                 350

Val Ala Thr His Val Pro Leu Met Phe Tyr Val Pro Gly Arg Thr Ala
            355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Ala Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Ile Gly Phe Asn Pro Asp Glu Phe Leu Ala
            500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
                530                 535                 540

Phe Gln Leu Leu Met Pro
545                 550

<210> SEQ ID NO 30
<211> LENGTH: 550
<212> TYPE: PRT
<213> ORGANISM: Macaca mulatta (Rhesus macaque)
<220> FEATURE:
<223> OTHER INFORMATION: TR/H9FTX2_MACMU

<400> SEQUENCE: 30

```
Met Pro Thr Pro Gly Ser Gly Arg Gly Phe Leu Trp Leu Gly Leu Val
1               5                   10                  15

Leu Ser Ser Val Cys Val Ala Leu Gly Cys Glu Thr Gln Ala Asn Ser
            20                  25                  30

Thr Thr Asp Ala Leu Asn Ile Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
            115                 120                 125

Val Thr Met Ser Val Gly Lys Val Phe His Pro Gly Ile Thr Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Val Asp Val Pro
            180                 185                 190

Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
            275                 280                 285

Pro Val Glu Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
            355                 360                 365

Ser Leu Pro Glu Ala Gly Glu Lys Leu Phe Pro Tyr Leu Asp Pro Phe
370                 375                 380

Asp Ser Ala Ser Glu Leu Met Glu Pro Gly Arg Gln Ser Met Asp Leu
385                 390                 395                 400
```

```
Val Glu Leu Val Ser Leu Phe Pro Thr Leu Ala Gly Leu Ala Gly Leu
            405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
450                 455                 460

Gln Tyr Pro Arg Pro Ala Asp Phe Pro Gln Trp Asn Ser Asp Lys Pro
465                 470                 475                 480

Ser Leu Lys Asp Ile Lys Ile Met Gly Tyr Ser Ile Arg Thr Ile Asp
            485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
            530                 535                 540

Phe Gln Leu Leu Met Pro
545                 550

<210> SEQ ID NO 31
<211> LENGTH: 550
<212> TYPE: PRT
<213> ORGANISM: Callithrix jacchus (White-tufted-ear marmoset)
<220> FEATURE:
<223> OTHER INFORMATION: TRF7EJG2_CALJA

<400> SEQUENCE: 31

Met Pro Pro Arg Thr Ser Arg Cys Leu Leu Leu Gly Leu Val
1               5                   10                  15

Leu Gly Ser Val Cys Val Thr Leu Gly Ser Gln Ala Gln Ala Ser Ser
            20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
            85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Asp Asn Gly Tyr
            115                 120                 125

Val Thr Met Ser Val Gly Lys Val Phe His Pro Gly Ile Ser Ser Asn
130                 135                 140

His Ser Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
            165                 170                 175

Glu Leu His Ala Asn Leu Leu Cys Pro Val Asp Val Asp Val Pro
            180                 185                 190

Glu Gly Thr Leu Pro Asp Lys Gln Ser Thr Glu Glu Ala Ile Arg Leu
            195                 200                 205
```

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly His Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr Arg Val Pro Leu Met Phe Tyr Val Pro Gly Arg Thr Ala
        355                 360                 365

Ser Leu Pro Glu Ala Asp Glu Lys Leu Phe Pro Tyr Val Asp Pro Phe
    370                 375                 380

His Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Ser Leu Leu Lys His Phe Arg Phe His Gly Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ala Asp Phe Pro Gln Trp Asn Ser Asp Lys Pro
465                 470                 475                 480

Ser Leu Lys Tyr Ile Lys Ile Met Gly Tyr Ser Ile Arg Thr Val Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Glu Leu
    530                 535                 540

Phe Gln Ser Leu Met Pro
545                 550

<210> SEQ ID NO 32
<211> LENGTH: 550
<212> TYPE: PRT
<213> ORGANISM: Callithrix jacchus (White-tufted-ear marmoset)
<220> FEATURE:
<223> OTHER INFORMATION: TR/U3DTL8_CALJA

<400> SEQUENCE: 32

Met Pro Pro Pro Arg Pro Ser Arg Cys Leu Leu Leu Gly Leu Val
1               5                   10                  15

```
Leu Gly Ser Val Cys Val Thr Leu Gly Ser Gln Ala Gln Ala Ser Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Asp Asn Gly Tyr
        115                 120                 125

Val Thr Met Ser Val Gly Lys Val Phe His Pro Gly Ile Ser Ser Asn
130                 135                 140

His Ser Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Asp Val Pro
            180                 185                 190

Glu Gly Thr Leu Pro Asp Lys Gln Ser Thr Glu Glu Ala Ile Arg Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly His Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr Arg Val Pro Leu Met Phe Tyr Val Pro Gly Arg Thr Ala
        355                 360                 365

Ser Leu Pro Glu Ala Asp Glu Lys Leu Phe Pro Tyr Val Asp Pro Phe
370                 375                 380

His Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430
```

-continued

```
Arg Glu Gly Lys Ser Leu Leu Lys His Phe Arg Phe His Gly Leu Glu
            435                 440                 445

Glu Asp Pro Tyr Leu Pro Gly Asn Pro Arg Glu Leu Ile Ala Tyr Ser
450                 455                 460

Gln Tyr Pro Arg Pro Ala Asp Phe Pro Gln Trp Asn Ser Asp Lys Pro
465                 470                 475                 480

Ser Leu Lys Tyr Ile Lys Ile Met Gly Tyr Ser Ile Arg Thr Val Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Glu Leu
530                 535                 540

Phe Gln Ser Leu Met Pro
545                 550
```

<210> SEQ ID NO 33
<211> LENGTH: 550
<212> TYPE: PRT
<213> ORGANISM: Macaca mulatta (Rhesus macaque)
<220> FEATURE:
<223> OTHER INFORMATION: TR/G7NRX7_MACMU

<400> SEQUENCE: 33

```
Met Pro Thr Pro Gly Ser Gly Arg Gly Phe Leu Trp Leu Gly Leu Val
1               5                   10                  15

Leu Ser Ser Val Cys Val Ala Leu Gly Cys Glu Thr Gln Ala Asn Ser
                20                  25                  30

Thr Thr Asp Ala Leu Asn Ile Leu Leu Ile Ile Val Asp Asp Leu Arg
            35                  40                  45

Pro Ser Leu Gly Cys Tyr Gly Asp Lys Leu Val Arg Ser Pro Asn Ile
50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Thr Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240
```

```
Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Glu Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ala Asp Phe Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Leu Gln Leu Leu Met Pro
545                 550

<210> SEQ ID NO 34
<211> LENGTH: 550
<212> TYPE: PRT
<213> ORGANISM: Macaca fascicularis (Crab-eating macaque; Cynomologous
      monkey)
<220> FEATURE:
<223> OTHER INFORMATION: RT/G7Q1V9_MACFA

<400> SEQUENCE: 34

Met Pro Thr Pro Gly Ser Gly Arg Gly Phe Leu Trp Leu Gly Leu Val
1               5                   10                  15

Leu Ser Ser Val Cys Val Ala Leu Gly Cys Glu Thr Gln Ala Asn Ser
                20                  25                  30

Thr Thr Asp Ala Leu Asn Ile Leu Leu Ile Ile Val Asp Asp Leu Arg
            35                  40                  45
```

-continued

```
Pro Ser Leu Gly Cys Tyr Gly Asp Lys Leu Val Arg Ser Pro Asn Ile
    50              55                  60

Asp Gln Leu Ala Ser His Ser Leu Leu Phe Gln Asn Ala Phe Ala Gln
65              70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Thr Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Glu Phe Gln Arg Lys Ile Arg Gln Ser Tyr Phe Ala Ser Val
    290                 295                 300

Ser Tyr Leu Asp Thr Gln Val Gly His Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460
```

Gln Tyr Pro Arg Pro Ala Asp Phe Pro Gln Trp Asn Ser Asp Lys Pro
465                 470                 475                 480

Ser Leu Lys Asp Ile Lys Ile Met Gly Tyr Ser Ile Arg Thr Ile Asp
            485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
            530                 535                 540

Phe Gln Leu Leu Met Pro
545             550

<210> SEQ ID NO 35
<211> LENGTH: 550
<212> TYPE: PRT
<213> ORGANISM: Pongo abelii (Sumatran orangutan)
<220> FEATURE:
<223> OTHER INFORMATION: TR/H2PX10_PONAB

<400> SEQUENCE: 35

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asp Ser
            20                  25                  30

Thr Thr Asp Gly Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
            85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
            115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
            165                 170                 175

Glu Leu His Ala Asn Leu Ile Ala Lys Lys Met Cys Trp Met Phe Pro
            180                 185                 190

Arg Ala Pro Cys Cys Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
            210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
            245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
            275                 280                 285

Pro Val Asp Phe Gln Lys Ile Arg Gln Ser Tyr Phe Ala Ser Val
        290                 295                 300

Ser Tyr Leu Asp Thr Gln Val Gly Arg Leu Leu Ser Thr Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ala Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
530                 535                 540

Phe Gln Leu Leu Met Pro
545                 550

<210> SEQ ID NO 36
<211> LENGTH: 550
<212> TYPE: PRT
<213> ORGANISM: Chlorocebus sabaeus (Green monkey)
<220> FEATURE:
<223> OTHER INFORMATION: TR/A0A0D9R4D1_CHLSB

<400> SEQUENCE: 36

Met Pro Thr Pro Gly Ser Gly Arg Gly Phe Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Ile Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

```
Gln Ala Val Cys Ala Pro Ser Arg Val Ser Phe Leu Thr Gly Arg Arg
                85                  90                  95

Pro Asp Thr Thr Arg Leu His Asn Phe Asn Ser Tyr Trp Arg Val His
            100                 105                 110

Ala Gly Asn Phe Ser Thr Ile Pro Gln Tyr Phe Lys Glu Asn Gly Tyr
            115                 120                 125

Val Thr Met Ser Val Gly Lys Val Phe His Pro Gly Ile Thr Ser Asn
            130                 135                 140

His Thr Asp Asp Ser Pro Tyr Ser Trp Ser Phe Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Asp Val Pro
            180                 185                 190

Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
                260                 265                 270

Arg Glu Asp Val Gln Ala Leu Asn Ile Ser Val Pro Tyr Gly Pro Ile
            275                 280                 285

Pro Val Glu Phe Gln Arg Lys Ile Arg Gln Ser Tyr Phe Ala Ser Val
            290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
            355                 360                 365

Ser Leu Pro Glu Ala Gly Glu Lys Leu Phe Pro Tyr Leu Asp Pro Phe
    370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
            450                 455                 460

Gln Tyr Pro Arg Pro Ala Asp Phe Pro Gln Trp Asn Ser Asp Lys Pro
465                 470                 475                 480

Asn Leu Lys Asp Ile Lys Ile Met Gly Tyr Ser Ile Arg Thr Ile Asp
                485                 490                 495
```

```
Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
530                 535                 540

Phe Gln Leu Leu Met Pro
545             550

<210> SEQ ID NO 37
<211> LENGTH: 550
<212> TYPE: PRT
<213> ORGANISM: Nomascus leucogenys (Northern white-cheeked gibbon)
<220> FEATURE:
<223> OTHER INFORMATION: TR/G1RST8/G1RST8_NOMLE
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (163)..(168)
<223> OTHER INFORMATION: Xaa can be any naturally occurring amino acid

<400> SEQUENCE: 37

Met Ser Pro Pro Arg Thr Gly Gln Gly Leu Leu Trp Leu Gly Val Val
1               5                   10                  15

Leu Ser Ser Val Cys Val Ala Xaa Val Thr Ser Pro Lys Pro Pro Ser
            20                  25                  30

Phe Val Asp Ala Leu Asn Val Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Xaa Xaa Xaa Xaa Xaa Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255
```

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ala Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Ser Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 38
<211> LENGTH: 550
<212> TYPE: PRT
<213> ORGANISM: Macaca mulatta (Rhesus macaque)
<220> FEATURE:
<223> OTHER INFORMATION: UPI0000D9F625

<400> SEQUENCE: 38

Met Pro Thr Pro Gly Ser Gly Arg Gly Phe Leu Trp Leu Gly Leu Val
1               5                   10                  15

Leu Ser Ser Val Cys Val Ala Leu Gly Cys Glu Thr Gln Ala Asn Ser
                20                  25                  30

Thr Thr Asp Ala Leu Asn Ile Leu Leu Ile Ile Val Asp Asp Leu Arg
            35                  40                  45

Pro Ser Leu Gly Cys Tyr Gly Asp Lys Leu Val Arg Ser Pro Asn Ile
    50                  55                  60

```
Asp Gln Leu Ala Ser His Ser Leu Leu Phe Gln Asn Ala Phe Ala Gln
 65                  70                  75                  80

Gln Ala Val Cys Ala Pro Ser Arg Val Ser Phe Leu Thr Gly Arg Arg
                 85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Thr Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Asp Val Pro
        180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
            275                 280                 285

Pro Val Glu Phe Gln Arg Lys Ile Arg Gln Ser Tyr Phe Ala Ser Val
    290                 295                 300

Ser Tyr Leu Asp Thr Gln Val Gly His Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ala Asp Phe Pro Gln Trp Asn Ser Asp Lys Pro
465                 470                 475                 480
```

```
Ser Leu Lys Asp Ile Lys Ile Met Gly Tyr Ser Ile Arg Thr Ile Asp
            485                 490                 495

Tyr Arg Tyr Thr Val Trp Val Gly Phe Asn Pro Asp Glu Phe Leu Ala
        500                 505                 510

Asn Phe Ser Asp Ile His Ala Gly Glu Leu Tyr Phe Val Asp Ser Asp
    515                 520                 525

Pro Leu Gln Asp His Asn Met Tyr Asn Asp Ser Gln Gly Gly Asp Leu
530                 535                 540

Leu Gln Leu Leu Met Pro
545                 550

<210> SEQ ID NO 39
<211> LENGTH: 550
<212> TYPE: PRT
<213> ORGANISM: Pan paniscus (Pygmy chimpanzee; Bonobo)
<220> FEATURE:
<223> OTHER INFORMATION: UPI0000274358B

<400> SEQUENCE: 39

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Arg Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285
```

```
Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Met Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
530                 535                 540

Phe Gln Leu Leu Met Pro
545                 550

<210> SEQ ID NO 40
<211> LENGTH: 550
<212> TYPE: PRT
<213> ORGANISM: Papio Anubis (Olive baboon)
<220> FEATURE:
<223> OTHER INFORMATION: UPI00027F6FC5

<400> SEQUENCE: 40

Met Pro Thr Pro Gly Ser Gly Arg Gly Phe Leu Trp Leu Gly Leu Val
1               5                   10                  15

Leu Ser Ser Val Cys Val Ala Leu Gly Cys Glu Met Gln Ala Asn Ser
                20                  25                  30

Thr Thr Asp Ala Leu Asn Ile Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95
```

```
Pro Asp Thr Thr Arg Leu Tyr Asp Phe Asn Ser Tyr Trp Arg Val His
        100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Thr Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
        210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
        260                 265                 270

Arg Glu Asp Val Gln Ala Leu Asn Ile Ser Val Pro Tyr Gly Pro Ile
        275                 280                 285

Pro Val Glu Phe Gln Arg Lys Ile Arg Gln Ser Tyr Phe Ala Ser Val
        290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Val Ala Phe Thr Ser Asp His Gly
            325                 330                 335

Trp Ala Leu Gly Glu His Gly Glu Trp Ala Lys Tyr Ser Asn Phe Asp
        340                 345                 350

Val Ala Thr His Val Pro Leu Met Phe Tyr Val Pro Gly Arg Thr Ala
            355                 360                 365

Ser Leu Pro Glu Ala Gly Glu Lys Leu Phe Pro Tyr Leu Asp Pro Phe
    370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
        420                 425                 430

Arg Glu Gly Lys Asn Leu Leu Lys His Phe Arg Phe Arg Asp Leu Glu
    435                 440                 445

Glu Asp Pro Tyr Leu Pro Gly Asn Pro Arg Glu Leu Ile Ala Tyr Ser
        450                 455                 460

Gln Tyr Pro Arg Pro Ala Asp Phe Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
        500                 505                 510
```

```
Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
        530                 535                 540

Phe Gln Leu Leu Met Pro
545             550

<210> SEQ ID NO 41
<211> LENGTH: 550
<212> TYPE: PRT
<213> ORGANISM: Saimiri boliviensis (Bolivian squirrel monkey)
<220> FEATURE:
<223> OTHER INFORMATION: UPI00027FAE03

<400> SEQUENCE: 41

Met Pro Pro Pro Arg Thr Gly Leu Cys Leu Leu Leu Gly Leu Val
1               5                   10                  15

Leu Gly Ser Val Cys Val Thr Leu Gly Ser Gln Ala Gln Ala Asn Ser
            20                  25                  30

Thr Thr Asp Ala Leu Asn Val Leu Ile Ile Val Asp Asp Leu Arg
        35                  40                  45

Pro Ser Leu Gly Cys Tyr Gly Asp Lys Leu Val Arg Ser Pro Asn Ile
50                  55                  60

Asp Gln Leu Ala Ser His Ser Leu Leu Phe Gln Asn Ala Phe Val Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Asp Asn Gly Tyr
        115                 120                 125

Val Thr Met Ser Val Gly Lys Val Phe His Pro Gly Ile Ser Ser Asn
130                 135                 140

His Ser Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Val Asp Val Pro
            180                 185                 190

Glu Gly Thr Leu Pro Asp Lys Gln Ser Thr Glu Glu Ala Ile Arg Leu
        195                 200                 205

Leu Lys Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly His Leu Leu Ser Ala Leu Asp Asp
305                 310                 315                 320
```

```
Leu His Leu Ala Asn Ser Thr Ile Val Ala Phe Thr Ser Asp His Gly
            325                 330                 335

Trp Ala Leu Gly Glu His Gly Glu Trp Ala Lys Tyr Ser Asn Phe Asp
        340                 345                 350

Val Ala Thr Arg Val Pro Leu Met Phe Tyr Val Pro Gly Arg Thr Ala
        355                 360                 365

Ser Leu Pro Glu Thr Gly Glu Lys Leu Phe Pro Tyr Val Asp Pro Phe
370                 375                 380

His Ser Ala Ser Glu Leu Met Glu Pro Gly Arg Gln Ser Thr Asp Leu
385                 390                 395                 400

Val Glu Leu Val Ser Leu Phe Pro Thr Leu Ala Gly Leu Ala Gly Leu
            405                 410                 415

Gln Val Pro Pro Arg Cys Pro Val Pro Ser Phe His Ile Glu Leu Cys
            420                 425                 430

Arg Glu Gly Lys Asn Leu Leu Lys His Phe Arg Phe His Gly Leu Glu
            435                 440                 445

Glu Asp Pro Tyr Leu Pro Gly Asn Pro Arg Glu Leu Ile Ala Tyr Ser
            450                 455                 460

Gln Tyr Pro Arg Pro Ala Asp Phe Pro Gln Gln Asn Ser Asp Lys Pro
465                 470                 475                 480

Ser Leu Lys Tyr Ile Lys Ile Met Gly Tyr Ser Ile Arg Thr Val Asp
            485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Glu Leu
            530                 535                 540

Phe Gln Ser Leu Met Pro
545                 550

<210> SEQ ID NO 42
<211> LENGTH: 550
<212> TYPE: PRT
<213> ORGANISM: Macaca fascicularis (Crab-eating macaque; Cynomologous
      monkey)
<220> FEATURE:
<223> OTHER INFORMATION: UPI0003ABBF28

<400> SEQUENCE: 42

Met Pro Thr Pro Gly Ser Gly Arg Gly Phe Leu Trp Leu Gly Leu Val
1               5                   10                  15

Leu Ser Ser Val Cys Val Ala Leu Gly Cys Glu Thr Gln Ala Asn Ser
            20                  25                  30

Thr Thr Asp Ala Leu Asn Ile Leu Leu Ile Val Asp Asp Leu Arg
        35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Glu Ala Val Cys Ala Pro Ser Arg Val Ser Phe Leu Thr Gly Arg Arg
            85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
            115                 120                 125
```

-continued

```
Val Thr Met Ser Val Gly Lys Val Phe His Pro Gly Ile Thr Ser Asn
        130                 135                 140
His Thr Asp Asp Ser Pro Tyr Ser Trp Ser Phe Pro Pro Tyr His Pro
145                 150                 155                 160
Ser Ser Glu Lys Tyr Glu Asn Thr Lys Thr Cys Arg Gly Pro Asp Gly
                165                 170                 175
Glu Leu His Ala Asn Leu Leu Cys Pro Val Asp Val Val Asp Val Pro
                180                 185                 190
Glu Gly Thr Leu Pro Asp Lys Gln Ser Thr Glu Gln Ala Ile Gln Leu
            195                 200                 205
Leu Glu Lys Met Lys Thr Ser Ala Ser Pro Phe Phe Leu Ala Val Gly
210                 215                 220
Tyr His Lys Pro His Ile Pro Phe Arg Tyr Pro Lys Glu Phe Gln Lys
225                 230                 235                 240
Leu Tyr Pro Leu Glu Asn Ile Thr Leu Ala Pro Asp Ser Glu Val Pro
                245                 250                 255
Asp Gly Leu Pro Pro Val Ala Tyr Asn Pro Trp Met Asp Ile Arg Gln
                260                 265                 270
Arg Glu Asp Val Gln Ala Leu Asn Ile Ser Val Pro Tyr Gly Pro Ile
                275                 280                 285
Pro Val Glu Phe Gln Arg Lys Ile Arg Gln Ser Tyr Phe Ala Ser Val
            290                 295                 300
Ser Tyr Leu Asp Thr Gln Val Gly Arg Leu Leu Ser Ala Leu Asp Asp
305                 310                 315                 320
Leu Gln Leu Ala Asn Ser Thr Ile Val Ala Phe Thr Ser Asp His Gly
                325                 330                 335
Trp Ala Leu Gly Glu His Gly Glu Trp Ala Lys Tyr Ser Asn Phe Asp
                340                 345                 350
Val Ala Thr His Val Pro Leu Met Phe Tyr Val Pro Gly Arg Thr Ala
                355                 360                 365
Ser Leu Pro Glu Ala Gly Glu Lys Leu Phe Pro Tyr Leu Asp Pro Phe
            370                 375                 380
Asp Ser Ala Ser Glu Leu Met Glu Pro Gly Arg Gln Ser Met Asp Leu
385                 390                 395                 400
Val Glu Leu Val Ser Leu Phe Pro Thr Leu Ala Gly Leu Ala Gly Leu
                405                 410                 415
Gln Val Pro Pro Arg Cys Pro Val Pro Ser Phe His Val Glu Leu Cys
                420                 425                 430
Arg Glu Gly Lys Asn Leu Leu Lys His Phe Arg Phe Arg Asp Leu Glu
            435                 440                 445
Glu Asp Pro Tyr Leu Pro Gly Asn Pro Arg Glu Leu Ile Ala Tyr Ser
450                 455                 460
Gln Tyr Pro Arg Pro Ala Asp Phe Pro Gln Trp Asn Ser Asp Lys Pro
465                 470                 475                 480
Ser Leu Lys Asp Ile Lys Ile Met Gly Tyr Ser Ile Arg Thr Ile Asp
                485                 490                 495
Tyr Arg Tyr Thr Val Trp Val Gly Phe Asn Pro Asp Glu Phe Leu Ala
            500                 505                 510
Asn Phe Ser Asp Ile His Ala Gly Glu Leu Tyr Phe Val Asp Ser Asp
                515                 520                 525
Pro Leu Gln Asp His Asn Met Tyr Asn Asp Ser Gln Gly Gly Asp Leu
530                 535                 540
```

```
Phe Gln Leu Leu Met Pro
545                 550

<210> SEQ ID NO 43
<211> LENGTH: 550
<212> TYPE: PRT
<213> ORGANISM: Rhinopithecus roxellana (Golden snub-nosed monkey)
<220> FEATURE:
<223> OTHER INFORMATION: UPI000533297F

<400> SEQUENCE: 43

Met Pro Thr Pro Ala Ser Gly Arg Gly Phe Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Ile Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Thr Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Val Asp Val Pro
            180                 185                 190

Glu Gly Thr Leu Pro Asp Lys Gln Ser Thr Glu Gln Ala Val Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Ser Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly His Leu Leu Ser Ala Leu Asp Asp
305                 310                 315                 320

Leu Gln Leu Ala Asn Ser Thr Ile Val Ala Phe Thr Ser Asp His Gly
                325                 330                 335

Trp Ala Leu Gly Glu His Gly Glu Trp Ala Lys Tyr Ser Asn Phe Asp
            340                 345                 350
```

-continued

```
Val Ala Thr His Val Pro Leu Met Phe Tyr Val Pro Gly Arg Thr Ala
            355                 360                 365

Ser Leu Pro Glu Ala Gly Glu Lys Leu Phe Pro Tyr Leu Asp Pro Phe
    370                 375                 380

Asp Ser Ala Ser Glu Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
    450                 455                 460

Gln Tyr Pro Arg Pro Ala Asp Phe Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
            515                 520                 525

Pro Phe Gln Asp His Asn Met Tyr Asn Asp Ser Gln Gly Gly Asp Leu
    530                 535                 540

Phe Gln Leu Leu Met Pro
545                 550

<210> SEQ ID NO 44
<211> LENGTH: 550
<212> TYPE: PRT
<213> ORGANISM: Colobus angolensis palliates (Peters Angolan colobus)
<220> FEATURE:
<223> OTHER INFORMATION: UPI0005F40BD2

<400> SEQUENCE: 44

Met Pro Thr Pro Ala Ser Gly Arg Gly Phe Leu Trp Leu Gly Leu Val
1               5                   10                  15

Leu Arg Ser Val Cys Val Ala Leu Gly Ser Glu Thr Gln Ala Asn Ser
            20                  25                  30

Thr Thr Asp Ala Leu Asn Ile Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Thr Pro Ser His Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Thr Ser Asn
    130                 135                 140

His Thr Asp Asp Ser Pro Tyr Ser Trp Ser Phe Pro Pro Tyr His Pro
145                 150                 155                 160
```

```
Ser Ser Glu Lys Tyr Glu Asn Thr Lys Thr Cys Arg Gly Pro Asp Gly
            165                 170                 175
Glu Leu His Ala Asn Leu Leu Cys Pro Val Asp Val Asp Val Pro
        180                 185                 190
Glu Gly Thr Leu Pro Asp Lys Gln Ser Thr Glu Gln Ala Ile Gln Leu
            195                 200                 205
Leu Glu Lys Met Lys Thr Ser Ala Ser Pro Phe Phe Leu Ala Val Gly
    210                 215                 220
Tyr His Lys Pro His Ile Pro Phe Arg Tyr Pro Lys Glu Phe Gln Lys
225                 230                 235                 240
Leu Tyr Pro Leu Glu Asn Ile Thr Leu Ala Pro Asp Ser Glu Val Pro
                245                 250                 255
Asp Gly Leu Pro Pro Val Ala Tyr Asn Pro Trp Met Asp Ile Arg Gln
            260                 265                 270
Arg Glu Asp Val Gln Ala Leu Asn Ile Ser Val Pro Tyr Gly Pro Ile
        275                 280                 285
Pro Val Asp Phe Gln Arg Lys Ile Arg Gln Ser Tyr Phe Ala Ser Val
    290                 295                 300
Ser Tyr Leu Asp Thr Gln Val Gly His Leu Leu Ser Ala Leu Asp Asp
305                 310                 315                 320
Leu Gln Leu Ala Asn Ser Thr Ile Val Ala Phe Thr Ser Asp His Gly
                325                 330                 335
Trp Ala Leu Gly Glu His Gly Glu Trp Ala Lys Tyr Ser Asn Phe Asp
            340                 345                 350
Val Ala Thr His Val Pro Leu Met Phe Tyr Val Pro Gly Arg Thr Ala
        355                 360                 365
Ser Leu Pro Glu Ala Gly Glu Lys Leu Phe Pro Tyr Leu Asp Pro Phe
    370                 375                 380
Asp Ser Ala Ser Glu Leu Met Glu Pro Gly Arg Gln Ser Met Asp Leu
385                 390                 395                 400
Val Glu Leu Val Ser Leu Phe Pro Thr Leu Ala Gly Leu Ala Gly Leu
                405                 410                 415
Gln Val Pro Pro Arg Cys Pro Val Pro Ser Phe His Val Glu Leu Cys
            420                 425                 430
Arg Glu Gly Lys Asn Leu Leu Lys His Phe Arg Phe Arg Asp Leu Glu
        435                 440                 445
Glu Asp Pro Tyr Leu Pro Gly Asn Pro Arg Glu Leu Ile Ala Tyr Ser
    450                 455                 460
Gln Tyr Pro Arg Pro Ala Asp Phe Pro Gln Trp Asn Ser Asp Lys Pro
465                 470                 475                 480
Ser Leu Lys Asp Ile Lys Ile Met Gly Tyr Ser Ile Arg Thr Ile Asp
                485                 490                 495
Tyr Arg Tyr Thr Val Trp Val Gly Phe Asn Pro Asp Glu Phe Leu Ala
            500                 505                 510
Asn Phe Ser Asp Ile His Ala Gly Glu Leu Tyr Phe Val Asp Ser Asp
        515                 520                 525
Pro Leu Gln Asp His Asn Met Tyr Asn Asp Ser Gln Gly Gly Asp Leu
    530                 535                 540
Phe Gln Leu Leu Met Pro
545                 550

<210> SEQ ID NO 45
<211> LENGTH: 16
<212> TYPE: PRT
```

```
<213> ORGANISM: Homo sapiens
<220> FEATURE:
<223> OTHER INFORMATION: Y-sulfation site

<400> SEQUENCE: 45

Pro Ser Ser Glu Lys Tyr Glu Asn Thr Lys Thr Cys Arg Gly Pro Asp
1               5                   10                  15

<210> SEQ ID NO 46
<211> LENGTH: 9
<212> TYPE: PRT
<213> ORGANISM: Homo sapiens
<220> FEATURE:
<223> OTHER INFORMATION: portion of a sequence from human IDS

<400> SEQUENCE: 46

Thr Asp Ala Leu Asn Val Leu Leu Ile
1               5

<210> SEQ ID NO 47
<211> LENGTH: 9
<212> TYPE: PRT
<213> ORGANISM: Homo sapiens
<220> FEATURE:
<223> OTHER INFORMATION: portion of a sequence from human IDS

<400> SEQUENCE: 47

Ala Leu Asn Val Leu Leu Ile Ile Val
1               5

<210> SEQ ID NO 48
<211> LENGTH: 25
<212> TYPE: PRT
<213> ORGANISM: Homo sapiens
<220> FEATURE:
<223> OTHER INFORMATION: signal sequence

<400> SEQUENCE: 48

Met Pro Pro Pro Arg Thr Gly Arg Gly Leu Leu Trp Leu Gly Leu Val
1               5                   10                  15

Leu Ser Ser Val Cys Val Ala Leu Gly
            20                  25
```